US008704043B2

(12) United States Patent
Frankard et al.

(10) Patent No.: US 8,704,043 B2
(45) Date of Patent: Apr. 22, 2014

(54) PLANTS HAVING INCREASED YIELD-RELATED TRAITS AND A METHOD FOR MAKING THE SAME

(75) Inventors: Valerie Frankard, Waterloo (BE); Andy Allen, La Jolla, CA (US); Chris Bowler, Paris Cedex (FR)

(73) Assignee: CropDesign N.V., Zwijnaarde (BE)

( * ) Notice: Subject to any disclaimer, the term of this patent is extended or adjusted under 35 U.S.C. 154(b) by 522 days.

(21) Appl. No.: 12/743,388

(22) PCT Filed: Nov. 21, 2008

(86) PCT No.: PCT/EP2008/065947

§ 371 (c)(1),
(2), (4) Date: Sep. 10, 2010

(87) PCT Pub. No.: WO2009/065912

PCT Pub. Date: May 28, 2009

(65) Prior Publication Data

US 2011/0004963 A1 Jan. 6, 2011

Related U.S. Application Data

(60) Provisional application No. 60/990,132, filed on Nov. 26, 2007.

(30) Foreign Application Priority Data

Nov. 22, 2007 (EP) .................................... 07121362

(51) Int. Cl.

| | |
|---|---|
| ***A01H 1/00*** | (2006.01) |
| ***A01H 5/00*** | (2006.01) |
| ***C12N 5/04*** | (2006.01) |
| ***C12N 15/00*** | (2006.01) |
| ***C07H 21/04*** | (2006.01) |

(52) U.S. Cl.

USPC ........... 800/290; 800/298; 800/320; 435/419; 435/320.1; 536/23.7

(58) Field of Classification Search

None

See application file for complete search history.

(56) References Cited

U.S. PATENT DOCUMENTS

2003/0204867 A1* 10/2003 Frommer et al. ............. 800/278
2008/0148432 A1* 6/2008 Abad ............................ 800/279

FOREIGN PATENT DOCUMENTS

WO WO-2006/076423 A2 7/2006
WO WO2006/076423 A2 * 7/2006

OTHER PUBLICATIONS

Ludewig et al., FEBS Lett 581 :2301-08 (2007).*
GenBank_AAV70490, (2005).*
Lazar et al., Mol Cell Biol 8:1247 (1988).*
Ludewig et al. (FEBS Lett 581:2301-08 (2007).*
von Wiren et al. (Curr Opin Plant Biol 3:254-261 (2000).*
GenBank search Abad 15111, (2012).*
International Preliminary Report on Patentability for PCT/EP2008/065947 mailed May 25, 2010.

* cited by examiner

*Primary Examiner* — Brent T Page
*Assistant Examiner* — Russell Boggs
(74) *Attorney, Agent, or Firm* — Novak Druce Connolly Bove + Quigg LLP

(57) ABSTRACT

The present invention relates generally to the field of molecular biology and concerns a method for increasing various plant yield-related traits by increasing expression in a plant of a nucleic acid sequence encoding an ammonium transporter (AMT) polypeptide. The present invention also concerns plants having increased expression of a nucleic acid sequence encoding an AMT polypeptide, which plants have increased yield-related traits relative to control plants. The invention also provides constructs useful in the methods of the invention.

21 Claims, 21 Drawing Sheets

```
                         1                                                50
  Phatr_AMT1     (1) -----------------MSFDLDAFCTGLTAA-----------SSSSEQA
  Cylfu_AMT1     (1) -------------MAEFDNTFILDFCSGGNES-----------SS-DVQA
 Cylfu_AMT2a     (1) -------------MAEFDNTFILEFCSGGNES-----------SS-DVQV
  Thaps_AMT1     (1) --------------MAEPTTTIGDFN--VTAW-----------CGDDAVA
  Phatr_AMT2     (1) ----------------MSSSAIYQSCAGQFDS-----------GEQLDQL
  Thaps_AMT2     (1) ---------------MSEDPSIFEVCTGQLG------------TDLTVEL
  Phatr_AMT4     (1) MDDASFIQSLVEGYGTSSNHTTVYGYCSNEA------------EGETNLI
  Phatr_AMT6     (1) --------------MSTSDGSLFQQCSAVAG------------DSDPSRI
  Phatr_AMT3     (1) ------MNSRTFSYNSNDGNELLDACMAYLG-----------ANATTYDL
  Phatr_AMT7     (1) ----------MISTGSSTSTNAYGTCSVQLG-----------ENSSAKEL
  Phatr_AMT5     (1) --------------MSHSSLDVFGTCLAQVG-----------EDATTKEL
  Thaps_AMT3     (1) ----------MFQVSRAGHVSVYEVCKSFVN-------PEDSQADQFDAM
  Thaps_AMT4     (1) -------------MSSSVRTSLYEACKSTQSNSTFSNSTLDDALSRQEQI
  Thaps_AMT6     (1) -------------MASSTTTDTYQTCLSDLSATS-----SNGSSPTTDAL
   Consensus     (1)                S   T IYE C G  G             S    L

                         51                                              100
  Phatr_AMT1    (23) VCALQTIVAGVSKTVGGIDAEGITAGVDTFFLIFAGALVFMMQAGFAMLC
  Cylfu_AMT1    (26) LCQVAGLANGTSASAA-----GLVEGINTFFLLFAGALVFLMQAGFAMLC
 Cylfu_AMT2a    (26) LCQVASLANGTSASAG-----GLTEGINTFFLLFAGALVFIMQAGFAMLC
  Thaps_AMT1    (24) TYEGQSVENGICAAYAYT--DETNTGLDVFYLLFAAAMVFFMQAGFAMLC
  Phatr_AMT2    (24) LQCLSTGHDGALSDQTSN----LAGGIDAFYLIFAGALVYFMQTGFAMLC
  Thaps_AMT2    (24) LQCVSDGAESAKDDVIS------G--VNSFYLIFAGALVFFMQVGFAMLC
  Phatr_AMT4    (39) LQCITEVMEQKQ--------LEGDRNVNRWLMLFSGGLIFFMQTGFAMLC
  Phatr_AMT6    (25) LQCVSDALETNQ--------NDRAADLNNWFLIIAGALVFFMQSGFAMLC
  Phatr_AMT3    (34) LGCVSAQLSNEVGS---------REFSRSVLLVYAAALVFFMQAGFAMLC
  Phatr_AMT7    (30) LECVSDYLQNQE-----------APFSSTLVLTFAGAIVFLMQAGFAMVC
  Phatr_AMT5    (26) LECVSFSLSRAVPDGLDE--PSSKGFTRSIVVVFAAALVFFMQAGFAMLC
  Thaps_AMT3    (34) LQCVGE----------------SNGKSIDAFFLIYASSLVFFMQAGFAMLC
  Thaps_AMT4    (38) FRCISE---------------SNANSIDTFFLLYASSLVFFMQAGFAMLC
  Thaps_AMT6    (33) LQCISSSFDAQTA--------STHASINTFFLLYAATLVFFMQAGFAMVS
  Consensus     (51) L CVS                   I TFFLLFAGALVFFMQAGFAMLC
  Beginning of the Conserved Domain (CD)                  XXXXXXXXX

                         101                                             150
  Phatr_AMT1    (73) AGSVRQKNVKNIMLKNLLDACGGAIGFYTVGFGFAYGGDDTTD-------
  Cylfu_AMT1    (71) AGSVRQKNVKNIMLKNMLDACGGAIGFWTIGYAFAYADNSSGD-------
 Cylfu_AMT2a    (71) AGSVRQKNVKNIMLKNMLDACGGAIGFWTIGYAFAYADNSSGN-------
  Thaps_AMT1    (72) AGSVRQKNVKNIMLKNILDACGGALGFWSVGFAFAYGGSGPEK-------
  Phatr_AMT2    (70) AGSIRAKNVKNVILWNLLDSCGGGLAFWSVGYAFAYGGDNAGS-------
  Thaps_AMT2    (66) AGSIREKNVKNVLLWNLLDSAGGAFGFWSIGYAFAYGGDDITKG------
  Phatr_AMT4    (81) AGCVRKKNVQNTMLKNLLDACGAALGFFLLGYAFAFGGQDDRD-------
  Phatr_AMT6    (67) AGCVRKKNVQNTMLKNLLDACGAALGFYVIGYALAFGGQNERS-------
  Phatr_AMT3    (75) AGAVRKKNVQNTMLKNLLDACGAAVAFFIVGYAIAFGGMEP--------E
  Phatr_AMT7    (69) AGAVRTKNVQNAMLKNLLDACGASLAFFSIGYALGFGGMEP--------E
  Phatr_AMT5    (74) AGAVRAKNVQNTMLKNLLDACGAAIAFFTVGYAFAFGGTDFPTDTDTDTG
  Thaps_AMT3    (69) AGCVQHKNVQNSMLKNLLDACGAALGFYSVGYAFAYGGMDYSDP------
  Thaps_AMT4    (73) AGSVRKKNVTNTMLKNLLDACGAALGFYSVGYAFAYGGSVDAG-------
  Thaps_AMT6    (75) AGCVRTNNVQNTLLKNLLDACGAALGFYTVGYAFAWGGSLDTATT-----
  Consensus    (101) AGSVR KNVQNTMLKNLLDACGAALGFWSVGYAFAYGG D
  CD (cont'd)        XXXXXXXXXXXXXXXXXXXXXXXXXXXXXXXXXXXXXXXXXXXXXXXXXX
```

FIGURE 3

```
                   151                                              200
 Phatr_AMT1  (116) ---KTFIGNSYFALRDYTN----YAGFFFQFAFAATAATIVAGTVAERCK
 Cylfu_AMT1  (114) ---KTFIGGKNFFVNQLDESGGAWIGFFFQFAFAATAATIVAGTVAERCK
Cylfu_AMT2a  (114) ---KTFIGGKNFFVNQLDESGGAWIGFFFQFAFAATAATIVAGTVAERCK
 Thaps_AMT1  (115) ---KGFIGNEGFFLGDFTTGG-DLIGWFFQFAFAATAATIVAGTVAERCK
 Phatr_AMT2  (113) ---KTFVGNAGFFLQGDDIR---LENWFFQFAFACALSSIVAGTIAERTQ
 Thaps_AMT2  (110) ---KTFIGNADFFLSG-ETD---MEFWFFQYAFACALSSIVAGTIAERTK
 Phatr_AMT4  (124) --DVTFIGTSNFLNTG---KV-DMSFWFFQFAFSATAVTIVAGTLAERCQ
 Phatr_AMT6  (110) --DVTFVGTTDFFNWNSAVPV-NQAFWFFEFAFSATSVTIVAGTLAERCQ
 Phatr_AMT3  (117) SPNKTFLGNTNFFLMG-VDD---LAFWLFQYAFSAASATIVAGTLAERCQ
 Phatr_AMT7  (111) SSKKTFVGHSQFFLMD-VDD---YAFWLFQYAFSAASATIVAGTLAERCQ
 Phatr_AMT5  (124) NNQTTFIGTSNFFLVN-VDD---YSFWLFQYAFSAASATIVAGTLAERCQ
 Thaps_AMT3  (113) --NKTFIGTENFFLMG-VDD---FMFWLFQFAFAASAATIVAGTLAERCQ
 Thaps_AMT4  (116) --KKTFIGMSNFFLQD-VDN---YMFWLFQFAFAATSATIVAGTLAERCQ
 Thaps_AMT6  (120) --ERTFIGTQNFFLMD-VDSS-QDSFWLFQLAFCSASATIVAGTLAERCQ
 Consensus   (151)    KTFIG SNFFL    D    YAFWFFQFAFAATAATIVAGTLAERCQ
 CD (cont'd)       XXXXXXXXXXXXXXXXXXXXXXXXXXXXXXXXXXXXXXXXXXXXXXXXXX

                   201                                              250
 Phatr_AMT1  (159) MSAYLCYSLFLTGFVYPVVVRSVWSSNGFLSAFSADPFQG-VGTVDFAGS
 Cylfu_AMT1  (161) MSAYLCYSVFLTGFVYPVVVHSIWSADGWLTAFRDDPWKG-VGVIDFAGS
Cylfu_AMT2a  (161) MSAYLCYSIFLTGFVYPVVVHSIWSADGWLTAFRDDPWQG-VGVIDFAGS
 Thaps_AMT1  (161) FEAYLCYSLMLTGFVYPVIVYSIWSSSGFLTAFNDDPAFG-CGMHDFAGS
 Phatr_AMT2  (157) MKAYLMYSVFLAGFVYPVVAHAFWSSNGFLSNTATDPLWG-SGAIDLAGS
 Thaps_AMT2  (153) MMAYLCYSIFLCGFVYPVCAHAFWSQNGFLSAFAAEPLWG-SGVIDFAGS
 Phatr_AMT4  (168) MVAYLCYSIFLTGFVYPVAAHTIWSRNGFLSSTAVDPFQG-VGAIDFAGS
 Phatr_AMT6  (157) MVAYLCYSVFLTGFVYPVVAHSIWSNNGFLSAFAAEPFQG-IGVLDFAGS
 Phatr_AMT3  (163) MVAYLCYSVMLTGWVYPIIAHAIWSPNGWLSASSVDPLWG-VGMVDFAGS
 Phatr_AMT7  (157) MTAYLCYSLMLTGWVYPVILHSIWNPNGWLSAYSVDPLWG-SGLVDFAGS
 Phatr_AMT5  (170) MAAYLGYSALLTGWVYPIVAHAVWNVHGFLSAHAVEPLWG-VGMVDFAGS
 Thaps_AMT3  (157) MTAYLCYSVAVTGFVYPVVVHSVWSPQGFLCGQAVSPLFG-VGVVDFAGS
 Thaps_AMT4  (160) MTAYLCYSIALTGFVYPVVAHSIWSQQGFLSATAQDPLWG-TGFIDFAGS
 Thaps_AMT6  (166) MVAYLAYSMTIAGFVYPVVVHSIWSPSGFLSATRETDLFLDVGMIDFAGS
 Consensus   (201) M AYLCYSVFLTGFVYPVVAHSIWS NGFLSAFA DPLWG VGVIDFAGS
 CD (cont'd)       XXXXXXXXXXXXXXXXXXXXXXXXXXXXXXXXXXXXXXXXXXXXXXXXXX
  PS01219                                                       DFAGS

                   251                                              300
 Phatr_AMT1  (208) GVVHMTGGLTALIAAIVLGPRKGRFYDEDGNPLETPASFPAHSVALQILG
 Cylfu_AMT1  (210) GVVHMTGGATALVAAIVLGPRKGRFYDEDGNALETPASFPAHSVALQVLG
Cylfu_AMT2a  (210) GVVHMCGGATALVAAIVLGPRKGRFYDEDGNALETPASFPAHSVALQVLG
 Thaps_AMT1  (210) GVVHMTGGITALWAAKILGPRIGRFYDADGNELPEPVSFPPHSVALQVLG
 Phatr_AMT2  (206) GPVHMTGGVTALAAALVLGPRIGRFYDKEGNPLEEPAEFPPHSVALQFLG
 Thaps_AMT2  (202) GPVHMCGGVAALVMAIILGPRRGRFYDDDGVVLDEPKSMGPHSVTLQFLG
 Phatr_AMT4  (217) GVVHVTGGTTALVATYILGARKGRFYDNRGRQLETPKSFPGHSVALQLLG
 Phatr_AMT6  (206) GVVHVTGGTTALVATYMLGARKGRFYDARGRELEKPKAFPGHSMALQMMG
 Phatr_AMT3  (212) GVVHMTGGVTALFATLILGPRRGRFHDETGRRLDKPKSFPGHSVALQMLG
 Phatr_AMT7  (206) GVVHVTGGITALFATMVLGPRRGRFHDDLGHDLARPREFQAHSPALQMLG
 Phatr_AMT5  (219) GVVHVTGGVTALFATIILGPRRGRFHDQDGQRLIRPRIFPGHSFALQMLG
 Thaps_AMT3  (206) SVVHLTGGCIALIATYILGPRRGRFYDHRGEPLETPVEFPGHSAALQMLG
 Thaps_AMT4  (209) TVVHLTGGFTALIATYLLGPRRGRFYDAKGKQLEVPNPMPGHSAALQMLG
 Thaps_AMT6  (216) TVVHLTGGMTALIATIVLGPRTGRFYDLRGNPLKVPKEFAGHSLALQMLG
 Consensus   (251) GVVHMTGGVTALVATIILGPRRGRFYD DGN LE PKSFPGHSVALQMLG
 PS01219           GVVHMTGGVTALVATIILGPR
 CD (cont'd)       XXXXXXXXXXXXXXXXXXXXXXXXXXXXXXXXXXXXXXXXXXXXXXXXXX
```

FIGURE 3 (continued)

```
                    301                                              350
 Phatr_AMT1   (258) TFILWFGWYGFNPGSALKIANAD-SAATAALCAVTTTMAAAAGCVSAMFT
 Cylfu_AMT1   (260) TFLLWFGWYGFNPGSALVIDNAA-SASTSALCAVTTTLAAASGCVCAMFT
Cylfu_AMT2a   (260) TFLLWFGWYGFNPGSALVIDNAA-SASTSALCAVTTTLAAASGCVTAMFT
 Thaps_AMT1   (260) TFILWVGWYGFNPGSTLLISNTA-AADVSALCAVTTTIAAASGSVSAMFT
 Phatr_AMT2   (256) TFCLWFGWYGFNPGSVFFISSIE-NGQVAALVAVNTTLAACAGAVSAMFT
 Thaps_AMT2   (252) TFALWFGWYGFNPGSSILIASAA-SGDVASLAAVNTTLGSAAGALSGMFT
 Phatr_AMT4   (267) TFVLWFGWYGFNPGSALLLAHTSDTGFVASRAAVNTSLSAASGAVSALMT
 Phatr_AMT6   (256) TMILWFGWYGFNPGSALLLTATSNTGGVAALAAVNTSLSAASGAVSALFT
 Phatr_AMT3   (262) TFILWFGWYGFNCGSALLIDKPG-ANDIAALAGVNTTLSAGVAGIVALFV
 Phatr_AMT7   (256) TFILWFGFYGFNIGSALISTKQG-SDEAAALAGVNTTLSASAAGIVALFS
 Phatr_AMT5   (269) TLILWFGWYGFNIGAALLLDVPS-SDNIAALAAVNTTLSGGTAGIVALFF
 Thaps_AMT3   (256) AFILWFGWYGFNTGSTLSITGPG-QHQVVSLVAVNTTLAAASACVASLLA
 Thaps_AMT4   (259) IFILWFGWYGFIVGSAITIIGPN-QDKIISTSAVNTTLSAASSCFSALLV
 Thaps_AMT6   (266) VFILWFGWYGFNAGSILNITNDL-NHTIVSHTAINTTLAASAGSIMTLFL
 Consensus    (301) TFILWFGWYGFNPGSALLI   A SA VAALAAVNTTLAAASGAVSALFT
 CD (cont'd)        XXXXXXXXXXXXXXXXXXXXXXXXXXXXXXXXXXXXXXXXXXXXXXXXXX

                    351                                              400
 Phatr_AMT1   (307) DSIIDGMATGETTYDLTMAMNGCLAGLVAVTAGTSVVTPWAAIIIGVVGG
 Cylfu_AMT1   (309) DTIIEMMATGEASYDLTMAMNGALGGLVAITAGCSVVTPWASIIIGIIAG
Cylfu_AMT2a   (309) DTLIEMMATGEASYDLTMAMNGALAGLVAITAGCSVVTPWASLIIGIIGG
 Thaps_AMT1   (309) DMFLERRKTGETMYDITMCMNGALSGLVGITAGCSIVEPWAAFVIGIVAG
 Phatr_AMT2   (305) STLFDYWYTGLHTYDLGYTMNGCLTGLVAITAGCATVETWAAVLIGIGAG
 Thaps_AMT2   (301) STIVDERKTGVYTWDTTAAMNGCLTGLVAITAGCATVEPWAAFVIGLTAG
 Phatr_AMT4   (317) NMFMEERSTGEYSFNIIMAMNGALAGLVSITAACGTVQNWAALCTGCIGG
 Phatr_AMT6   (306) SLYLEERKTGFYSFNITMAMNGALAGLVGITAGCGTVENWAACCTGLVSG
 Phatr_AMT3   (311) NLWYLERTTGEPFFDLTYAMNGSLSGLVAITGGCAVLEPWAAAVTGVGAG
 Phatr_AMT7   (305) NLWYLEKTTGEPLFDLKYAMNGAICGLVAISGGCGVFEPWAAVVTGAVAG
 Phatr_AMT5   (318) NLWYLDKRTGEAYFDLKFAMNGCLCGLVAITGGCGVVEPWAAVVIGFVAG
 Thaps_AMT3   (305) SYYVIERKTGEGTFSLSSAMNGCLGGLVSITGGCAVVEPWAAVVIGFIAG
 Thaps_AMT4   (308) NYVIVERQSGEGEFSLLAAMNGCLSGLVAITGGCAVIAPWAAIIVGLFAG
 Thaps_AMT6   (315) STVVAERFTGEIVFSLSYAMNGCLSGLVAITAGCSVVEHWAAIIIGLVGG
 Consensus    (351)   WIEER TGE SFDLT AMNGCLAGLVAITAGCAVVEPWAAIVIGIVAG
 CD (cont'd)        XXXXXXXXXXXXXXXXXXXXXXXXXXXXXXXXXXXXXXXXXXXXXXXXXX

                    401                                              450
 Phatr_AMT1   (357) WVYIGMSKLLIKLKIDDAVDAIPVHFANGFWGVLATGLFANGGLMATAGY
 Cylfu_AMT1   (359) WVYIAFSKLLVKLKIDDAVDAVPVHFANGMWGVLAVGFFAEPDAMVTAGY
Cylfu_AMT2a   (359) WVYLGLSKLLIKLKIDDAVDAVPVHFGNGMWGVLAVGFFAEPDAMVTAGY
 Thaps_AMT1   (359) WTYIFWSSLLVKLKIDDAVDAIPVHFGNGMWGCIAVGLFAEPTRVANAYS
 Phatr_AMT2   (355) WFYLLGSKLLVYFRIDDAVDAIPVHMVGGAWGVIATGLFTKGELLLAAFG
 Thaps_AMT2   (351) WVYLAASAIMLRFKIDDAVDAIPVHMFGGSWGVFCTGLFTSPRRLITAYG
 Phatr_AMT4   (367) LIYLWGSKTLVRLKLDDAVDAIPVHMFAGGWGLLAVGLLSDPDLMHIAYG
 Phatr_AMT6   (356) WVYIFGSAFLLRIKIDDAVDAIPVHMFCGAWGLIATGLFSSPRHTLEAFG
 Phatr_AMT3   (361) ILYMVGSRGLVMLRLDDAVDAIPVHFVNGAWGLMSVGLFASPARLLAAYD
 Phatr_AMT7   (355) VIYLLGSRGLVSMRLDDAVDAIPVHLCGGAWGILAVGLFAAPERLLSVYG
 Phatr_AMT5   (368) LLYNIGSRGLIYLRLDDAVDAIPVHLCNGSWGLVAVGLFASPSRLLVIYG
 Thaps_AMT3   (355) LLYLFTSKLLIRLRIDDAVDAIPVHLSNGIWGTVAVGLFASSNRLQLAFG
 Thaps_AMT4   (358) LLYLFTSKVLVRVRIDDAVEAIPVHMTNGIWGSFAVGLFAAPSELQLVYG
 Thaps_AMT6   (365) ALYLACSKFLVKKRIDDAVDGIPVHLINGIWGTLSVGLFAVPELLEQVYG
 Consensus    (401) WLYL GSKLLVKLKIDDAVDAIPVHM NG WGVLAVGLFASP  LL AYG
 CD (cont'd)        XXXXXXXXXXXXXXXXXXXXXXXXXXXXXXXXXXXXXXXXXXXXXXXXXX
```

FIGURE 3 (continued)

```
                  451                                              500
 Phatr_AMT1  (407) NSEHEGWFYEWGSGSGDGSLLICQLACLAWIIGWVTTIMTPFFILLNMAG
 Cylfu_AMT1  (409) N-DVPGVFYKG-----DGKLLLCQFVAIIWICAWIFFLMTPFFVVLNILG
Cylfu_AMT2a  (409) N-DVPGVFYKG-----DGSLLLCQFVAIVWVCAWVFFLMTPFFVVLNILG
 Thaps_AMT1  (409) DHGHYGWFYSWGAGNADAHLLAAQVCGVLWIIGWVSVIMIPYFILLNVLG
 Phatr_AMT2  (405) QEEHVGWFYEWGSGSGNFTLIGIQLLSVLFIFAWTFSVMGIYFYALSFMG
 Thaps_AMT2  (401) NDNNVGWFYEWGRGSGNFTLLGCQLVSILFVLGWSACIFAPFCLALKTLN
 Phatr_AMT4  (417) TGNHPGLLYSWGLGEFNAILLSNQVLELVFVAGWAFGTMTPFFLFINRMG
 Phatr_AMT6  (406) TDAHVGWFYSLGQDSLDAILLMNQLLGLLFILGWSAILMSPFFWWLNYMG
 Phatr_AMT3  (411) NDAHPGWFYSLRNGKSDGRLVGVQLVGIVFIVGWVMVIMLPFFIWLDWKG
 Phatr_AMT7  (405) RNNHPGLVYSIREGDIDGVLFGIQLIGLMFIMGWVMIIMLPFFVWLNWKG
 Phatr_AMT5  (418) HSDHPGWFYSLRDGESDFRLLASQLVGLIFIVFWVMFNMLPFFVWLNYRG
 Thaps_AMT3  (405) KVADTGVFMG-----GTGKLLGCQIIGVFFVLGWISFIMIPFFCFLHYMG
 Thaps_AMT4  (408) KANHVGLFYSWHQGSGDGTLLGVQCLGILFVVGWVFCLMSPFFLFLNYKG
 Thaps_AMT6  (415) RGDHAGWFYSWGQGSADAKLLGAQVVGILFVSGWVMITMFPFFCFLHYVG
 Consensus   (451)    H GWFYSWG G GDG LLG QLVGILFILGWV  IM PFFVFLNYLG
 CD (cont'd)       XXXXXXXXXXXXXXXXXXXXXXXXXXXXXXXXXXXXXXXXXXXXXXXXXX

                  501                                              550
 Phatr_AMT1  (457) MFRVDPLEEEVGLDISHHRGSAYDLS------GPSKDHVDELMEIRAS--
 Cylfu_AMT1  (453) MFRVDPLEEEVGLDISHHRGAAYDMT------SAKKEDVEELMEHRSS--
Cylfu_AMT2a  (453) MFRVDPLEEEVGLDISHHRGSAYDMT------TAKKEDVEELMEHRSS--
 Thaps_AMT1  (459) LFRVDALEEEVGLDISHHKGAAYDMS------GPSEAAAEKFEISRS---
 Phatr_AMT2  (455) WLRIDPLEEEVGMDISRHKGSAYDMT------SANMEQVRSLMDDRSTSN
 Thaps_AMT2  (451) WLRIDPLEEEVGMDISRHKGPAYESEG-----SAHSDAIEKLSASRRDIM
 Phatr_AMT4  (467) WFRSDSLEELVGLDEAYHGGKHGGE------EVVELSALEGFIKNKIRQS
 Phatr_AMT6  (456) WLRADSLEELVGLDQAYHGGREAGEG---FDDEVPFATSKDKPDTLRRRK
 Phatr_AMT3  (461) WFRSDPLEEIVGLDTSYHGGLALLGG----DDEVNPEYISAYKKQRNE--
 Phatr_AMT7  (455) WFRSDPLEEIIGLDLSYHVGLALHT------NNVHPEYVGSEKDVVDEI-
 Phatr_AMT5  (468) WFRSDPLEELVGLDLSYHGGLMLHE-------EVDPEYISAYRKGQHEA-
 Thaps_AMT3  (450) WLRSESIDEVEGLDSKYHGLRNKDEHRHDEEEDNTPSHYGEGNCRLRR--
 Thaps_AMT4  (458) WFRADVLNEIAGLDLSYHDGVDMELVTQIRNQRKN-LHVNSRNRFSSN--
 Thaps_AMT6  (465) WLRADSLEEVVGLDAAYSQGVLQTRARAQSEEENMEHYISEYVKQREEKA
 Consensus   (501) WFRSDPLEEIVGLDISYH G A D            EYV      R
 CD (end)          XXXXXXXXXXXXXX

                  551                                              600
 Phatr_AMT1  (499) ---------KHGKVEVPKEVAQAADDAAEETA------------------
 Cylfu_AMT1  (495) ---------KHGKVEVPKEVQKEDTA------------------------
Cylfu_AMT2a  (495) ---------KHGKVEIPKEVQKEDTA------------------------
 Thaps_AMT1  (500) ----------QRKLEIPVDVAPATAPAEDAA-------------------
 Phatr_AMT2  (499) ----RGKLRKSSIIEKPAKTGPIEGGTASGESEIKESDVEHAERV-----
 Thaps_AMT2  (496) ----NASG--SGRGKSFSRSTPTKANEEPKIEATEDAGAPAGEATA----
 Phatr_AMT4  (511) -----QIRSPYN--------------------------------------
 Phatr_AMT6  (503) -----GGNSAEGTRDDGSWTDLTASAPRETAPLPELYCENDASSKESDDD
 Phatr_AMT3  (505) --------GTLRRRHKGTTSSVKTGEVESDEGAERVAPEATKHKKIPIAT
 Phatr_AMT7  (498) -------ISTRQRKVNGSTTTKATSGTEELEYIPEVSDEDLSEMKEECL-
 Phatr_AMT5  (510) -------HSRTLRQRK-RTSHVRLESVSEHSVAPNGGDSAHTSNGDSLTE
 Thaps_AMT3  (498) -----SILRHEERMRQEDSAIPATLVSSDDRFTCDSGGNSTSMLSTAKQY
 Thaps_AMT4  (505) -----SACPHHT--------------------------------------
 Thaps_AMT6  (515) FIKKINSNSTHGRTILGASMHSMNIINSSMHSRKDSLPRAIESLNNSRHS
  Consensus  (551)             R
```

FIGURE 3 (continued)

```
                      601                            632
  Phatr_AMT1   (522)  --------------------------------
  Cylfu_AMT1   (512)  --------------------------------
 Cylfu_AMT2a   (512)  --------------------------------
  Thaps_AMT1   (521)  --------------------------------
  Phatr_AMT2   (540)  --------------------------------
  Thaps_AMT2   (536)  --------------------------------
  Phatr_AMT4   (518)  --------------------------------
  Phatr_AMT6   (548)  PSGMHHA-------------------------
  Phatr_AMT3   (547)  TTEVFNGGQDTDQMSYHA--------------
  Phatr_AMT7   (540)  --------------------------------
  Phatr_AMT5   (552)  TVTIREPDSGWPRGNV----------------
  Thaps_AMT3   (543)  T-------------------------------
  Thaps_AMT4   (512)  --------------------------------
  Thaps_AMT6   (565)  GSRGSRSINDIAIDNLHGQSEDGFAAPDEGSA
   Consensus   (601)
```

SEQ ID NO: 1 Phaeodactylum tricornutum Phatr_AMT1 full length nucleic acid sequence

ATGTCTTTTGATTTGGACGCATTCTGCACTGGCCTGACAGCCGCGTCGAGCTCTTCTGAGCAGGCT
GTGTGCGCTCTGCAAACGATCGTGGCCGGAGTTTCTAAGACTGTCGGAGGTATTGACGCGGAAGGG
ATTACTGCAGGTGTTGATACTTTCTTCCTCATTTTTGCGGGTGCCTTGGTCTTCATGATGCAGGCC
GGGTTCGCCATGCTTTGTGCTGGATCCGTCCGTCAAAAGAATGTAAAGAATATTATGCTCAAGAAC
TTGTTGGATGCCTGTGGTGGTGCTATTGGCTTCTACACCGTTGGTTTCGGCTTCGCTTATGGCGGT
GACGACACCACCGACAAGACCTTCATTGGCAACAGCTACTTCGCGCTCCGTGATTACACAAATTAT
GCAGGTTTCTTCTTCCAGTTTGCGTTTGCTGCCACTGCCGCCACGATTGTTGCCGGTACAGTTGCT
GAGCGATGCAAGATGTCGGCATACCTTTGCTACTCTCTCTTTCTTACGGGTTTCGTCTATCCCGTC
GTTGTACGCTCTGTCTGGAGCTCCAACGGGTTCTTGTCAGCCTTCAGTGCCGACCCCTTCCAAGGA
GTTGGAACCGTTGACTTTGCCGGATCAGGTGTGGTGCACATGACTGGAGGACTCACCGCCTTGATT
GCTGCCATTGTTCTTGGACCGCGTAAGGGTCGGTTCTACGATGAGGATGGCAACCCTCTGGAGACG
CCCGCCAGCTTCCCAGCCCACTCTGTAGCCCTCCAGATCCTCGGAACTTTCATCTTGTGGTTCGGA
TGGTACGGATTCAACCCTGGTTCAGCCCTGAAGATTGCTAACGCCGATTCGGCCGCAACCGCCGCT
TTGTGTGCCGTCACCACCACTATGGCCGCCGCTGCCGGTTGTGTTTCCGCCATGTTCACTGACTCG
ATCATTGACGGCATGGCGACCGGTGAAACTACGTACGATCTGACCATGGCCATGAATGGATGCCTT
GCTGGTCTCGTTGCCGTCACTGCTGGTACATCTGTCGTCACCCCATGGGCCGCAATCATTATTGGA
GTCGTTGGAGGTTGGGTCTACATTGGTATGTCCAAGCTTTTGATCAAGCTCAAGATTGATGACGCT
GTCGATGCCATCCCTGTCCATTTCGCCAATGGTTTCTGGGGTGTCCTAGCCACCGGCCTTTTCGCC
AACGGTGGATTGATGGCAACCGCTGGGTACAACTCGGAACACGAGGGCTGGTTCTACGAATGGGGA
AGTGGCTCCGGAGATGGAAGTCTTCTCATCTGCCAGCTTGCTTGCCTCGCCTGGATTATTGGATGG
GTCACCACCATTATGACGCCCTTTTTTATCCTTTTGAACATGGCCGGTATGTTCCGTGTGGACCCG
CTTGAGGAAGAAGTTGGTCTTGATATTTCCCATCACCGTGGATCTGCTTACGATCTTTCGGGACCC
AGCAAGGACCATGTTGACGAGCTCATGGAAATTCGTGCCTCGAAGCACGGCAAGGTTGAGGTTCCA
AAGGAGGTTGCGCAGGCTGCTGATGACGCCGCCGAAGAGACTGCTTAA

SEQ ID NO: 2 Phaeodactylum tricornutum Phatr_AMT1 full translated polypeptide sequence

MSFDLDAFCTGLTAASSSSEQAVCALQTIVAGVSKTVGGIDAEGITAGVDTFFLIFAGALVFMMQA
GFAMLCAGSVRQKNVKNIMLKNLLDACGGAIGFYTVGFGFAYGGDDTTDKTFIGNSYFALRDYTNY
AGFFFQFAFAATAATIVAGTVAERCKMSAYLCYSLFLTGFVYPVVVRSVWSSNGFLSAFSADPFQG
VGTVDFAGSGVVHMTGGLTALIAAIVLGPRKGRFYDEDGNPLETPASFPAHSVALQILGTFILWFG
WYGFNPGSALKIANADSAATAALCAVTTTMAAAAGCVSAMFTDSIIDGMATGETTYDLTMAMNGCL
AGLVAVTAGTSVVTPWAAIIIGVVGGWVYIGMSKLLIKLKIDDAVDAIPVHFANGFWGVLATGLFA
NGGLMATAGYNSEHEGWFYEWGSGSGDGSLLICQLACLAWIIGWVTTIMTPFFILLNMAGMFRVDP
LEEEVGLDISHHRGSAYDLSGPSKDHVDELMEIRASKHGKVEVPKEVAQAADDAAEETA

SEQ ID NO: 3 Phaeodactylum tricornutum Phatr_AMT1 partial nucleic acid sequence

ATGATGCAGGCCGGGTTCGCCATGCTTTGTGCTGGATCCGTCCGTCAAAAGAATGTAAAGAATATT
ATGCTCAAGAACTTGTTGGATGCCTGTGGTGGTGCTATTGGCTTCTACACCGTTGGTTTCGGCTTC
GCTTATGGCGGTGACGACACCAGCGACAAGACCTTCATTGGCAACAGCTACTTCGCGCTCCGTGAT
TACACAAATTATGCAGGTTTCTTCTTCCAGTTTGCGTTTGCTGCCACTGCCGCCACGATTGTTGCC
GGTACAGTTGCTGAGCGATGCAAGATGTCGGCATACCTTTGCTACTCTCTCTTTCTTACGGGTTTC
GTCTATCCCGTCGTTGTACGCTCTGTCTGGAGCTCCAACGGGTTCTTGTCAGCCTTCAGTGCCGAC
CCCTTCCAAGGAGTTGGAACCGTTGACTTTGCCGGATCAGGTGTGGTGCACATGACTGGAGGACTC
ACCGCCTTGATTGCTGCCATTGTTCTTGGACCGCGTAAGGGTCGGTTCTACGATGAGGATGGCAAC
CCCCTGGAGACGCCCGCCAGCTTCCCAGCCCACTCTGTAGCCCTCCAGATCCTCGGAACTTTCATC
TTGTGGTTCGGATGGTACGGATTCAACCCTGGTTCAGCCCTGAAGATTGCTAACGCCGATTCGGCC

FIGURE 5

ACAACCGCCGCTTTGTGTGCCGTCACCACCACTATGGCCGCCGCTGCCGGTTGTGTTTCCGCCATG
TTCACTGACTCGATCATTGACGGCATGGCGACCGGTGAAACTACGTACGATCTGACCATGGCCATG
AATGGATGCCTTGCTGGTCTCGTTGCCGTCACTGCTGGTACATCTGTCGTCACCCCATGGGCCGCA
ATCATTATTGGAGTCATTGGAGGTTGGGTCTACATTGGTATGTCCAAGCTTTTGATAAAGCTCAAG
ATTGATGACGCTGTCGATGCCATCCCTGTCCATTTCGCCAACGGTTTCTGGGGTGTCCTAGCCACC
GGCCTTTTCGCCAACGGTGGATTGATGGCAACCGCTGGGTACAACTCGGAACACGAGGGCTGGTTC
TACGAATGGGGAAGTGGCTCCGGAGATGGAAGTCTTCTCATCTGCCAGCTTGCTTGCCTCGCCTGG
ATTATTGGATGGGTCACCACCATTATGACGCCCTTTTTTATCCTTTTGAACATGGCCGGTATGTTC
CGTGTGGACCCGCTTGAGGAAGAAGTTGGTCTTGATATTTCCCATCACCGTGGATCTGCTTACGAT
CTTTCGGGACCCAGCAAGGACCATGTTGACGAGCTCATGGAAATTCGTGCCTCGAAGCACGGCAAG
GTTGAGGTTCCAAAGGAGGTTGCGCAGGCTGCTGATGACGCCGCCGAAGAGACTGCTTAA

SEQ ID NO: 4 Phaeodactylum tricornutum Phatr_AMT1 partial polypeptide sequence

MMQAGFAMLCAGSVRQKNVKNIMLKNLLDACGGAIGFYTVGFGFAYGGDDTSDKTFIGNSYFALRD
YTNYAGFFFQFAFAATAATIVAGTVAERCKMSAYLCYSLFLTGFVYPVVVRSVWSSNGFLSAFSAD
PFQGVGTVDFAGSGVVHMTGGLTALIAAIVLGPRKGRFYDEDGNPLETPASFPAHSVALQILGTFI
LWFGWYGFNPGSALKIANADSATTAALCAVTTTMAAAAGCVSAMFTDSIIDGMATGETTYDLTMAM
NGCLAGLVAVTAGTSVVTPWAAIIIGVIGGWVYIGMSKLLIKLKIDDAVDAIPVHFANGFWGVLAT
GLFANGGLMATAGYNSEHEGWFYEWGSGSGDGSLLICQLACLAWIIGWVTTIMTPFFILLNMAGMF
RVDPLEEEVGLDISHHRGSAYDLSGPSKDHVDELMEIRASKHGKVEVPKEVAQAADDAAEETA

SEQ ID NO: 5 Phaeodactylum tricornutum Phatr_AMT2 nucleic acid sequence

ATGTCGAGTAGTGCTATCTATCAATCTTGCGCCGGTCAATTCGATAGCGGTGAGCAGCTTGATCAG
CTTCTGCAGTGCCTCTCTACGGGACATGACGGCGCGCTAAGCGATCAGACCAGCAACCTCGCAGGA
GGTATCGATGCCTTTTATCTTATCTTTGCCGGGGCCCTTGTCTACTTCATGCAGACAGGATTTGCT
ATGCTCTGTGCCGGATCCATTCGAGCGAAGAATGTCAAGAATGTGATTCTCTGGAACTTGCTCGAT
TCATGTGGAGGCGGTCTCGCGTTCTGGAGTGTAGGCTATGCCTTTGCCTACGGTGGAGACAATGCT
GGGTCCAAGACATTTGTTGGTAACGCAGGCTTTTTCCTCCAGGGAGATGACATTCGACTGGAAAAC
TGGTTTTTCCAATTTGCCTTTGCTTGTGCCCTTTCCTCAATTGTCGCTGGAACGATCGCTGAGCGC
ACTCAAATGAAGGCCTATTTGATGTATTCCGTTTTTTTGGCTGGGTTTGTCTATCCAGTTGTCGCC
CACGCATTTTGGTCGAGCAACGGATTCCTCTCCAACACAGCCACAGATCCATTGTGGGGATCTGGC
GCCATTGACTTGGCGGGCTCTGGACCAGTCCACATGACCGGAGGTGTTACGGCTTTGGCGGCAGCT
CTGGTTTTGGGCCCTCGCATTGGTCGCTTCTACGACAAGGAGGGCAATCCTCTCGAAGAGCCAGCC
GAATTTCCTCCCCATTCGGTTGCCTTGCAGTTTCTGGGAACGTTTTGTCTTTGGTTTGGCTGGTAC
GGCTTTAACCCAGGTTCCGTCTTCTTCATTTCGAGTATTGAAAACGGTCAAGTTGCGGCTTTGGTA
GCCGTCAATACCACCCTAGCTGCGTGTGCGGGTGCCGTCAGCGCCATGTTTACTTCAACTTTATTT
GACTACTGGTACACCGGCTTGCACACATACGATTTGGGCTACACTATGAACGGATGTTTGACGGGA
TTGGTCGCGATAACAGCGGGATGCGCGACTGTTGAAACGTGGGCTGCCGTCCTGATTGGTATTGGC
GCTGGTTGGTTTTACCTGTTGGGTTCAAAGTTGCTTGTCTACTTCCGTATTGACGATGCTGTCGAC
GCCATTCCCGTGCATATGGTGGGTGGCGCCTGGGGTGTGATCGCGACGGGCCTTTTTACGAAGGGA
GAACTACTATTGGCCGCCTTTGGCCAGGAGGAACATGTTGGATGGTTCTACGAGTGGGGCAGTGGG
AGCGGTAACTTTACCCTAATCGGAATTCAATTGCTGTCTGTGCTGTTCATTTTCGCCTGGACTTTT
TCCGTCATGGGAATTTATTTTTACGCCCTTAGCTTCATGGGTTGGTTGCGCATAGATCCGTTGGAA
GAGGAGGTTGGTATGGATATTTCGCGCCACAAGGGCTCGGCATACGACATGACTTCAGCAAATATG
GAGCAGGTACGGTCGTTGATGGACGACCGCAGTACGAGCAATCGAGGCAAGCTGCGTAAGTCGTCC
ATCATTGAGAAGCCGGCCAAAACAGGTCCGATCGAGGGAGGAACTGCCTCCGGAGAATCAGAAATT
AAGGAGTCGGACGTGGAACATGCCGAGAGGGTCTAA

FIGURE 5 (continued)

SEQ ID NO: 6 Phaeodactylum tricornutum Phatr_AMT2 translated polypeptide sequence

MSSSAIYQSCAGQFDSGEQLDQLLQCLSTGHDGALSDQTSNLAGGIDAFYLIFAGALVYFMQTGFA
MLCAGSIRAKNVKNVILWNLLDSCGGGLAFWSVGYAFAYGGDNAGSKTFVGNAGFFLQGDDIRLEN
WFFQFAFACALSSIVAGTIAERTQMKAYLMYSVFLAGFVYPVVAHAFWSSNGFLSNTATDPLWGSG
AIDLAGSGPVHMTGGVTALAAALVLGPRIGRFYDKEGNPLEEPAEFPPHSVALQFLGTFCLWFGWY
GFNPGSVFFISSIENGQVAALVAVNTTLAACAGAVSAMFTSTLFDYWYTGLHTYDLGYTMNGCLTG
LVAITAGCATVETWAAVLIGIGAGWFYLLGSKLLVYFRIDDAVDAIPVHMVGGAWGVIATGLFTKG
ELLLAAFGQEEHVGWFYEWGSGSGNFTLIGIQLLSVLFIFAWTFSVMGIYFYALSFMGWLRIDPLE
EEVGMDISRHKGSAYDMTSANMEQVRSLMDDRSTSNRGKLRKSSIIEKPAKTGPIEGGTASGESEI
KESDVEHAERV

SEQ ID NO: 7 Phaeodactylum tricornutum Phatr_AMT3 nucleic acid sequence

ATGAATAGCCGTACCTTTTCTTACAACAGCAACGATGGGAATGAGTTGTTGGATGCATGCATGGCT
TATCTCGGCGCTAACGCCACGACGTACGACTTGCTCGGCTGCGTGTCTGCGCAACTCAGCAACGAA
GTCGGGAGTCGCGAATTCTCTCGTTCGGTGCTGCTCGTCTACGCTGCTGCACTCGTATTCTTTATG
CAAGCCGGCTTCGCCATGCTCTGTGCCGGAGCCGTCCGGAAAAAGAACGTGCAGAACACCATGCTC
AAGAACTTGTTGGACGCCTGTGGAGCCGCCGTCGCCTTTTTCATCGTGGGCTACGCTATAGCCTTT
GGAGGCATGGAACCGGAATCGCCCAACAAGACATTTCTCGGGAACACCAATTTCTTTTTAATGGGA
GTGGACGATTTGGCCTTTTGGTTGTTCCAGTACGCCTTTTCCGCTGCCTCTGCAACCATCGTCGCG
GGAACTTTGGCCGAGCGCTGCCAAATGGTTGCCTACTTGTGTTACTCCGTAATGTTGACGGGATGG
GTCTATCCGATTATCGCGCACGCGATTTGGTCACCCAACGGTTGGCTCTCCGCCAGTTCCGTGGAT
CCGCTATGGGGTGTCGGCATGGTCGATTTCGCCGGCTCGGGAGTAGTGCACATGACTGGAGGCGTT
ACCGCCTTGTTCGCCACTCTCATACTCGGACCTCGCCGTGGACGGTTTCACGATGAAACCGGACGC
CGGCTCGACAAACCAAAATCCTTTCCCGGACACTCCGTGGCCTTGCAGATGCTCGGTACCTTCATT
CTCTGGTTTGGTTGGTATGGATTCAATTGCGGTTCGGCGTTACTCATCGACAAGCCCGGTGCTAAC
GATATTGCCGCCTTGGCGGGCGTCAATACGACACTTTCTGCCGGAGTCGCTGGGATAGTTGCACTC
TTTGTCAACCTCTGGTACCTCGAGCGAACAACCGGAGAACCTTTTTTTGATTTGACCTACGCCATG
AACGGATCCCTTTCGGGTCTCGTGGCCATCACAGGAGGTTGCGCTGTTCTCGAGCCCTGGGCGGCA
GCGGTCACTGGAGTCGGTGCCGGTATCTTGTACATGGTTGGATCACGAGGTTTGGTCATGTTGCGA
TTGGATGACGCGGTTGACGCGATTCCCGTTCATTTTGTGAACGGGGCCTGGGGTCTCATGTCGGTC
GGATTGTTCGCGTCACCAGCACGCTTGCTGGCCGCGTACGACAACGACGCTCATCCTGGATGGTTC
TATTCCCTACGAAACGGCAAATCGGACGGGCGTTTGGTTGGAGTTCAGCTGGTAGGCATTGTATTT
ATCGTGGGATGGGTCATGGTGATTATGTTGCCCTTCTTCATTTGGTTGGATTGGAAGGGATGGTTC
CGGTCGGATCCTTTGGAAGAAATTGTGGGATTGGACACGTCGTACCACGGTGGTCTCGCTTTGCTG
GGCGGGGACGATGAAGTCAACCCTGAGTACATTTCCGCGTACAAGAAGCAAAGGAACGAAGGTACG
CTGCGGCGTAGGCATAAAGGGACAACCAGCAGTGTCAAGACGGGAGAAGTAGAATCGGACGAAGGC
GCCGAACGGGTGGCGCCCGAAGCGACGAAGCACAAAAAGATTCCGATCGCTACAACGACAGAGGTT
TTCAATGGAGGTCAAGATACGGATCAAATGTCCTACCACGCCTGA

SEQ ID NO: 8 Phaeodactylum tricornutum Phatr_AMT3 translated polypeptide sequence

MNSRTFSYNSNDGNELLDACMAYLGANATTYDLLGCVSAQLSNEVGSREFSRSVLLVYAAALVFFM
QAGFAMLCAGAVRKKNVQNTMLKNLLDACGAAVAFFIVGYAIAFGGMEPESPNKTFLGNTNFFLMG
VDDLAFWLFQYAFSAASATIVAGTLAERCQMVAYLCYSVMLTGWVYPIIAHAIWSPNGWLSASSVD
PLWGVGMVDFAGSGVVHMTGGVTALFATLILGPRRGRFHDETGRRLDKPKSFPGHSVALQMLGTFI
LWFGWYGFNCGSALLIDKPGANDIAALAGVNTTLSAGVAGIVALFVNLWYLERTTGEPFFDLTYAM
NGSLSGLVAITGGCAVLEPWAAAVTGVGAGILYMVGSRGLVMLRLDDAVDAIPVHFVNGAWGLMSV

FIGURE 5 (continued)

GLFASPARLLAAYDNDAHPGWFYSLRNGKSDGRLVGVQLVGIVFIVGWVMVIMLPFFIWLDWKGWF
RSDPLEEIVGLDTSYHGGLALLGGDDEVNPEYISAYKKQRNEGTLRRRHKGTTSSVKTGEVESDEG
AERVAPEATKHKKIPIATTTEVFNGGQDTDQMSYHA

SEQ ID NO: 9 Phaeodactylum tricornutum Phatr_AMT4 nucleic acid sequence

ATGGACGACGCGAGCTTTATCCAAAGCCTGGTGGAAGGGTACGGTACCTCGAGCAACCACACCACC
GTCTATGGATATTGCTCCAATGAGGCGGAAGGAGAGACCAACCTTATTTTGCAATGTATTACGGAG
GTCATGGAGCAAAAGCAGCTCGAAGGAGATCGTAACGTGAATCGGTGGCTAATGCTTTTTTCCGGT
GGGCTGATCTTCTTCATGCAGACTGGCTTTGCGATGCTTTGCGCTGGTTGCGTGCGCAAAAAGAAC
GTTCAAAATACGATGCTTAAAAATCTTTTGGATGCCTGTGGAGCTGCTCTAGGCTTTTTCCTACTA
GGCTACGCTTTTGCGTTTGGCGGACAAGACGACCGGGACGATGTTACTTTCATCGGAACTTCCAAC
TTTCTAAACACCGGAAAAGTCGATATGTCCTTCTGGTTTTTCCAGTTTGCATTCTCGGCCACTGCC
GTGACTATCGTCGCAGGAACTTTGGCAGAGCGTTGCCAAATGGTAGCATACCTTTGCTATTCCATA
TTTTTGACAGGTTTTGTGTACCCGGTTGCCGCCCACACAATTTGGTCTCGCAACGGCTTCCTCAGC
AGCACAGCAGTAGACCCTTTTCAAGGTGTGGGAGCGATTGATTTCGCCGGATCCGGTGTGGTTCAT
GTGACGGGAGGAACCACGGCTCTCGTCGCCACATATATTCTTGGAGCTAGAAAAGGTCGTTTCTAC
GACAATCGCGGTCGCCAGCTGGAGACGCCAAAGTCCTTTCCGGGGCATTCAGTTGCTCTGCAGCTA
CTTGGTACATTCGTATTGTGGTTTGGATGGTACGGCTTCAATCCTGGATCAGCATTGCTGCTGGCC
CACACTTCGGATACGGGTTTCGTGGCATCCCGAGCGGCTGTCAATACCTCGCTTTCAGCTGCTTCC
GGAGCCGTATCGGCACTGATGACAAATATGTTTATGGAAGAGCGTTCCACCGGCGAATACTCCTTT
AACATTATCATGGCCATGAATGGCGCCTTAGCTGGTCTAGTGTCAATTACAGCAGCTTGTGGTACC
GTACAAAACTGGGCAGCCCTTTGCACTGGATGTATTGGAGGTCTTATCTACTTGTGGGGTTCCAAA
ACGCTGGTTCGTTTGAAATTGGACGATGCTGTTGACGCGATTCCAGTGCACATGTTTGCAGGTGGC
TGGGGATTGCTTGCTGTGGGTTTGTTAAGTGATCCTGACCTCATGCACATTGCCTATGGGACTGGC
AATCATCCTGGTTTATTGTATTCTTGGGGGTTAGGGGAGTTTAACGCCATCTTGCTGAGCAATCAA
GTGTTGGAACTAGTTTTCGTGGCGGGATGGGCTTTTGGTACCATGACGCCTTTCTTTTTGTTCATC
AATCGTATGGGATGGTTCCGGTCGGACAGTTTGGAGGAGTTGGTCGGTTTGGATGAGGCCTACCAC
GGAGGTAAACATGGCGGGGAAGAAGTGGTGGAACTATCCGCTCTAGAAGGCTTTATCAAAAACAAG
ATCAGACAATCGCAAATTCGGTCGCCTTACAATTAG

SEQ ID NO: 10 Phaeodactylum tricornutum Phatr_AMT4 translated polypeptide sequence

MDDASFIQSLVEGYGTSSNHTTVYGYCSNEAEGETNLILQCITEVMEQKQLEGDRNVNRWLMLFSG
GLIFFMQTGFAMLCAGCVRKKNVQNTMLKNLLDACGAALGFFLLGYAFAFGGQDDRDDVTFIGTSN
FLNTGKVDMSFWFFQFAFSATAVTIVAGTLAERCQMVAYLCYSIFLTGFVYPVAAHTIWSRNGFLS
STAVDPFQGVGAIDFAGSGVVHVTGGTTALVATYILGARKGRFYDNRGRQLETPKSFPGHSVALQL
LGTFVLWFGWYGFNPGSALLLAHTSDTGFVASRAAVNTSLSAASGAVSALMTNMFMEERSTGEYSF
NIIMAMNGALAGLVSITAACGTVQNWAALCTGCIGGLIYLWGSKTLVRLKLDDAVDAIPVHMFAGG
WGLLAVGLLSDPDLMHIAYGTGNHPGLLYSWGLGEFNAILLSNQVLELVFVAGWAFGTMTPFFLFI
NRMGWFRSDSLEELVGLDEAYHGGKHGGEEVVELSALEGFIKNKIRQSQIRSPYN

SEQ ID NO: 11 Phaeodactylum tricornutum Phatr_AMT5 nucleic acid sequence

ATGAGTCACTCTAGTTTGGATGTGTTCGGGACCTGCCTTGCCCAAGTTGGCGAAGACGCAACGACA
AAGGAGCTACTAGAATGCGTTTCCTTTAGTTTGTCGCGAGCAGTGCCAGACGGTCTCGATGAGCCT
AGTTCTAAAGGCTTCACGCGGTCTATCGTTGTCGTGTTTGCGGCTGCCTTGGTTTTTTTCATGCAA
GCCGGCTTTGCCATGCTGTGCGCTGGAGCCGTTAGGGCCAAGAATGTTCAAAACACCATGCTCAAG
AATCTTTTGGATGCTTGTGGTGCCGCCATTGCGTTCTTTACTGTAGGCTACGCCTTTGCCTTTGGC

FIGURE 5 (continued)

GGTACGGACTTTCCCACCGACACCGACACCGACACCGGCAACAACCAAACAACATTCATTGGCACA
TCGAACTTTTTCTTGGTGAATGTGGACGATTATTCCTTTTGGCTGTTTCAATACGCATTTTCCGCC
GCGTCCGCAACCATTGTTGCTGGAACACTGGCTGAACGGTGTCAAATGGCCGCCTACCTGGGATAT
TCCGCTTTGTTAACGGGATGGGTGTACCCCATTGTCGCTCACGCTGTATGGAACGTCCACGGCTTC
CTATCGGCTCATGCGGTAGAACCTTTGTGGGGGGTTGGAATGGTAGATTTTGCCGGTTCTGGGGTC
GTTCACGTTACGGGAGGTGTGACAGCGCTCTTCGCGACAATAATTCTGGGTCCCCGCCGTGGACGC
TTTCACGACCAAGATGGCCAAAGATTGATAAGGCCGCGAATATTTCCTGGACACTCCTTTGCTCTG
CAAATGCTTGGAACCCTTATCTTATGGTTTGGCTGGTACGGATTCAATATTGGCGCTGCTCTGCTG
CTGGACGTGCCTAGTTCAGACAATATTGCAGCTCTGGCTGCGGTGAATACGACCTTGTCGGGCGGG
ACGGCTGGCATCGTTGCTCTCTTTTTCAATTTGTGGTATCTGGACAAAAGAACTGGCGAAGCCTAT
TTTGACTTGAAATTTGCCATGAATGGGTGCCTCTGCGGTCTCGTGGCCATCACTGGAGGCTGTGGT
GTGGTCGAACCCTGGGCTGCCGTTGTGATTGGCTTTGTCGCCGGTTTGTTGTACAACATCGGAAGT
CGCGGACTTATATATTTGCGTTTGGATGATGCCGTGGATGCCATTCCGGTACATTTGTGCAACGGC
TCGTGGGGTCTCGTAGCAGTAGGGCTGTTTGCCTCCCCCTCCCGGCTACTAGTTATTTACGGACAT
AGCGATCATCCAGGATGGTTTTACTCATTACGAGATGGCGAATCCGATTTCCGGTTACTGGCTTCC
CAGTTGGTGGGCCTTATTTTCATTGTCTTCTGGGTCATGTTCAACATGCTGCCTTTTTTCGTTTGG
TTAAACTACCGTGGCTGGTTTCGGTCCGATCCGTTGGAAGAGTTGGTGGGTCTCGACCTGAGCTAT
CACGGCGGTTTAATGCTGCACGAGGAAGTTGATCCCGAATACATATCGGCCTATCGCAAGGGCCAA
CACGAGGCTCATTCTCGTACTCTGCGACAACGGAAACGCACATCCCACGTGCGCTTGGAATCAGTG
AGCGAACATTCCGTTGCGCCAAATGGCGGAGACTCAGCCCATACTAGTAACGGCGATTCGCTCACG
GAAACGGTCACTATCCGTGAACCGGACTCCGGTTGGCCAAGGGGGAACGTATAA

SEQ ID NO: 12 Phaeodactylum tricornutum Phatr_AMT5 translated polypeptide sequence

MSHSSLDVFGTCLAQVGEDATTKELLECVSFSLSRAVPDGLDEPSSKGFTRSIVVVFAAALVFFMQ
AGFAMLCAGAVRAKNVQNTMLKNLLDACGAAIAFFTVGYAFAFGGTDFPTDTDTDTGNNQTTFIGT
SNFFLVNVDDYSFWLFQYAFSAASATIVAGTLAERCQMAAYLGYSALLTGWVYPIVAHAVWNVHGF
LSAHAVEPLWGVGMVDFAGSGVVHVTGGVTALFATIILGPRRGRFHDQDGQRLIRPRIFPGHSFAL
QMLGTLILWFGWYGFNIGAALLLDVPSSDNIAALAAVNTTLSGGTAGIVALFFNLWYLDKRTGEAY
FDLKFAMNGCLCGLVAITGGCGVVEPWAAVVIGFVAGLLYNIGSRGLIYLRLDDAVDAIPVHLCNG
SWGLVAVGLFASPSRLLVIYGHSDHPGWFYSLRDGESDFRLLASQLVGLIFIVFWVMFNMLPFFVW
LNYRGWFRSDPLEELVGLDLSYHGGLMLHEEVDPEYISAYRKGQHEAHSRTLRQRKRTSHVRLESV
SEHSVAPNGGDSAHTSNGDSLTETVTIREPDSGWPRGNV

SEQ ID NO: 13 Phaeodactylum tricornutum Phatr_AMT6 nucleic acid sequence

ATGAGCACATCCGATGGCAGTCTGTTTCAACAGTGTTCTGCCGTCGCTGGGGACAGTGACCCTTCC
CGGATTCTGCAGTGTGTGTCCGATGCTCTCGAAACCAACCAAAACGATCGAGCTGCCGATCTCAAT
AACTGGTTTCTCATCATCGCTGGGGCACTCGTCTTTTTCATGCAGTCCGGCTTCGCCATGCTGTGT
GCGGGGTGTGTGCGGAAAAAGAACGTCCAAAACACCATGCTCAAGAATCTTCTCGATGCCTGCGGT
GCCGCTCTCGGGTTTTACGTAATCGGTTACGCCTTGGCCTTTGGTGGACAAAACGAGCGATCCGAT
GTTACCTTTGTGGGTACCACGGACTTTTTCAACTGGAACAGCGCCGTCCCGGTAAATCAAGCCTTT
TGGTTTTTCGAATTTGCCTTTTCGGCCACGTCCGTGACGATTGTGGCCGGGACGCTGGCGGAACGG
TGTCAAATGGTCGCCTACCTGTGCTACTCGGTATTCTTAACAGGCTTTGTGTATCCCGTTGTGGCC
CACTCCATCTGGAGCAACAACGGCTTTCTAAGTGCATTTGCAGCCGAGCCCTTCCAGGGCATTGGC
GTCCTGGACTTTGCCGGGTCGGGTGTGGTACACGTGACGGGCGGGACCACTGCCTTGGTCGCCACG
TATATGCTAGGGGCCCGTAAGGGGCGCTTCTACGACGCACGTGGGAGAGAATTGGAAAAGCCCAAA
GCATTTCCCGGCCATTCCATGGCCTTGCAGATGATGGGCACCATGATTCTGTGGTTCGGATGGTAC
GGCTTCAACCCTGGTTCGGCCTTGTTGCTGACGGCGACGTCCAATACAGGTGGCGTAGCGGCTCTC

FIGURE 5 (continued)

GCGGCCGTGAACACGTCCCTCTCTGCCGCTTCGGGTGCCGTTTCCGCTCTCTTTACCTCTTTGTAT
CTCGAAGAACGCAAGACTGGAGAATACTCCTTCAACATCACCATGGCTATGAACGGTGCTTTGGCT
GGCTTAGTGGGTATTACGGCCGGCTGTGGCACCGTCGAAAATTGGGCCGCTTGTTGCACAGGGCTC
GTGTCTGGATGGGTCTATATATTTGGCAGTGCCTTCTTGTTGCGTATAAAGATTGACGATGCAGTC
GACGCAATTCCGGTGCATATGTTTTGTGGCGCCTGGGGTCTTATTGCAACCGGCCTATTCAGCTCG
CCACGCCATACGTTAGAAGCATTTGGTACGGACGCACACGTAGGTTGGTTCTACAGTCTTGGCCAA
GATTCTTTGGACGCTATTCTCTTGATGAACCAGCTTTTGGGTCTTTTATTTATTCTCGGGTGGAGC
GCCATCTTGATGTCACCATTTTTCTGGTGGCTGAACTACATGGGATGGTTGAGGGCCGACTCCTTG
GAGGAGTTGGTAGGTCTGGATCAAGCCTACCACGGTGGAAGGGAGGCTGGAGAGGGCTTTGATGAT
GAAGTGCCTTTTGCCACATCCAAAGACAAACCAGACACTTTACGTCGACGGAAAGGTGGCAACAGC
GCGGAGGGCACCCGCGATGATGGAAGTTGGACCGATTTGACTGCCTCGGCTCCTCGGGAAACTGCG
CCTCTGCCAGAACTTTATTGTGAGAACGATGCGTCTTCCAAAGAATCCGACGACGATCCGTCCGGA
ATGCACCACGCATAA

SEQ ID NO: 14 Phaeodactylum tricornutum Phatr_AMT6 translated polypeptide sequence

MSTSDGSLFQQCSAVAGDSDPSRILQCVSDALETNQNDRAADLNNWFLIIAGALVFFMQSGFAMLC
AGCVRKKNVQNTMLKNLLDACGAALGFYVIGYALAFGGQNERSDVTFVGTTDFFNWNSAVPVNQAF
WFFEFAFSATSVTIVAGTLAERCQMVAYLCYSVFLTGFVYPVVAHSIWSNNGFLSAFAAEPFQGIG
VLDFAGSGVVHVTGGTTALVATYMLGARKGRFYDARGRELEKPKAFPGHSMALQMMGTMILWFGWY
GFNPGSALLLTATSNTGGVAALAAVNTSLSAASGAVSALFTSLYLEERKTGEYSFNITMAMNGALA
GLVGITAGCGTVENWAACCTGLVSGWVYIFGSAFLLRIKIDDAVDAIPVHMFCGAWGLIATGLFSS
PRHTLEAFGTDAHVGWFYSLGQDSLDAILLMNQLLGLLFILGWSAILMSPFFWWLNYMGWLRADSL
EELVGLDQAYHGGREAGEGFDDEVPFATSKDKPDTLRRRKGGNSAEGTRDDGSWTDLTASAPRETA
PLPELYCENDASSKESDDDPSGMHHA

SEQ ID NO: 15 Phaeodactylum tricornutum Phatr_AMT7 nucleic acid sequence

ATGATCTCTACTGGCTCTTCCACGTCCACGAATGCCTACGGCACTTGCTCGGTTCAGCTGGGCGAA
AACTCTTCCGCGAAAGAGCTCTTGGAATGTGTTTCAGATTATCTACAGAATCAGGAGGCGCCTTTC
TCGTCTACTCTGGTACTCACTTTTGCGGGCGCGATTGTCTTTCTAATGCAAGCCGGCTTTGCCATG
GTCTGTGCTGGTGCTGTCCGCACAAAAAATGTCCAAAACGCCATGCTCAAGAATCTGTTGGATGCT
TGCGGTGCGTCCTTGGCGTTCTTTTCCATTGGCTACGCTCTGGGGTTTGGGGGTATGGAGCCCGAA
AGTTCCAAAAAGACCTTTGTCGGACATAGTCAATTCTTTCTGATGGACGTTGACGACTACGCTTTT
TGGTTATTCCAATACGCCTTTTCCGCTGCATCTGCCACAATTGTCGCAGGAACGCTCGCGGAACGA
TGTCAAATGACGGCCTATCTTTGCTACTCCCTTATGCTAACCGGGTGGGTATACCCCGTTATTCTA
CACTCCATATGGAATCCCAACGGCTGGCTATCTGCGTACTCGGTTGATCCGCTTTGGGGCAGCGGG
CTGGTGGATTTTGCTGGCTCTGGCGTCGTTCATGTGACCGGAGGAATCACCGCTCTGTTTGCTACA
ATGGTTTTGGGCCCCCGACGAGGACGCTTTCACGATGATCTTGGGCATGATCTGGCACGGCCACGG
GAATTTCAGGCTCATTCGCCGGCTCTGCAAATGCTTGGTACTTTTATTTTGTGGTTTGGCTTTTAC
GGATTTAACATTGGCTCCGCGCTGATAAGCACAAAGCAAGGCTCAGACGAAGCAGCCGCCTTGGCC
GGTGTCAACACAACGCTCTCCGCTAGCGCGGCAGGTATTGTGGCGCTGTTTTCAAATCTATGGTAC
CTGGAGAAGACGACCGGTGAGCCTCTCTTTGATCTAAAGTATGCTATGAATGGCGCCATCTGCGGT
CTTGTAGCTATTTCTGGCGGCTGCGGGGTCTTCGAGCCCTGGGCCGCGGTGGTCACCGGGGCCGTG
GCCGGTGTGATATATCTATTAGGTAGTCGCGGACTTGTATCCATGCGACTGGATGACGCTGTGGAT
GCCATCCCTGTACACCTCTGTGGTGGGGCCTGGGGCATCCTGGCGGTGGGACTGTTCGCAGCGCCC
GAACGTCTCCTTTCCGTGTATGGACGGAATAATCACCCAGGATTGGTTTATAGCATTCGTGAAGGA
GATATCGATGGCGTTCTTTTCGGAATTCAACTAATTGGTCTCATGTTCATCATGGGATGGGTTATG
ATCATCATGCTACCTTTCTTTGTATGGCTCAACTGGAAAGGCTGGTTCCGATCAGACCCGCTGGAG

FIGURE 5 (continued)

GAGATTCTCGGGCTCGATTTAAGCTATCACGTCGGATTGGCGTTACATACCAACAATGTTCATCCG
GAATACGTTGGCAGCGAAAAAGATGTGGTCGACGAAATTATTTCTACGCGCCAACGAAAGGTCAAC
GGGAGCACCACTACCAAGGCGACCTCAGGTACGGAAGAATTGGAGTATATCCCGGAAGTTAGCGAC
GAAGACTTGAGCGAGATGAAAGAGGAATGCTTGTGA

SEQ ID NO: 16 Phaeodactylum tricornutum Phatr AMT7 translated polypeptide sequence

MISTGSSTSTNAYGTCSVQLGENSSAKELLECVSDYLQNQEAPFSSTLVLTFAGAIVFLMQAGFAM
VCAGAVRTKNVQNAMLKNLLDACGASLAFFSIGYALGFGGMEPESSKKTFVGHSQFFLMDVDDYAF
WLFQYAFSAASATIVAGTLAERCQMTAYLCYSLMLTGWVYPVILHSIWNPNGWLSAYSVDPLWGSG
LVDFAGSGVVHVTGGITALFATMVLGPRRGRFHDDLGHDLARPREFQAHSPALQMLGTFILWFGFY
GFNIGSALISTKQGSDEAAALAGVNTTLSASAAGIVALFSNLWYLEKTTGEPLFDLKYAMNGAICG
LVAISGGCGVFEPWAAVVTGAVAGVIYLLGSRGLVSMRLDDAVDAIPVHLCGGAWGILAVGLFAAP
ERLLSVYGRNNHPGLVYSIREGDIDGVLFGIQLIGLMFIMGWVMIIMLPFFVWLNWKGWFRSDPLE
EILGLDLSYHVGLALHTNNVHPEYVGSEKDVVDEIISTRQRKVNGSTTTKATSGTEELEYIPEVSD
EDLSEMKEECL

SEQ ID NO: 17 Cylindrotheca fusiformis Cylfu AMT1 nucleic acid sequence

ATGGCTGAGTTTGATAACACGTTTATCTTGGATTTTTGCAGTGGTGGAAATGAATCGTCGTCTGAC
GTTCAGGCCTTGTGTCAAGTTGCTGGTCTTGCAAATGGCACAAGTGCCTCTGCCGCTGGACTTGTT
GAGGGTATCAACACCTTCTTCCTACTTTTCGCAGGAGCTCTGGTCTTTCTCATGCAAGCTGGCTTC
GCCATGCTGTGCGCTGGATCCGTCCGTCAAAAGAACGTCAAGAATATCATGTTGAAGAACATGTTG
GACGCTTGTGGTGGTGCTATTGGTTTCTGGACTATCGGGTATGCGTTCGCCTACGCTGATAACTCG
TCGGGAGACAAAACCTTCATTGGAGGCAAGAACTTCTTTGTGAACCAATTGGATGAGTCTGGTGGC
GCATGGATTGGTTTCTTTTTCCAATTCGCCTTTGCTGCCACTGCCGCCACTATTGTCGCCGGAACC
GTTGCTGAGCGCTGTAAGATGAGTGCATACCTTTGCTACTCAGTCTTCCTCACTGGTTTTGTCTAT
CCTGTCGTTGTTCACTCCATCTGGAGTGCTGATGGATGGTTGACTGCCTTCCGTGATGATCCTTGG
AAGGGTGTCGGTGTCATTGATTTCGCCGGATCTGGTGTTGTGCACATGACCGGTGGAGCCACTGCT
CTTGTTGCTGCTATTGTTCTTGGACCCCGTAAGGGACGTTTCTATGATGAGGATGGAAATGCTCTT
GAAACCCCTGCAAGTTTCCCAGCTCACAGTGTGGCCCTTCAAGTCCTTGGTACCTTCCTTCTTTGG
TTCGGATGGTATGGATTCAACCCAGGATCTGCTCTTGTCATTGACAATGCTGCGTCCGCTTCTACC
TCAGCACTTTGTGCTGTCACTACCACTCTTGCCGCTGCCAGTGGTTGTGTCTGTGCGATGTTCACT
GATACCATCATTGAAATGATGGCAACAGGAGAAGCATCTTACGATTTGACCATGGCCATGAACGGT
GCTCTTGGAGGACTTGTTGCCATCACTGCTGGATGCTCCGTTGTCACCCCTTGGGCTTCGATCATC
ATTGGTATCATTGCTGGGTGGGTCTACATTGCATTTTCCAAACTCCTAGTCAAATTGAAGATCGAT
GATGCTGTTGATGCCGTTCCTGTTCACTTCGCCAATGGTATGTGGGGTGTCTTGGCTGTGGGTTTC
TTCGCCGAACCCGACGCCATGGTTACTGCCGGGTACAACGATGTCCCAGGAGTCTTCTACAAGGGA
GATGGTAAACTTCTCCTGTGCCAATTTGTCGCTATCATCTGGATTTGCGCTTGGATCTTCTTCTTG
ATGACTCCTTTCTTCGTCGTCTTGAACATCTTGGGTATGTTCCGTGTCGATCCTCTTGAGGAAGAA
GTTGGTCTTGATATTTCCCACCATCGTGGAGCTGCCTACGACATGACCAGTGCCAAGAAGGAAGAT
GTCGAGGAGCTCATGGAACACCGTTCTTCTAAGCATGGAAAGGTTGAGGTCCCCAAGGAAGTTCAA
AAGGAGGACACCGCCTAAGGAATTTGACATCCCTTCTAG

FIGURE 5 (continued)

SEQ ID NO: 18 Cylindrotheca fusiformis Cylfu_AMT1 translated polypeptide sequence

MAEFDNTFILDFCSGGNESSSDVQALCQVAGLANGTSASAAGLVEGINTFFLLFAGALVFLMQAGF
AMLCAGSVRQKNVKNIMLKNMLDACGGAIGFWTIGYAFAYADNSSGDKTFIGGKNFFVNQLDESGG
AWIGFFFQFAFAATAATIVAGTVAERCKMSAYLCYSVFLTGFVYPVVVHSIWSADGWLTAFRDDPW
KGVGVIDFAGSGVVHMTGGATALVAAIVLGPRKGRFYDEDGNALETPASFPAHSVALQVLGTFLLW
FGWYGFNPGSALVIDNAASASTSALCAVTTTLAAASGCVCAMFTDTIIEMMATGEASYDLTMAMNG
ALGGLVAITAGCSVVTPWASIIIGIIAGWVYIAFSKLLVKLKIDDAVDAVPVHFANGMWGVLAVGF
FAEPDAMVTAGYNDVPGVFYKGDGKLLLCQFVAIIWICAWIFFLMTPFFVVLNILGMFRVDPLEEE
VGLDISHHRGAAYDMTSAKKEDVEELMEHRSSKHGKVEVPKEVQKEDTA

SEQ ID NO: 19 Cylindrotheca fusiformis Cylfu_AMT1 variant nucleic acid sequence

ATGGCTGAGTTTGATAACACGTTTATCTTGGATTTTTGCAGTGGTGGAAATGAATCGTCGTCTGAC
GTTCAGGCCTTGTGTCAAGTTGCTGGTGTAAGTTGTTTGCCGATGTTATTCTGACCACAGTATATC
ATTTTGCCTTGACTTACACCGTCGCGTCTTGATGTTGTGCACTTCAGCTTGCAAATGGCACAAGTG
CCTCTGCCGCTGGACTTGTTGAGGGTATCAACACCTTCTTCCTACTTTTCGCAGGAGCTCTGGTCT
TTCTCATGCAAGCTGGCTTCGCCATGCTGTGCGCTGGATCCGTCCGTCAAAAGAACGTCAAGAATA
TCATGTTGAAGAACATGTTGGACGCTTGTGGTGGTGCTATTGGTTTCTGGACTATCGGGTATGCGT
TCGCCTACGCTGATAACTCGTCGGGAGACAAAACCTTCATTGGAGGCAAGAACTTCTTTGTGAACC
AATTGGATGAGTCTGGTGGCGCATGGATTGGTTTCTTTTTCCAATTCGCCTTTGCTGCCACTGCCG
CCACTATTGTCGCCGGAACCGTTGCTGAGCGCTGTAAGATGAGTGCATACCTTTGCTACTCAGTCT
TCCTCACTGGTTTTGTCTATCCTGTCGTTGTTCACTCCATCTGGAGTGCTGATGGATGGTTGACTG
CCTTCCGTGATGATCCTTGGAAGGGTGTCGGTGTCATTGATTTCGCCGGATCTGGTGTTGTGCACA
TGACCGGTGGAGCCACTGCTCTTGTTGCTGCTATTGTTCTTGGACCCCGTAAGGGACGTTTCTATG
ATGAGGATGGAAATGCTCTTGAAACCCCTGCAAGTTTCCCAGCTCACAGTGTGGCCCTTCAAGTCC
TTGGTACCTTCCTTCTTTGGTTCGGATGGTATGGATTCAACCCAGGATCTGCTCTTGTCATTGACA
ATGCTGCGTCCGCTTCTACCTCAGCACTTTGTGCTGTCACTACCACTCTTGCCGCTGCCAGTGGTT
GTGTCTGTGCGATGTTCACTGATACCATCATTGAAATGATGGCAACAGGAGAAGCATCTTACGATT
TGACCATGGCCATGAACGGTGCTCTTGGAGGACTTGTTGCCATCACTGCTGGATGCTCCGTTGTCA
CCCCTTGGGCTTCGATCATCATTGGTATCATTGCTGGGTGGGTCTACATTGCATTTTCCAAACTCC
TAGTCAAATTGAAGATCGATGATGCTGTTGATGCCGTTCCTGTTCACTTCGCCAATGGTATGTGGG
GTGTCTTGGCTGTGGGTTTCTTCGCCGAACCCGACGCCATGGTTACTGCCGGGTACAACGATGTCC
CAGGAGTCTTCTACAAGGGAGATGGTAAACTTCTCCTGTGCCAATTTGTCGCTATCATCTGGATTT
GCGCTTGGATCTTCTTCTTGATGACTCCTTTCTTCGTCGTCTTGAACATCTTGGGTATGTTCCGTG
TCGATCCTCTTGAGGAAGAAGTTGGTCTTGATATTTCCCACCATCGTGGAGCTGCCTACGACATGA
CCAGTGCCAAGAAGGAAGATGTCGAGGAGCTCATGGAACACCGTTCTTCTAAGCATGGAAAGGTTG
AGGTCCCCAAGGAAGTTCAAAAGGAGGACACCGCCTAA

SEQ ID NO: 20 Cylindrotheca fusiformis Cylfu_AMT1 variant translated polypeptide sequence

MQAGFAMLCAGSVRQKNVKNIMLKNMLDACGGAIGFWTIGYAFAYADNSSGDKTFIGGKNFFVNQL
DESGGAWIGFFFQFAFAATAATIVAGTVAERCKMSAYLCYSVFLTGFVYPVVVHSIWSADGWLTAF
RDDPWKGVGVIDFAGSGVVHMTGGATALVAAIVLGPRKGRFYDEDGNALETPASFPAHSVALQVLG
TFLLWFGWYGFNPGSALVIDNAASASTSALCAVTTTLAAASGCVCAMFTDTIIEMMATGEASYDLT
MAMNGALGGLVAITAGCSVVTPWASIIIGIIAGWVYIAFSKLLVKLKIDDAVDAVPVHFANGMWGV
LAVGFFAEPDAMVTAGYNDVPGVFYKGDGKLLLCQFVAIIWICAWIFFLMTPFFVVLNILGMFRVD
PLEEEVGLDISHHRGAAYDMTSAKKEDVEELMEHRSSKHGKVEVPKEVQKEDTA

FIGURE 5 (continued)

SEQ ID NO: 21 Cylindrotheca fusiformis Cylfu_AMT2a nucleic acid sequence

ATGGCTGAGTTCGATAACACTTTTATCTTGGAATTTTGCAGTGGTGGAAATGAATCGTCGTCTGAC
GTTCAGGTCTTGTGCCAAGTTGCCAGTCTCGCAAACGGCACCAGTGCCTCTGCCGGTGGACTTACT
GAGGGTATCAATACCTTCTTTCTACTTTTTGCTGGAGCTCTAGTCTTTATCATGCAAGCTGGATTC
GCCATGCTGTGTGCTGGATCCGTCCGTCAAAAGAACGTCAAGAATATCATGTTGAAAAACATGTTG
GACGCTTGTGGTGGTGCTATTGGTTTCTGGACTATCGGGTATGCCTTCGCCTACGCTGATAACTCG
TCTGGAAATAAAACATTCATTGGAGGCAAGAACTTCTTTGTGAACCAACTGGATGAGTCTGGAGGT
GCATGGATTGGTTTCTTCTTCCAATTTGCCTTTGCTGCCACTGCCGCCACTATTGTCGCGGGAACC
GTTGCCGAGCGCTGCAAGATGAGTGCGTACCTATGCTACTCAATCTTCCTCACTGGTTTTGTCTAT
CCTGTCGTTGTTCACTCCATCTGGAGTGCTGATGGATGGTTGACTGCCTTTCGTGATGATCCTTGG
CAGGGTGTCGGTGTCATCGATTTCGCCGGATCTGGTGTTGTGCATATGTGCGGTGGAGCCACTGCT
CTTGTTGCTGCTATTGTTCTTGGACCCCGTAAGGGACGTTTCTATGATGAGGATGGAAATGCTCTT
GAAACCCCTGCAAGTTTCCCAGCTCACAGTGTGGCCCTTCAAGTCCTCGGTACCTTCCTTCTTTGG
TTCGGATGGTATGGATTCAACCCAGGATCTGCTCTTGTCATTGACAATGCTGCGTCCGCTTCTACC
TCAGCACTTTGTGCTGTCACTACCACTCTTGCCGCTGCCAGTGGTTGTGTCACCGCGATGTTCACC
GATACCCTCATTGAAATGATGGCTACCGGAGAAGCATCTTATGATTTGACCATGGCCATGAACGGT
GCACTTGCGGGGCTTGTTGCCATCACTGCCGGATGCTCCGTTGTCACTCCTTGGGCTTCTCTCATC
ATTGGTATTATTGGCGGGTGGGTCTACCTTGGACTTTCTAAACTTCTAATCAAATTGAAGATCGAT
GATGCTGTTGATGCCGTCCCTGTTCACTTCGGTAATGGTATGTGGGGTGTCTTGGCTGTTGGCTTC
TTTGCCGAACCCGACGCCATGGTTACTGCCGGGTACAACGATGTCCCAGGAGTGTTCTACAAAGGA
GATGGTTCTCTTCTCCTGTGCCAATTCGTCGCTATCGTTTGGGTTTGCGCTTGGGTCTTCTTCTTG
ATGACTCCTTTCTTCGTCGTCTTGAACATTTTGGGAATGTTCCGTGTCGATCCTCTTGAGGAAGAA
GTTGGTCTTGATATTTCCCACCACCGTGGATCTGCCTACGACATGACTACTGCCAAGAAGGAAGAT
GTCGAAGAGCTCATGGAACACCGTTCTTCGAAGCACGGGAAGGTTGAGATCCCCAAGGAAGTTCAG
AAGGAGGACACCGCCTAA

SEQ ID NO: 22 Cylindrotheca fusiformis Cylfu_AMT2a translated polypeptide sequence

MAEFDNTFILEFCSGGNESSSDVQVLCQVASLANGTSASAGGLTEGINTFFLLFAGALVFIMQAGF
AMLCAGSVRQKNVKNIMLKNMLDACGGAIGFWTIGYAFAYADNSSGNKTFIGGKNFFVNQLDESGG
AWIGFFFQFAFAATAATIVAGTVAERCKMSAYLCYSIFLTGFVYPVVVHSIWSADGWLTAFRDDPW
QGVGVIDFAGSGVVHMCGGATALVAAIVLGPRKGRFYDEDGNALETPASFPAHSVALQVLGTFLLW
FGWYGFNPGSALVIDNAASASTSALCAVTTTLAAASGCVTAMFTDTLIEMMATGEASYDLTMAMNG
ALAGLVAITAGCSVVTPWASLIIGIIGGWVYLGLSKLLIKLKIDDAVDAVPVHFGNGMWGVLAVGF
FAEPDAMVTAGYNDVPGVFYKGDGSLLLCQFVAIVWVCAWVFFLMTPFFVVLNILGMFRVDPLEEE
VGLDISHHRGSAYDMTTAKKEDVEELMEHRSSKHGKVEIPKEVQKEDTA

SEQ ID NO: 23 Thalassiosira pseudonana Thaps_AMT1 nucleic acid sequence

ATGGCCGAACCAACAACAACCATAGGCGACTTCAACGTCACTGCCTGGTGCGGCGACGACGCTGTA
GCAACCTACGAAGGACAATCCGTCGAGAACGGTATCTGTGCAGCCTACGCCTACACCGACGAAACC
AACACCGGTCTTGATGTGTTCTACCTCCTCTTCGCCGCTGCCATGGTCTTCTTCATGCAGGCTGGA
TTCGCCATGCTCTGTGCTGGATCTGTGAGGCAGAAGAATGTGAAGAATATCATGCTTAAGAACATT
TTGGATGCTTGTGGTGGAGCTCTTGGATTTTGGTCTGTGGGATTTGCGTTTGCCTACGGAGGATCT
GGACCGGAGAAGAAGGGATTCATCGGTAACGAGGGATTCTTCCTTGGTGACTTTACAACTGGAGGC
GATTTGATCGGATGGTTCTTCCAGTTCGCCTTTGCTGCCACCGCCGCCACAATTGTGGCTGGAACC
GTAGCCGAGCGTTGCAAGTTCGAGGCCTACCTCTGCTATTCTCTCATGCTCACCGGGTTCGTCTAC

FIGURE 5 (continued)

CCCGTGATTGTGTACTCCATCTGGTCTTCCTCTGGGTTCCTCACCGCCTTCAACGACGACCCTGCC
TTTGGATGTGGTATGCATGATTTCGCCGGATCGGGAGTTGTTCACATGACGGGAGGCATCACTGCC
CTTTGGGCCGCCAAGATTCTCGGACCTCGTATCGGACGCTTCTACGATGCTGATGGCAATGAGCTT
CCCGAGCCAGTGAGCTTCCCTCCCCACTCCGTGGCCCTTCAAGTTCTTGGTACTTTCATCCTTTGG
GTGGGCTGGTACGGATTCAACCCCGGTTCCACTCTTCTCATCAGTAACACGGCCGCAGCTGATGTG
TCTGCCCTTTGTGCCGTCACCACCACCATTGCCGCCGCTTCGGGCTCTGTCTCTGCCATGTTCACT
GATATGTTCTTGGAGCGCAGAAAGACCGGAGAGACTATGTACGACATTACCATGTGTATGAACGGT
GCTCTTTCTGGATTGGTGGGCATCACCGCTGGATGCTCAATCGTTGAGCCTTGGGCTGCCTTTGTC
ATTGGAATTGTCGCCGGATGGACTTACATCTTCTGGTCCAGTCTCCTTGTGAAGCTTAAGATTGAT
GATGCCGTCGATGCCATTCCTGTTCACTTTGGAAACGGAATGTGGGGCTGCATTGCCGTTGGACTC
TTTGCCGAGCCTACCCGTGTAGCCAACGCCTACAGTGACCATGGACACTATGGATGGTTCTACTCA
TGGGGTGCTGGAAACGCCGATGCCCACCTTTTGGCTGCTCAAGTCTGTGGTGTTCTCTGGATCATT
GGATGGGTTTCCGTCATTATGATCCCATACTTCATCCTGCTCAACGTCCTGGGTTTGTTCCGTGTG
GATGCCCTCGAAGAAGAAGTTGGTTTGGATATCTCCCACCACAAGGGAGCTGCCTACGATATGTCC
GGACCTTCTGAAGCTGCCGCCGAGAAGTTTGAGATCTCTAGGAGTCAGCGTAAGCTTGAGATCCCT
GTGGATGTCGCGCCTGCTACTGCTCCTGCCGAGGATGCCGCGTAA

SEQ ID NO: 24 Thalassiosira pseudonana Thaps_AMT1 translated polypeptide sequence

MAEPTTTIGDFNVTAWCGDDAVATYEGQSVENGICAAYAYTDETNTGLDVFYLLFAAAMVFFMQAG
FAMLCAGSVRQKNVKNIMLKNILDACGGALGFWSVGFAFAYGGSGPEKKGFIGNEGFFLGDFTTGG
DLIGWFFQFAFAATAATIVAGTVAERCKFEAYLCYSLMLTGFVYPVIVYSIWSSSGFLTAFNDDPA
FGCGMHDFAGSGVVHMTGGITALWAAKILGPRIGRFYDADGNELPEPVSFPPHSVALQVLGTFILW
VGWYGFNPGSTLLISNTAAADVSALCAVTTTIAAASGSVSAMFTDMFLERRKTGETMYDITMCMNG
ALSGLVGITAGCSIVEPWAAFVIGIVAGWTYIFWSSLLVKLKIDDAVDAIPVHFGNGMWGCIAVGL
FAEPTRVANAYSDHGHYGWFYSWGAGNADAHLLAAQVCGVLWIIGWVSVIMIPYFILLNVLGLFRV
DALEEEVGLDISHHKGAAYDMSGPSEAAAEKFEISRSQRKLEIPVDVAPATAPAEDAA

SEQ ID NO: 25 Thalassiosira pseudonana Thaps_AMT2 nucleic acid sequence

ATGTCTGAAGATCCATCAATCTTTGAAGTGTGTACTGGCCAGCTCGGAACAGATCTTACCGTCGAG
CTTTTACAATGTGTCTCTGATGGAGCTGAAAGCGCAAAGGATGATGTCATCAGTGGCGTCAACTCC
TTCTACCTCATCTTTGCAGGAGCCCTCGTTTTCTTCATGCAAGTCGGTTTCGCCATGCTCTGTGCT
GGATCCATCCGTGAGAAGAACGTCAAGAATGTATTGCTTTGGAATCTCCTCGATTCTGCCGGTGGT
GCCTTTGGTTTCTGGAGTATTGGTTATGCATTTGCTTATGGTGGTGATGATATTACCAAGGGAAAG
ACCTTCATCGGAAACGCTGACTTCTTCTTGAGTGGAGAAACTGATATGGAGTTTTGGTTCTTCCAA
TACGCCTTTGCGTGTGCTCTCTCCTCCATTGTTGCTGGAACCATTGCTGAGCGCACCAAGATGATG
GCCTACTTGTGCTACTCAATCTTCCTTTGTGGATTCGTCTACCCAGTCTGTGCTCATGCCTTTTGG
TCTCAGAATGGATTCCTCTCTGCCTTCGCTGCTGAACCTTTGTGGGGTTCGGGCGTTATTGACTTT
GCAGGATCGGGACCAGTTCACATGTGTGGAGGAGTTGCTGCTCTTGTCATGGCTATTATTCTTGGA
CCTCGTAGGGGACGTTTCTATGACGACGATGGTGTCGTATTGGATGAGCCAAAGTCCATGGGACCT
CACTCCGTCACTTTGCAATTCCTCGGAACCTTTGCTCTTTGGTTCGGATGGTATGGATTCAACCCT
GGTAGCTCCATCTTGATTGCGTCAGCTGCCTCTGGCGACGTTGCATCGCTTGCTGCCGTCAACACT
ACGCTCGGATCTGCTGCTGGAGCACTTTCTGGTATGTTCACCTCCACGATCGTCGACGAAAGAAAG
ACTGGAGTGTATACTTGGGATACTACTGCTGCAATGAACGGATGCCTCACCGGTTTGGTTGCTATT
ACTGCTGGTTGCGCTACCGTCGAGCCTTGGGCTGCCTTCGTCATTGGGCTCACTGCTGGTTGGGTG
TACCTTGCTGCATCTGCTCTTATGCTTCGCTTCAAGATTGATGATGCTGTCGATGCCATCCCCGTT
CACATGTTCGGAGGATCATGGGGAGTTTTTTGCACTGGTCTTTTCACCAGTCCTCGCCGTCTTATT

FIGURE 5 (continued)

ACTGCATACGGAAATGACAATAATGTTGGTTGGTTCTACGAATGGGGACGTGGAAGTGGAAACTTC
ACTCTCCTTGGCTGCCAGCTCGTCTCGATTCTCTTTGTCTTGGGATGGTCTGCTTGCATCTTTGCT
CCATTCTGCTTGGCACTCAAAACCCTCAACTGGCTCCGCATTGACCCTCTCGAGGAGGAGGTTGGT
ATGGATATCAGTCGCCATAAGGGACCTGCCTACGAGTCGGAGGGATCTGCTCATTCTGATGCTATC
GAGAAGTTGAGTGCCTCCCGTCGTGATATTATGAATGCCTCTGGAAGTGGAAGGGGAAAAAGTTTC
AGCAGGTCGACTCCCACGAAAGCTAACGAGGAGCCCAAAATCGAAGCAACTGAGGATGCAGGGGCA
CCCGCTGGAGAAGCAACTGCTTAG

SEQ ID NO: 26 Thalassiosira pseudonana Thaps_AMT2 translated polypeptide sequence

MSEDPSIFEVCTGQLGTDLTVELLQCVSDGAESAKDDVISGVNSFYLIFAGALVFFMQVGFAMLCA
GSIREKNVKNVLLWNLLDSAGGAFGFWSIGYAFAYGGDDITKGKTFIGNADFFLSGETDMEFWFFQ
YAFACALSSIVAGTIAERTKMMAYLCYSIFLCGFVYPVCAHAFWSQNGFLSAFAAEPLWGSGVIDF
AGSGPVHMCGGVAALVMAIILGPRRGRFYDDDGVVLDEPKSMGPHSVTLQFLGTFALWFGWYGFNP
GSSILIASAASGDVASLAAVNTTLGSAAGALSGMFTSTIVDERKTGVYTWDTTAAMNGCLTGLVAI
TAGCATVEPWAAFVIGLTAGWVYLAASALMLRFKIDDAVDAIPVHMFGGSWGVFCTGLFTSPRRLI
TAYGNDNNVGWFYEWGRGSGNFTLLGCQLVSILFVLGWSACIFAPFCLALKTLNWLRIDPLEEEVG
MDISRHKGPAYESEGSAHSDAIEKLSASRRDIMNASGSGRGKSFSRSTPTKANEEPKIEATEDAGA
PAGEATA

SEQ ID NO: 27 Thalassiosira pseudonana Thaps_AMT3 nucleic acid sequence

ATGTTTCAGGTATCAAGAGCTGGACACGTGTCAGTGTATGAGGTCTGCAAATCCTTCGTCAACCCA
GAAGATTCTCAAGCAGATCAGTTTGATGCAATGCTCCAATGTGTTGGGGAATCCAACGGCAAGAGT
ATAGACGCTTTCTTCCTTATATACGCATCATCCCTCGTCTTCTTCATGCAAGCCGGCTTCGCCATG
CTTTGTGCTGGATGCGTTCAACACAAGAATGTTCAGAACAGTATGTTGAAGAACCTCCTAGATGCA
TGCGGTGCAGCCCTTGGCTTCTATTCCGTCGGGTATGCATTTGCTTACGGTGGCATGGACTATTCA
GATCCAAACAAGACATTTATCGGCACAGAGAACTTTTTCTTGATGGGAGTGGACGATTTCATGTTT
TGGCTATTCCAATTTGCATTCGCTGCAAGTGCTGCTACCATTGTGGCAGGAACGTTGGCTGAACGG
TGTCAAATGACGGCATACTTGTGCTACTCAGTGGCAGTGACTGGATTTGTATATCCAGTAGTTGTA
CATTCGGTTTGGTCTCCGCAGGGTTTCTTGTGCGGACAGGCTGTGAGCCCGTTATTTGGAGTTGGT
GTAGTAGACTTTGCAGGATCATCGGTTGTGCATTTGACTGGAGGGTGCATTGCACTCATTGCCACG
TATATTCTAGGCCCAAGGCGAGGGAGATTCTATGATCACAGAGGAGAACCTCTTGAGACACCAGTC
GAGTTTCCGGGTCATTCAGCTGCACTTCAAATGCTCGGTGCCTTCATATTATGGTTTGGATGGTAT
GGCTTCAATACTGGATCAACTCTTTCGATCACCGGCCCTGGCCAACATCAAGTCGTCAGCCTTGTA
GCTGTAAACACAACCCTCGCGGCGGCCTCTGCTTGTGTGGCTTCCCTTCTTGCCAGTTATTATGTC
ATCGAACGAAAGACTGGCGAAGGTACATTCTCGCTTTCTTCAGCAATGAATGGGTGCTTAGGAGGA
TTAGTCAGTATCACTGGTGGATGTGCAGTGGTGGAGCCTTGGGCAGCCGTCGTAATCGGATTCATA
GCAGGGTTGTTGTATCTCTTCACGTCAAAGCTATTGATTCGTTTGCGAATAGACGATGCAGTCGAT
GCTATTCCGGTCCACTTGTCTAACGGAATATGGGGTACGGTTGCGGTGGGGTTGTTCGCATCGTCG
AATCGTTTGCAGTTGGCTTTTGGAAAAGTCGCTGATACTGGTGTGTTCATGGGTGGAACCGGTAAA
CTGTTGGGATGTCAAATAATTGGTGTCTTCTTTGTGCTTGGATGGATTTCCTTCATTATGATTCCG
TTCTTCTGCTTCCTTCACTACATGGGATGGCTTCGATCTGAGTCAATTGATGAAGTAGAAGGGCTT
GATTCCAAGTATCATGGATTGCGAAACAAAGATGAGCATAGACATGACGAAGAAGAAGACAATACT
CCATCACACTACGGCGAAGGCAATTGCAGGCTGAGGCGTAGCATTTTGCGCCATGAGGAAAGAATG
AGACAAGAGGACTCGGCAATACCCGCAACTTTGGTATCAAGTGATGATAGGTTCACGTGTGACTCA
GGAGGAAATAGCACTTCAATGCTATCTACTGCTAAGCAATACACCTAG

FIGURE 5 (continued)

SEQ ID NO: 28 Thalassiosira pseudonana Thaps_AMT3 translated polypeptide sequence

MFQVSRAGHVSVYEVCKSFVNPEDSQADQFDAMLQCVGESNGKSIDAFFLIYASSLVFFMQAGFAM
LCAGCVQHKNVQNSMLKNLLDACGAALGFYSVGYAFAYGGMDYSDPNKTFIGTENFFLMGVDDFMF
WLFQFAFAASAATIVAGTLAERCQMTAYLCYSVAVTGFVYPVVVHSVWSPQGFLCGQAVSPLFGVG
VVDFAGSSVVHLTGGCIALIATYILGPRRGRFYDHRGEPLETPVEFPGHSAALQMLGAFILWFGWY
GFNTGSTLSITGPGQHQVVSLVAVNTTLAAASACVASLLASYYVIERKTGEGTFSLSSAMNGCLGG
LVSITGGCAVVEPWAAVVIGFIAGLLYLFTSKLLIRLRIDDAVDAIPVHLSNGIWGTVAVGLFASS
NRLQLAFGKVADTGVFMGGTGKLLGCQIIGVFFVLGWISFIMIPFFCFLHYMGWLRSESIDEVEGL
DSKYHGLRNKDEHRHDEEEDNTPSHYGEGNCRLRRSILRHEERMRQEDSAIPATLVSSDDRFTCDS
GGNSTSMLSTAKQYT

SEQ ID NO: 29 Thalassiosira pseudonana Thaps_AMT4 nucleic acid sequence

ATGTCCTCGTCGGTACGGACGAGCCTGTACGAGGCTTGCAAATCTACTCAATCCAACTCTACGTTT
TCCAACTCTACGCTCGATGATGCACTCTCTCGCCAGGAACAGATCTTCCGTTGCATTTCGGAATCG
AACGCCAATAGTATTGATACGTTCTTTCTGCTCTATGCCTCATCGCTGGTATTCTTTATGCAAGCC
GGATTCGCGATGCTCTGTGCAGGATCAGTGAGAAAGAAGAATGTGACTAATACCATGTTGAAGAAC
CTTCTCGATGCTTGCGGTGCCGCACTTGGGTTCTATTCTGTGGGATACGCCTTTGCATACGGAGGA
TCAGTAGACGCCGGGAAGAAGACGTTTATAGGTATGAGCAACTTCTTTCTACAGGACGTTGACAAC
TATATGTTTTGGCTCTTTCAGTTTGCATTCGCTGCAACATCAGCTACAATCGTAGCAGGAACATTG
GCTGAAAGATGTCAAATGACAGCTTACCTTTGCTACTCAATTGCATTGACGGGATTTGTCTACCCA
GTTGTCGCTCATTCAATATGGAGTCAGCAGGGGTTCTTATCAGCTACTGCTCAAGATCCATTATGG
GGTACAGGTTTCATTGACTTTGCGGGATCAACAGTAGTACATCTGACGGGTGGATTTACAGCTTTG
ATTGCGACATATCTTCTAGGGCCACGCAGAGGACGGTTCTACGATGCGAAAGGCAAGCAGTTGGAA
GTGCCAAATCCAATGCCTGGCCATTCAGCTGCACTTCAGATGCTTGGTATCTTCATTTTATGGTTT
GGTTGGTATGGTTTCATTGTTGGATCAGCGATAACTATCATCGGTCCGAATCAAGACAAGATCATC
TCTACCTCTGCAGTGAATACGACACTCTCTGCAGCGTCATCATGCTTCTCTGCCTTACTCGTCAAC
TACGTCATTGTCGAGAGGCAATCGGGAGAAGGAGAATTCAGTCTTCTCGCTGCAATGAACGGATGC
TTGAGTGGATTGGTAGCGATAACAGGTGGATGCGCAGTGATAGCACCATGGGCAGCAATTATCGTC
GGACTTTTCGCTGGCCTCTTGTACTTATTTACGTCAAAGGTATTGGTACGAGTTCGAATCGACGAT
GCAGTAGAAGCCATTCCTGTTCACATGACTAACGGGATATGGGGTAGTTTCGCAGTTGGACTATTT
GCCGCTCCATCGGAGCTGCAATTGGTATACGGAAAAGCAAATCACGTTGGACTATTCTATTCTTGG
CATCAAGGGAGTGGAGATGGGACGTTACTCGGTGTCCAATGCTTGGGCATTCTGTTTGTAGTGGGC
TGGGTGTTCTGTCTCATGTCTCCCTTCTTCCTGTTTCTGAACTACAAAGGCTGGTTCAGAGCCGAC
GTCCTCAACGAGATTGCTGGCTTAGATTTGAGTTATCATGATGGAGTGGATATGGAATTGGTGACT
CAGATACGCAATCAAAGGAAGAACTTGCACGTCAACAGCAGGAATCGCTTTAGTTCGAATAGTGCA
TGTCCTCATCATACGGCAACACATGTCGATACCTCAACTGATGCATCACTTTGA

SEQ ID NO: 30 Thalassiosira pseudonana Thaps_AMT4 translated polypeptide sequence

MSSSVRTSLYEACKSTQSNSTFSNSTLDDALSRQEQIFRCISESNANSIDTFFLLYASSLVFFMQA
GFAMLCAGSVRKKNVTNTMLKNLLDACGAALGFYSVGYAFAYGGSVDAGKKTFIGMSNFFLQDVDN
YMFWLFQFAFAATSATIVAGTLAERCQMTAYLCYSIALTGFVYPVVAHSIWSQQGFLSATAQDPLW
GTGFIDFAGSTVVHLTGGFTALIATYLLGPRRGRFYDAKGKQLEVPNPMPGHSAALQMLGIFILWF
GWYGFIVGSAITIIGPNQDKIISTSAVNTTLSAASSCFSALLVNYVIVERQSGEGEFSLLAAMNGC
LSGLVAITGGCAVIAPWAAIIVGLFAGLLYLFTSKVLVRVRIDDAVEAIPVHMTNGIWGSFAVGLF
AAPSELQLVYGKANHVGLFYSWHQGSGDGTLLGVQCLGILFVVGWVFCLMSPFFLFLNYKGWFRAD
VLNEIAGLDLSYHDGVDMELVTQIRNQRKNLHVNSRNRFSSNSACPHHT

FIGURE 5 (continued)

SEQ ID NO: 31 Thalassiosira pseudonana Thaps_AMT6 nucleic acid sequence

ATGGCATCATCAACCACCACAGACACCTATCAAACATGCCTCAGCGATCTCTCGGCGACGTCGTCT
AATGGATCCTCGCCCACCACCGACGCCCTCCTTCAGTGCATCTCCTCCTCCTTCGACGCTCAAACG
GCCTCTACACATGCTTCAATCAACACCTTTTTCCTCCTCTATGCAGCCACCCTCGTCTTCTTCATG
CAAGCCGGCTTTGCCATGGTTAGCGCTGGATGTGTTAGGACGAATAATGTTCAGAATACGCTGCTG
AAGAATCTGTTGGACGCCTGCGGTGCCGCTCTTGGATTCTACACTGTTGGATACGCCTTCGCATGG
GGAGGATCGTTGGATACGGCTACCACCGAGAGGACGTTCATCGGTACACAGAACTTCTTTTTGATG
GATGTGGATAGCTCTCAGGATTCATTTTGGTTGTTTCAATTGGCTTTCTGCTCGGCATCTGCAACG
ATTGTGGCTGGAACGTTGGCTGAACGTTGTCAAATGGTTGCCTATCTTGCATACTCCATGACATTG
GCAGGATTTGTCTACCCAGTCGTCGTACACAGTATCTGGAGTCCGAGTGGATTCTTGAGTGCTACT
CGTGAGACCGATCTCTTCTTGGATGTGGGAATGATTGACTTCGCAGGATCAACCGTCGTGCATTTG
ACGGGAGGGATGACTGCGTTGATTGCTACGATTGTGCTGGGACCGAGGACGGGAAGGTTCTATGAT
TTGAGAGGAAATCCGTTGAAAGTACCAAAGGAGTTTGCAGGACATTCATTGGCTTTGCAAATGTTG
GGGGTGTTCATCTTGTGGTTTGGATGGTATGGCTTCAACGCTGGATCGATCCTCAACATCACCAAC
GATCTCAATCATACAATCGTCAGTCATACTGCCATCAACACAACTCTTGCAGCTTCTGCTGGATCC
ATCATGACTCTCTTCCTCAGTACCGTCGTAGCCGAAAGATTTACGGGGGAGATAGTGTTTAGTCTA
TCTTATGCCATGAATGGGTGTTTGAGTGGATTGGTGGCAATCACAGCTGGCTGCTCAGTGGTAGAA
CACTGGGCTGCAATCATAATCGGGCTTGTAGGAGGGGCATTGTATTTGGCATGCTCCAAGTTCTTG
GTGAAGAAACGTATCGATGATGCAGTTGATGGTATCCCTGTCCACTTGATTAATGGAATCTGGGGA
ACGTTGAGTGTCGGTCTCTTCGCTGTGCCTGAGTTGTTGGAGCAAGTGTATGGAAGGGGTGATCAC
GCTGGTTGGTTTTACAGTTGGGGACAAGGATCAGCAGACGCCAAGTTGTTGGGAGCTCAAGTAGTT
GGAATCTTGTTTGTCAGTGGCTGGGTTATGATCACGATGTTTCCTTTCTTTTGTTTCTTGCATTAT
GTTGGATGGCTTCGTGCCGACTCTCTCGAGGAAGTAGTCGGTCTCGACGCTGCTTACTCCCAAGGT
GTTCTTCAGACGCGTGCCCGTGCCCAAAGTGAGGAAGAGAACATGGAGCATTACATCAGTGAATAT
GTTAAGCAGCGTGAGGAAAAAGCATTCATCAAGAAGATCAACAGCAATAGTACTCACGGACGTACT
ATCCTTGGTGCAAGCATGCATTCAATGAACATCATTAATTCCAGCATGCATTCCAGAAAGGACAGT
CTACCACGTGCAATTGAAAGTCTCAACAATTCAAGACACTCTGGTTCAAGAGGATCAAGATCAATT
AATGATATTGCGATTGACAATTTGCATGGTCAATCTGAGGATGGTTTTGCTGCACCTGATGAGGGC
AGTGCTTAG

SEQ ID NO: 32 Thalassiosira pseudonana Thaps_AMT6 translated polypeptide sequence

MASSTTTDTYQTCLSDLSATSSNGSSPTTDALLQCISSSFDAQTASTHASINTFFLLYAATLVFFM
QAGFAMVSAGCVRTNNVQNTLLKNLLDACGAALGFYTVGYAFAWGGSLDTATTERTFIGTQNFFLM
DVDSSQDSFWLFQLAFCSASATIVAGTLAERCQMVAYLAYSMTLAGFVYPVVVHSIWSPSGFLSAT
RETDLFLDVGMIDFAGSTVVHLTGGMTALIATIVLGPRTGRFYDLRGNPLKVPKEFAGHSLALQML
GVFILWFGWYGFNAGSILNITNDLNHTIVSHTAINTTLAASAGSIMTLFLSTVVAERFTGEIVFSL
SYAMNGCLSGLVAITAGCSVVEHWAAIIIGLVGGALYLACSKFLVKKRIDDAVDGIPVHLINGIWG
TLSVGLFAVPELLEQVYGRGDHAGWFYSWGQGSADAKLLGAQVVGILFVSGWVMITMFPFFCFLHY
VGWLRADSLEEVVGLDAAYSQGVLQTRARAQSEEENMEHYISEYVKQREEKAFIKKINSNSTHGRT
ILGASMHSMNIINSSMHSRKDSLPRAIESLNNSRHSGSRGSRSINDIAIDNLHGQSEDGFAAPDEG
SA

SEQ ID NO: 33 Conserved Domain comprised within SEQ ID NO: 2 and within SEQ ID NO: 4

MQAGFAMLCAGSVRQKNVKNIMLKNLLDACGGAIGFYTVGFGFAYGGDDTTDKTFIGNSYFALRDY
TNYAGFFFQFAFAATAATIVAGTVAERCKMSAYLCYSLFLTGFVYPVVVRSVWSSNGFLSAFSADP
FQGVGTVDFAGSGVVHMTGGLTALIAAIVLGPRKGRFYDEDGNPLETPASFPAHSVALQILGTFIL

FIGURE 5 (continued)

WFGWYGFNPGSALKIANADSAATAALCAVTTTMAAAAGCVSAMFTDSIIDGMATGETTYDLTMAMN
GCLAGLVAVTAGTSVVTPWAAIIIGVVGGWVYIGMSKLLIKLKIDDAVDAIPVHFANGFWGVLATG
LFANGGLMATAGYNSEHEGWFYEWGSGSGDGSLLICQLACLAWIIGWVTTIMTPFFILLNMAGMFR
VDPLEEEVGLD

SEQ ID NO: 34 Oryza sativa GOS2 promoter

AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTTAAAAAAATAGAATGAAGATATTCTGAACGTATTGGCAAAGATTTAAA
CATATAATTATATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC

SEQ ID NO: 35 Prm09458

GGGGACAAGTTTGTACAAAAAAGCAGGCTTAAACAATGATGCAGGCCGGG

SEQ ID NO: 36 Prm09459

GGGGACCACTTTGTACAAGAAAGCTGGGTACACGAGCAGCAATTAAACC

FIGURE 5 (continued)

PLANTS HAVING INCREASED YIELD-RELATED TRAITS AND A METHOD FOR MAKING THE SAME

RELATED APPLICATIONS

This application is a national stage application (under 35 U.S.C. §371) of PCT/EP2008/065947, filed Nov. 21, 2008, which claims benefit of European application 07121362.3, filed Nov. 22, 2007 and U.S. Provisional Application 60/990, 132, filed Nov. 26, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_14546_00064. The size of the text file is 124 KB, and the text file was created on Mar. 8, 2013.

The present invention relates generally to the field of molecular biology and concerns a method for increasing various plant yield-related traits by increasing expression in a plant of a nucleic acid sequence encoding an ammonium transporter (AMT) polypeptide. The present invention also concerns plants having increased expression of a nucleic acid sequence encoding an AMT polypeptide, which plants have increased yield-related traits relative to control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigour has been a limitation to the introduction of maize (*Zea mays* L.) hybrids based on Corn Belt germplasm in the European Atlantic.

Harvest index, the ratio of seed yield to aboveground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73). Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of importance is that of improved abiotic stress tolerance. Abiotic stress is a primary cause of crop loss worldwide, reducing average yields for most major crop plants by more than 50% (Wang et al. (2003) Planta 218: 1-14). Abiotic stresses may be caused by drought, salinity, extremes of temperature, chemical toxicity, excess or deficiency of nutrients (macroelements and/or microelements), radiation and oxidative stress. The ability to increase plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increase yield-related traits (seed yield and/or biomass) in plants may be through modification of the inherent growth mechanisms of a plant, such as the cell cycle or various signaling pathways involved in plant growth or in defense mechanisms.

It has now been found that various yield-related traits may be increased in plants relative to control plants, by increasing expression in a plant of a nucleic acid sequence encoding an ammonium transporter (AMT) polypeptide. The increased yield-related traits comprise one or more of: increased early vigour, increased aboveground biomass, increased root biomass, increased total seed yield per plant, increased seed filling rate, increased number of filled seeds, and increased harvest index.

BACKGROUND

Ammonium and nitrate are primary nitrogen sources for plant growth and development. Plants require transporters for acquisition of both ammonium and nitrate. Transporters of ammonium and nitrate exist not only in plants, but in almost all organisms. Ammonium transporters (AMTs) usually exist in a genome as gene families, for example at least: six in *Arabidopsis thaliana*, eight in *Chlamydomonas reinhardtii* (Gonzales-Ballester et al. (2004) Plant Molec Biol 56: 863-878), fourteen in poplar (Couturier et al. (2007) New Phytologist 174: 137-150), six in diatom *Phaeoactylum tricornutum* (Allen (2005) J Phycology 41).

Based on phylogenetic analysis, three subfamilies of ammonium transporters were identified (Loqué & von Wiren (2004) J Exp Bot 55(401): 1293-1305):

1. the AMT subfamily, including the plant AMT1-type transporters, and cyanobacterial ammonium transporters;
2. the MEP subfamily, including the plant AMT2-type transporters, the yeast MEP transporters, the *E. coli* AmtB, and other prokaryotic homologues;
3. The Rh subfamily, including only human and animal Rhesus blood group antigens.

All AMT polypeptides are highly hydrophobic membrane proteins with at least 10, more commonly 11, putative transmembrane spanning helices. The AMT polypeptides have been shown in numerous reports to be able to uptake ammonium over a wide concentration range, although with different affinities from organism to organism. Within certain organisms, such as plants, high and low affinity ammonium transporters were identified (Gazzarini et al. (1999) Plant Cell 11:937-47). In addition to affinity properties, several other regulatory mechanisms have been identified for ammonium uptake, for example at transcriptional and post-transcriptional levels (Yuan et al. (2007) Plant Phys 143: 732-744).

Over-expression of a nucleic acid sequence from rice encoding an AMT1 was performed in two rice cultivars (Taipei 309 and Jarrah), using a maize ubiquitin promoter for constitutive expression. Shoot and root biomass of transgenic lines decreased during seedling and early vegetative stage compared to wild type, especially when grown under high ammonium nutrition (Hogue et al. (2006) Functional Plant Biol 33: 153-163). The authors concluded that decreased biomass of the transgenic plants at early stages of growth might have been caused by the accumulation of ammonium in the roots owing to the inability of ammonium assimilation to match the greater ammonium uptake.

In U.S. Pat. No. 6,620,610, is described a nucleic acid sequence encoding an AMT1 polypeptide from *Arabidopsis thaliana*, plasmids comprising the nucleic acid sequence encoding an AMT1 for expression in yeast and bacteria.

In U.S. Pat. No. 6,833,492 are described nucleic acid sequences encoding an AMT1 polypeptide from soybean, corn, wheat, and rice. A nucleic acid sequence encoding an AMT1 polypeptide or an AMT polypeptide having 90% amino acid sequence identity to the isolated soybean AMT1 polypeptide is described. Plants and seeds comprising a recombinant nucleic acid sequence encoding such a polypeptide sequence are described, as well as methods to produce such plants.

Surprisingly, it has now been found that increasing expression of a nucleic acid sequence encoding an AMT polypeptide gives plants having increased yield-related traits relative to control plants.

According to one embodiment, there is provided a method for increasing yield-related traits in plants relative to control plants, comprising increasing expression of a nucleic acid sequence encoding an AMT polypeptide as defined herein, in a plant. The increased yield-related traits comprise one or more of: increased early vigour, increased aboveground biomass, increased root biomass, increased total seed yield per plant, increased seed filling rate, increased number of filled seeds, increased number of flowers per panicle, and increased harvest index.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions | Residue | Conservative Substitutions |
|---|---|---|---|
| Ala | Ser | Leu | lle; Val |
| Arg | Lys | Lys | Arg; Gln |
| Asn | Gln; His | Met | Leu; lle |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | lle; Leu |
| lle | Leu, Val | | |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acid molecules are in solution. The hybridisation process can also occur with one of the complementary nucleic acid molecules immobilised to a matrix such as magnetic beads, Sepharose beads or any other resin. The hybridisation process can furthermore occur with one of the complementary nucleic acid molecules immobilised to a solid support such as a nitro-cellulose or nylon membrane or immobilised by e.g. photolithography to, for example, a siliceous glass support (the latter known as nucleic acid sequence arrays or microarrays or as nucleic acid sequence chips). In order to allow hybridisation to occur, the nucleic acid molecules are generally thermally or chemically denatured to melt a double strand into two single strands and/or to remove hairpins or other secondary structures from single stranded nucleic acid molecules.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acid sequences may deviate in sequence and still encode a substantially identical polypeptide, due to the degeneracy of the genetic code. Therefore medium stringency hybridisation conditions may sometimes be needed to identify such nucleic acid sequence molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid sequence strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m=81.5°\text{ C.}+16.6\times \log_{10}[Na^+]^a+0.41x\%[G/C^b]-500x[L^c]^{-1}-0.61x\text{ \% formamide}$$

2) DNA-RNA or RNA-RNA hybrids:

$$Tm=79.8+18.5\ (\log_{10}[Na^+]^a)+0.58(\%\ G/C^b)+11.8\ (\%\ G/C^b)^2-820/L^c$$

3) oligo-DNA or oligo-RNA[d] hybrids:

For <20 nucleotides: $T_m=2(l_n)$

For 20-35 nucleotides: $T_m=22+1.46(l_n)$

[a] or for other monovalent cation, but only accurate in the 0.01-0.4 M range.

[b] only accurate for % GC in the 30% to 75% range.

[c] L=length of duplex in base pairs.

[d] oligo, oligonucleotide; $l_n$,=effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid sequence hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acid molecules of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acid sequences or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms “regulatory element”, “control sequence” and “promoter” are all used interchangeably herein and are to be taken in a broad context to refer to regulatory nucleic acid sequences capable of effecting expression of the sequences to which they are ligated. The term “promoter” typically refers to a nucleic acid sequence control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, increasers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term “regulatory element” also encompasses a synthetic fusion molecule or derivative that confers, activates or increases expression of a nucleic acid sequence molecule in a cell, tissue or organ.

A “plant promoter” comprises regulatory elements, which mediate the expression of a coding sequence segment in plant cells. The “plant promoter” preferably originates from a plant cell, e.g. from the plant which is transformed with the nucleic acid sequence to be expressed in the inventive process and described herein. This also applies to other “plant” regulatory signals, such as “plant” terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid sequence molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid sequence used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by “weak promoter” is intended a promoter that drives expression of a coding sequence at a low level. By “low level” is intended at levels of about 1/10,000 transcripts to about 1/100,000 transcripts, to about 1/500,0000 transcripts per cell. Conversely, a “strong promoter” drives expression of a coding sequence at high level, or at about 1/10 transcripts to about 1/100 transcripts to about 1/1000 transcripts per cell. Generally, by “medium strength promoter” is intended a promoter that drives expression of a coding sequence at a level that is in all instances below that obtained under the control of a 35S CaMV promoter.

Operably Linked

The term “operably linked” as used herein refers to a functional linkage between the promoter sequence and the gene of interest, such that the promoter sequence is able to initiate transcription of the gene of interest.

Constitutive Promoter

A “constitutive promoter” refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of plant constitutive promoters

| Gene Source | Reference |
|---|---|
| Actin | McElroy et al, Plant Cell, 2: 163-171, 1990 |
| HMGB | WO 2004/070039 |
| GOS2 | de Pater et al, Plant J Nov;2(6):837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231:276-285, 1992 |
| Alfalfa H3 histone | Wu et al. Plant Mol. Biol. 11:641-649, 1988 |
| Actin 2 | An et al, Plant J. 10(1); 107-121, 1996 |
| Rubisco small subunit | US 4,962,028 |
| OCS | Leisner (1988) Proc Natl Acad Sci USA 85(5): 2553 |
| SAD1 | Jain et al., Crop Science, 39 (6), 1999: 1696 |

TABLE 2a-continued

| Examples of plant constitutive promoters | |
|---|---|
| Gene Source | Reference |
| SAD2 | Jain et al., Crop Science, 39 (6), 1999: 1696 |
| V-ATPase | WO 01/14572 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

| Examples of root-specific promoters | |
|---|---|
| Gene Source | Reference |
| Rice RCc3 | Xu et al (1995) Plant Mol Biol 27(2): 237-48 |
| Arabidopsis phosphate transporter PHT1 | Kovama et al., 2005 |
| Medicago phosphate transporter | Xiao et al., 2006 |
| Arabidopsis Pyk10 | Nitz et al. (2001) Plant Sci 161(2): 337-346 |
| Tobacco root-specific genes RB7, RD2, RD5, RH12 | Conkling et al. (1990) Plant Phys 93(3): 1203-1211 |
| Barley root-specific lectin | Lerner & Raikhel (1989) Plant Phys 91: 124-129 |
| Root-specific hydroxy-proline rich protein | Keller & Lamb (1989) Genes & Dev 3: 1639-1646 |
| Arabidopsis CDC27B/hobbit | Blilou et al. (2002) Genes & Dev 16: 2566-2575 |

A seed-specific promoter is transcriptionally active predominantly in seed tissue, but not necessarily exclusively in seed tissue (in cases of leaky expression). The seed-specific promoter may be active during seed development and/or during germination. Examples of seed-specific promoters are shown in Table 2c below. Further examples of seed-specific promoters are given in Qing Qu and Takaiwa (Plant Biotechnol. J. 2, 113-125, 2004), which disclosure is incorporated by reference herein as if fully set forth.

TABLE 2c

| Examples of seed-specific promoters | |
|---|---|
| Gene source | Reference |
| seed-specific genes | Simon et al., Plant Mol. Biol. 5: 191, 1985;<br>Scofield et al., J. Biol. Chem. 262: 12202, 1987.;<br>Baszczynski et al., Plant Mol. Biol. 14: 633, 1990. |
| Brazil Nut albumin | Pearson et al., Plant Mol. Biol. 18: 235-245, 1992. |
| Legumin | Ellis et al., Plant Mol. Biol. 10: 203-214, 1988. |
| glutelin (rice) | Takaiwa et al., Mol. Gen. Genet. 208: 15-22, 1986;<br>Takaiwa et al., FEBS Letts. 221: 43-47, 1987. |
| Zein | Matzke et al Plant Mol Biol, 14(3): 323-32 1990 |
| NapA | Stalberg et al, Planta 199: 515-519, 1996. |
| Wheat LMW and HMW glutenin-1 | Mol Gen Genet 216: 81-90, 1989; NAR 17: 461-2, 1989 |
| Wheat SPA | Albani et al, Plant Cell, 9: 171-184, 1997 |
| Wheat α, β, γ-gliadins | EMBO J. 3: 1409-15, 1984 |
| Barley Itr1 promoter | Diaz et al. (1995) Mol Gen Genet 248(5): 592-8 |

TABLE 2c-continued

| Examples of seed-specific promoters | |
|---|---|
| Gene source | Reference |
| Barley B1, C, D, hordein | Theor Appl Gen 98: 1253-62, 1999; Plant J 4: 343-55, 1993; Mol Gen Genet 250:750-60, 1996 |
| Barley DOF | Mena et al, The Plant Journal, 116(1): 53-62, 1998 |
| blz2 | EP99106056.7 |
| Synthetic promoter | Vicente-Carbajosa et al., Plant J. 13: 629-640, 1998. |
| rice prolamin NRP33 | Wu et al, Plant Cell Physiology 39(8) 885-889, 1998 |
| rice a-globulin Glb-1 | Wu et al, Plant Cell Physiology 39(8) 885-889, 1998 |
| rice OSH1 | Sato et al, Proc. Natl. Acad. Sci. USA, 93: 8117-8122, 1996 |
| rice α-globulin REB/OHP-1 | Nakase et al. Plant Mol. Biol. 33: 513-522, 1997 |
| riceADP-glucose pyrophos-phorylase | Trans Res 6:157-68, 1997 |
| Maize ESR gene family | Plant J 12:235-46, 1997 |
| Sorghum α-kafirin | DeRose et al., Plant Mol. Biol 32:1029-35, 1996 |
| KNOX | Postma-Haarsma et al, Plant Mol. Biol. 39:257-71, 1999 |
| rice oleosin | Wu et al, J. Biochem. 123:386, 1998 |
| sunflower oleosin | Cummins et al., Plant Mol. Biol. 19: 873-876, 1992 |
| PRO0117, putative rice 40S ribosomal protein | WO 2004/070039 |
| PRO0136, rice alanine aminotransferase | Unpublished |
| PRO0147, trypsin inhibitor ITR1 (barley) | Unpublished |
| PRO0151, rice WSI18 | WO 2004/070039 |
| PRO0175, rice RAB21 | WO 2004/070039 |
| PRO005 | WO 2004/070039 |
| PRO0095 | WO 2004/070039 |
| α-amylase (Amy32b) | Lanahan et al, Plant Cell 4:203-211, 1992; Skriver et al, Proc Natl Acad Sci USA 88:7266-7270, 1991 |
| Cathepsin β-like gene | Cejudo et al, Plant Mol Biol 20:849-856, 1992 |
| Barley Ltp2 | Kalla et al., Plant J. 6:849-60, 1994 |
| Chi26 | Leah et al., Plant J. 4:579-89, 1994 |
| Maize B-Peru | Selinger et al., Genetics 149;1125-38,1998 |

A green tissue-specific promoter as defined herein is a promoter that is transcriptionally active predominantly in green tissue, substantially to the exclusion of any other parts of a plant, whilst still allowing for any leaky expression in these other plant parts.

Examples of green tissue-specific promoters which may be used to perform the methods of the invention are shown in Table 2d below.

TABLE 2d

| Examples of green tissue-specific promoters | | |
|---|---|---|
| Gene | Expression | Reference |
| Maize Orthophosphate dikinase | Leaf specific | Fukavama et al., 2001 |
| Maize Phosphoenolpyruvate carboxylase | Leaf specific | Kausch et al., 2001 |
| Rice Phosphoenolpyruvate carboxylase | Leaf specific | Liu et al., 2003 |
| Rice small subunit Rubisco | Leaf specific | Nomura et al., 2000 |
| rice beta expansin EXBP9 | Shoot specific | WO 2004/070039 |
| Pigeonpea small subunit Rubisco | Leaf specific | Panguluri et al., 2005 |
| Pea RBCS3A | Leaf specific | |

Another example of a tissue-specific promoter is a meristem-specific promoter, which is transcriptionally active predominantly in meristematic tissue, substantially to the exclusion of any other parts of a plant, whilst still allowing for any leaky expression in these other plant parts. Examples of meristem-specific promoters which may be used to perform the methods of the invention are shown in Table 2e below.

TABLE 2e

| Examples of meristem-specific promoters | | |
|---|---|---|
| Gene source | Expression pattern | Reference |
| rice OSH1 | Shoot apical meristem, fromembryo globular stage to seedling stage | Sato et al. (1996) . Proc. Natl. Acad Sci. USA, 93: 8117-8122 |
| Rice metallothionein | Meristem specific | BAD87835.1 |
| WAK1 & WAK 2 | Shoot and root apical meristems, and in expanding leaves and sepals | Wagner & Kohorn (2001) Plant Cell 13(2): 303-318 |

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription increasers or translation increasers. Isolated nucleic acid sequences which serve as promoter or increaser elements may be introduced in an appropriate position (typically upstream) of a non-heterologous form of a polynucleotide so as to upregulate expression of a nucleic acid sequence encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron increasement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene.

Decreased Expression

Reference herein to "decreased expression" or "reduction or substantial elimination" of expression is taken to mean a decrease in endogenous gene expression and/or polypeptide levels and/or polypeptide activity relative to control plants. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control plants.

For the reduction or substantial elimination of expression an endogenous gene in a plant, a sufficient length of substantially contiguous nucleotides of a nucleic acid sequence is required. In order to perform gene silencing, this may be as little as 20, 19, 18, 17, 16, 15, 14, 13, 12, 11, 10 or fewer nucleotides, alternatively this may be as much as the entire gene (including the 5' and/or 3' UTR, either in part or in whole). The stretch of substantially contiguous nucleotides may be derived from the nucleic acid sequence encoding the protein of interest (target gene), or from any nucleic acid sequence capable of encoding an orthologue, paralogue or homologue of the protein of interest. Preferably, the stretch of substantially contiguous nucleotides is capable of forming hydrogen bonds with the target gene (either sense or antisense strand), more preferably, the stretch of substantially contiguous nucleotides has, in increasing order of preference, 50%, 60%, 70%, 80%, 85%, 90%, 95%, 96%, 97%, 98%, 99%, 100% sequence identity to the target gene (either sense or antisense strand). A nucleic acid sequence encoding a (functional) polypeptide is not a requirement for the various methods discussed herein for the reduction or substantial elimination of expression of an endogenous gene.

This reduction or substantial elimination of expression may be achieved using routine tools and techniques. A method for the reduction or substantial elimination of endogenous gene expression is by RNA-mediated silencing using an inverted repeat of a nucleic acid sequence or a part thereof (in this case a stretch of substantially contiguous nucleotides derived from the gene of interest, or from any nucleic acid sequence capable of encoding an orthologue, paralogue or homologue of the protein of interest), preferably capable of forming a hairpin structure. Another example of an RNA silencing method involves the introduction of nucleic acid sequences or parts thereof (in this case a stretch of substantially contiguous nucleotides derived from the gene of interest, or from any nucleic acid sequence capable of encoding an orthologue, paralogue or homologue of the protein of interest) in a sense orientation into a plant. Another example of an RNA silencing method involves the use of antisense nucleic acid sequences. Gene silencing may also be achieved by insertion mutagenesis (for example, T-DNA insertion or transposon insertion) or by strategies as described by, among others, Angell and Baulcombe ((1999) Plant J 20(3): 357-62), (Amplicon VIGS WO 98/36083), or Baulcombe (WO 99/15682). Other methods, such as the use of antibodies directed to an endogenous polypeptide for inhibiting its function in planta, or interference in the signaling pathway in which a polypeptide is involved, will be well known to the skilled man. Artificial and/or natural microRNAs (miRNAs) may be used to knock out gene expression and/or mRNA translation. Endogenous miRNAs are single stranded small RNAs of typically 19-24 nucleotides long. Artificial microRNAs (amiRNAs), which are typically 21 nucleotides in length, can be genetically engineered specifically to negatively regulate gene expression of single or multiple genes of interest. Determinants of plant microRNA target selection are well known in the art. Empirical parameters for target recognition have been defined and can be used to aid in the design of specific amiRNAs (Schwab et al., (2005) Dev Cell 8(4): 517-27). Convenient tools for design and generation of amiRNAs and their precursors are also available to the public (Schwab et al., (2006) Plant Cell 18(5):1121-33).

For optimal performance, the gene silencing techniques used for reducing expression in a plant of an endogenous gene requires the use of nucleic acid sequences from monocotyledonous plants for transformation of monocotyledonous plants, and from dicotyledonous plants for transformation of dicotyledonous plants. Preferably, a nucleic acid sequence from any given plant species is introduced into that same species. For example, a nucleic acid sequence from rice is transformed into a rice plant. However, it is not an absolute requirement that the nucleic acid sequence to be introduced originates from the same plant species as the plant in which it will be introduced. It is sufficient that there is substantial homology between the endogenous target gene and the nucleic acid sequence to be introduced.

Described above are examples of various methods for the reduction or substantial elimination of expression in a plant of an endogenous gene. A person skilled in the art would readily be able to adapt the aforementioned methods for silencing so as to achieve reduction of expression of an endogenous gene in a whole plant or in parts thereof through the use of an appropriate promoter, for example.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid sequence construct of the invention. These marker genes enable the identification of a successful transfer of the nucleic acid sequence molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luceferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequence molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acid sequences have been introduced successfully, the process according to the invention for introducing the nucleic acid sequences advantageously employs techniques which enable the removal or excision of these marker genes. One such a method is what is known as co-transformation. The co-transformation method employs two vectors simultaneously for the transformation, one vector bearing the nucleic acid sequence according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid sequence (known as the Ac/Ds technology). The transformants can be crossed with a transposase source or the transformants are transformed with a nucleic acid sequence construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acid sequences used in the method of the invention are not at their natural locus in the genome of said plant, it being possible for the nucleic acid sequences to be expressed homologously or heterologously. However, as mentioned, transgenic also means that, while the nucleic acid sequence according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acid sequences according to the invention at an unnatural locus in the genome, i.e. homologous or, preferably, heterologous expression of the nucleic acid sequences takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the *agrobacteria* to act on plant seeds or to inoculate the plant meristem with *agrobacteria*. It has proved particularly expedient in accordance with the invention to allow a suspension of transformed *agrobacteria* to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acid sequences or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with *agrobacteria* and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed *agrobacteria*, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation increaser or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acid sequences encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid sequence at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres. The term "yield" of a plant may relate to vegetative biomass, to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Increase

The terms "increase", "improve" or "increase" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per panicle and/or per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; f) increased number of primary panicles; (g) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in yield may also manifest itself as an increase in seed area and/or seed length and/or seed width and/or seed perimeter. Increased seed yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid sequence of interest. The term "plant" also encompasses plant cells, suspension cultures, callus tissue, embryos, meristematic regions, gametophytes, sporophytes, pollen and microspores, again wherein each of the aforementioned comprises the gene/nucleic acid sequence of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), *Hemerocaffis fulva, Hibiscus* spp., *Hordeum* spp. (e.g. *Hordeum vulgare*), *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sylvatica, Lycopersicon* spp. (e.g. *Lycopersicon esculentum, Lycopersicon lycopersicum, Lycopersicon pyriforme*), *Macrotyloma* spp., *Malus* spp., *Malpighia emarginata, Mammea americana, Mangifera indica, Manihot* spp., *Manilkara zapota, Medicago sativa, Melilotus* spp., *Mentha* spp., *Miscanthus sinensis, Momordica* spp., *Morus nigra, Musa* spp., *Nicotiana* spp., *Olea* spp., *Opuntia* spp., *Ornithopus* spp., *Oryza* spp. (e.g. *Oryza sativa, Oryza latifolia*), *Panicum miliaceum, Panicum virgatum, Passiflora edulis, Pastinaca sativa, Pennisetum* sp., *Persea* spp., *Petroselinum crispum, Phalaris arundinacea, Phaseolus* spp., *Phleum pratense, Phoenix* spp., *Phragmites australis, Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Ricinus communis, Rubus* spp., *Saccharum* spp., *Salix* sp., *Sambucus* spp., *Secale cereale, Sesamum* spp., *Sinapis* sp., *Solanum* spp. (e.g. *Solanum tuberosum, Solanum integrifolium* or *Solanum lycopersicum*), *Sorghum bicolor, Spinacia* spp., *Syzygium* spp., *Tagetes* spp., *Tamarindus indica, Theobroma cacao, Trifolium* spp., *Triticale* sp., *Triticosecale rimpaui, Triticum* spp. (e.g. *Triticum aestivum, Triticum durum, Triticum turgidum, Triticum hybernum, Triticum macha, Triticum sativum* or *Triticum vulgare*), *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others.

DETAILED DESCRIPTION OF THE INVENTION

Surprisingly, it has now been found that increasing expression in a plant of a nucleic acid sequence encoding an AMT polypeptide as defined herein, gives plants having increased yield-related traits relative to control plants. According to a first embodiment, the present invention provides a method for increasing yield-related traits in plants relative to control plants, comprising increasing expression in a plant of a nucleic acid sequence encoding an AMT polypeptide.

A preferred method for increasing expression of a nucleic acid sequence encoding an AMT polypeptide is by introducing and expressing in a plant a nucleic acid sequence encoding an AMT polypeptide.

Any reference hereinafter to a "protein useful in the methods of the invention" is taken to mean a AMT polypeptide as defined herein. Any reference hereinafter to a "nucleic acid sequence useful in the methods of the invention" is taken to mean a nucleic acid sequence capable of encoding such an AMT polypeptide. The nucleic acid sequence to be introduced into a plant (and therefore useful in performing the methods of the invention) is any nucleic acid sequence encoding the type of polypeptide, which will now be described, hereafter also named "AMT nucleic acid sequence" or "AMT gene".

An "AMT polypeptide" as defined herein refers to any polypeptide comprising a domain having in increasing order of preference at least 50%, 55%, 60%, 65%, 70%, 75%, 80%, 85%, 90%, 95%, 98%, 99% or more amino acid sequence identity to a Conserved Domain (CD) as represented by SEQ ID NO: 33.

Alternatively or additionally, an "AMT polypeptide" as defined herein refers to any polypeptide comprising: (i) an ammonium transporter domain with an InterPro accession IPR0001905; and (ii) at least 10 transmembrane spanning helices.

Alternatively or additionally, an "AMT polypeptide" as defined herein refers to any polypeptide sequence which when used in the construction of an AMT phylogenetic tree, such as the one depicted in FIG. 2, clusters with the clade of AMT polypeptides comprising the polypeptide sequence as represented by SEQ ID NO: 2 (encircled in FIG. 2) rather than with any other AMT clade.

Alternatively or additionally, an "AMT polypeptide" as defined herein refers to any polypeptide having in increasing order of preference at least 40%, 45%, 50%, 55%, 60%, 65%, 70%, 75%, 80%, 85%, 90%, 95%, 98%, 99% or more amino acid sequence identity to the AMT polypeptide as represented by SEQ ID NO: 2 or to any of the polypeptide sequences given in Table A herein.

Alternatively or additionally, an "AMT polypeptide" is capable of complementing a yeast strain MLY131 which lacks all three native yeast ammonium transporters (Hildebrand (2005) J Phycol 41: 105-113).

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32: D134-D137, (2004)), or Pfam (Bateman et al., Nucleic Acids Research 30(1): 276-280 (2002). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788(2003)). Analysis of the polypeptide sequence of SEQ ID NO: 2 is presented below in Example 4 herein. For example, an AMT polypeptide as represented by SEQ ID NO: 2 comprises an ammonium transporter domain with an InterPro accession IPR0001905. Domains may also be identified using routine techniques, such as by sequence alignment. An alignment of the polypeptides of Table A herein, is shown in FIG. 3. Such alignments are useful for identifying the most conserved domains between the AMT polypeptides, such as the conserved Domain (CD) as represented by SEQ ID NO: 33 (comprised in SEQ ID NO: 2).

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., (2003) BMC Bioinformatics, 10: 29. MatGAT: an application that generates similarity/identity matrices using protein or DNA sequences). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid sequence or polypeptide sequence or over selected domains or conserved motif(s), using the programs mentioned above using the default parameters. Example 3 herein describes in Table B the percentage identity between the AMT polypeptide as represented by SEQ ID NO: 2 and the AMT polypeptides listed in Table A, which can be as low as 44% amino acid sequence identity. The percentage identity can be increased if the identity calculation is performed between the Conserved Domain (CD) as represented by SEQ ID NO: 33 (comprised in SEQ ID NO: 2 and in SEQ ID N: 4) and the Conserved Domain of the AMT polypeptides of Table A and represented in FIG. 3. The results of such calculations are presented in Table B1 of the present application.

The task of protein subcellular localisation prediction is important and well studied. Knowing a protein's localisation helps elucidate its function. Experimental methods for protein localization range from immunolocalization to tagging of proteins using green fluorescent protein (GFP) or beta-glucuronidase (GUS). Such methods are accurate although labor-intensive compared with computational methods. Recently much progress has been made in computational prediction of protein localisation from sequence data. Among algorithms well known to a person skilled in the art are available at the ExPASy Proteomics tools hosted by the Swiss Institute for Bioinformatics, for example, PSort, TargetP, ChloroP, LocTree, Predotar, LipoP, MITOPROT, PATS, PTS1, SignalP, TMHMM, and others. The prediction of the subcellular localisation of an AMT polypeptide as represented by SEQ ID NO: 2 is described in Example 5 of the present application.

Furthermore, AMT polypeptides useful in the methods of the present invention (at least in their native form) typically are capable of transporting ammonium across membranes. Many assays exist to measure such uptake activity, including complementation assays of a yeast strain with defective endogenous ammonium transporters (Ninneman et al. (1994) EMBO J 13: 3464-3471), uptake assays in yeast, *Xenopus oocyctes* (Ludewig et al. (2003) J Biol Chem 278: 45603-45610), plant cells, plant roots (Yuan et al. (2007) Plant Phys 143: 732-744), and whole plants (Hogue et al. (2006) Functional Plant Biology 33: 153-163).

The present invention is illustrated by transforming plants with the nucleic acid sequence represented by SEQ ID NO: 3 (comprised in SEQ ID NO: 1), encoding the AMT polypeptide sequence of SEQ ID NO: 4 (comprised in SEQ ID NO: 2). However, performance of the invention is not restricted to these sequences; the methods of the invention may advantageously be performed using any nucleic acid sequence encoding an AMT polypeptide as defined herein.

Examples of nucleic acid sequences encoding AMT polypeptides are given in Table A of Example 1 herein. Such nucleic acid sequences are useful in performing the methods of the invention. The polypeptide sequences given in Table A of Example 1 are example sequences of orthologues and paralogues of the AMT polypeptide represented by SEQ ID NO: 2 or by SEQ ID NO: 4, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Phaeoactylum tricornutum* sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants may also be useful in practicing the methods of the invention. Examples of such variants include nucleic acid sequences encoding homologues and derivatives of any one of the polypeptide sequences given in Table A of Example 1, the terms "homologue" and "derivative" being as defined herein. Also useful in the methods of the invention are nucleic acid sequences encoding homologues and derivatives of orthologues or paralogues of any one of the polypeptide sequences given in Table A of Example 1. Homologues and derivatives useful in the methods of the present invention have substantially the same biological and functional activity as the unmodified protein from which they are derived.

Further nucleic acid variants useful in practicing the methods of the invention include portions of nucleic acid sequences encoding AMT polypeptides, nucleic acid sequences hybridising to nucleic acid sequences encoding AMT polypeptides, splice variants of nucleic acid sequences encoding AMT polypeptides, allelic variants of nucleic acid sequences encoding AMT polypeptides and variants of nucleic acid sequences encoding AMT polypeptides obtained by gene shuffling. The terms hybridising sequence, splice variant, allelic variant and gene shuffling are as described herein.

Nucleic acid sequences encoding AMT polypeptides need not be full-length nucleic acid sequences, since performance of the methods of the invention does not rely on the use of full-length nucleic acid sequences. According to the present invention, there is provided a method for increasing yield-related traits, in plants, comprising introducing and expressing in a plant a portion of any one of the nucleic acid sequences given in Table A of Example 1, or a portion of a nucleic acid sequence encoding an orthologue, paralogue or homologue of any of the polypeptide sequences given in Table A of Example 1.

A portion of a nucleic acid sequence may be prepared, for example, by making one or more deletions to the nucleic acid sequence. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode an AMT polypeptide as defined herein, and have substantially the same biological activity as the polypeptide sequences given in Table A of Example 1. Preferably, the portion is a portion of any one of the nucleic acid sequences given in Table A of Example 1, or is a portion of a nucleic acid sequence encoding an orthologue or paralogue of any one of the polypeptide sequences given in Table A of Example 1. Preferably the portion is, in increasing order of preference at least 400, 450, 500, 550, 600, 650, 700, 750, 800, 850, 900, 950, 1000, 1050, 1100, 1150, 1200, 1250, 1300, 1350, 1380 or more consecutive nucleotides in length, the consecutive nucleotides being of any one of the nucleic acid sequences given in Table A of Example 1, or of a nucleic acid sequence encoding an orthologue or paralogue of any one of the polypeptide sequences given in Table A of Example 1. Preferably, the portion is a portion of a nucleic sequence encoding a polypeptide sequence polypeptide comprising a domain having in increasing order of preference at least 50%, 55%, 60%, 65%, 70%, 75%, 80%, 85%, 90%, 95%, 98%, 99% or more amino acid sequence identity to a Conserved Domain (CD) as represented by SEQ ID NO: 33. More preferably, the portion is a portion of the nucleic acid sequence of SEQ ID NO: 1. Most preferably, the portion is as represented by SEQ ID NO: 3.

Another nucleic acid sequence variant useful in the methods of the invention is a nucleic acid sequence capable of hybridising, under reduced stringency conditions, preferably under stringent conditions, with a nucleic acid sequence encoding an AMT polypeptide as defined herein, or with a portion as defined herein.

According to the present invention, there is provided a method for increasing yield-related traits in plants, comprising introducing and expressing in a plant a nucleic acid sequence capable of hybridizing to any one of the nucleic acid sequences given in Table A of Example 1, or comprising introducing and expressing in a plant a nucleic acid sequence capable of hybridising to a nucleic acid sequence encoding an orthologue, paralogue or homologue of any of the nucleic acid sequences given in Table A of Example 1.

Hybridising sequences useful in the methods of the invention encode an AMT polypeptide as defined herein, and have substantially the same biological activity as the polypeptide sequences given in Table A of Example 1. Preferably, the hybridising sequence is capable of hybridising to any one of the nucleic acid sequences given in Table A of Example 1, or to a portion of any of these sequences, a portion being as defined above, or wherein the hybridising sequence is capable of hybridising to a nucleic acid sequence encoding an orthologue or paralogue of any one of the polypeptide sequences given in Table A of Example 1. Preferably, the hybridising sequence is capable of hybridising to a nucleic acid sequence encoding a polypeptide sequence comprising a domain having in increasing order of preference at least 50%, 55%, 60%, 65%, 70%, 75%, 80%, 85%, 90%, 95%, 98%, 99% or more amino acid sequence identity to a Conserved Domain (CD) as represented by SEQ ID NO: 33. Most preferably, the hybridising sequence is capable of hybridising to a nucleic acid sequence as represented by SEQ ID NO: 1 or to a portion thereof.

Another nucleic acid sequence variant useful in the methods of the invention is a splice variant encoding an AMT polypeptide as defined hereinabove, a splice variant being as defined herein.

According to the present invention, there is provided a method for increasing yield-related traits, comprising introducing and expressing in a plant a splice variant of any one of the nucleic acid sequences given in Table A of Example 1, or a splice variant of a nucleic acid sequence encoding an orthologue, paralogue or homologue of any of the polypeptide sequences given in Table A of Example 1.

Preferred splice variants are splice variants of a nucleic acid sequence represented by SEQ ID NO: 1, or a splice variant of a nucleic acid sequence encoding an orthologue or paralogue of SEQ ID NO: 2. Preferably, the splice variant is a splice variant of a nucleic acid sequence encoding a polypeptide sequence comprising a domain having in increasing order of preference at least 50%, 55%, 60%, 65%, 70%, 75%, 80%, 85%, 90%, 95%, 98%, 99% or more amino acid sequence identity to a Conserved Domain (CD) as represented by SEQ ID NO: 33.

Another nucleic acid sequence variant useful in performing the methods of the invention is an allelic variant of a nucleic acid sequence encoding an AMT polypeptide as defined hereinabove, an allelic variant being as defined herein.

According to the present invention, there is provided a method for increasing yield-related traits, comprising introducing and expressing in a plant an allelic variant of any one of the nucleic acid sequences given in Table A of Example 1, or comprising introducing and expressing in a plant an allelic variant of a nucleic acid sequence encoding an orthologue, paralogue or homologue of any of the polypeptide sequences given in Table A of Example 1.

The allelic variants useful in the methods of the present invention have substantially the same biological activity as the AMT polypeptide of SEQ ID NO: 2 and any of the polypeptide sequences depicted in Table A of Example 1. Allelic variants exist in nature, and encompassed within the methods of the present invention is the use of these natural alleles. Preferably, the allelic variant is an allelic variant of SEQ ID NO: 1 or an allelic variant of a nucleic acid sequence encoding an orthologue or paralogue of SEQ ID NO: 2. Preferably, the allelic variant is an allelic variant of a polypeptide sequence comprising a domain having in increasing order of preference at least 50%, 55%, 60%, 65%, 70%, 75%, 80%, 85%, 90%, 95%, 98%, 99%, or more amino acid sequence identity to a Conserved Domain (CD) as represented by SEQ ID NO: 33.

Gene shuffling or directed evolution may also be used to generate variants of nucleic acid sequences encoding AMT polypeptides as defined above, the term "gene shuffling" being as defined herein.

According to the present invention, there is provided a method for increasing yield-related traits, comprising introducing and expressing in a plant a variant of any one of the nucleic acid sequences given in Table A of Example 1, or comprising introducing and expressing in a plant a variant of a nucleic acid sequence encoding an orthologue, paralogue or homologue of any of the polypeptide sequences given in Table A of Example 1, which variant nucleic acid sequence is obtained by gene shuffling.

Preferably, the variant nucleic acid sequence obtained by gene shuffling encodes a polypeptide sequence comprising a domain having in increasing order of preference at least 50%, 55%, 60%, 65%, 70%, 75%, 80%, 85%, 90%, 95%, 98%, 99% or more amino acid sequence identity to a Conserved Domain (CD) as represented by SEQ ID NO: 33.

Furthermore, nucleic acid sequence variants may also be obtained by site-directed mutagenesis. Several methods are available to achieve site-directed mutagenesis, the most common being PCR based methods (Current Protocols in Molecular Biology. Wiley Eds).

Nucleic acid sequences encoding AMT polypeptides may be derived from any natural or artificial source. The nucleic acid sequence may be modified from its native form in composition and/or genomic environment through deliberate human manipulation. The nucleic acid sequence encoding an AMT polypeptide is from the Eukaryota domain, preferably from the Chromalveolata kingdom, further preferably from the Heterokontophyta phylum. More preferably, the nucleic acid sequence encoding an AMT polypeptide is from the Bacillariophyceae (diatoms) class, and for example, from the following orders: Achnanthales, Bacillariales, Centrales (such as *Thalassiosira pseudonana*), Cymbellales, Eunotiales, Mastogloiales, Naviculales, Pennales (such as *Pheaodactylum tricornutum*), Rhopalodiales, Surirellales, or Thalassiophysales. Most preferably, the nucleic acid sequence is encoding an AMT polypeptide is from *Pheaodactylum tricornutum*.

Performance of the methods of the invention gives plants having increased yield-related traits relative to control plants. The terms "yield" and "seed yield" are described in more detail in the "definitions" section herein.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield-related traits of plants relative to control plants, which method comprises increasing expression in a plant of a nucleic acid sequence encoding an AMT polypeptide as defined herein.

Since the transgenic plants according to the present invention have increased yield-related traits, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect increased (early) vigour. The increase in growth rate may alter the harvest cycle of a plant allowing plants to be sown later and/or harvested sooner than would otherwise be possible (a similar effect may be obtained with earlier flowering time; delayed flowering is usually not a desired trait in crops). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of corn plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises increasing expression in a plant of a nucleic acid sequence encoding an AMT polypeptide as defined herein.

Increased yield-related traits occur whether the plant is under non-stress conditions or whether the plant is exposed to various stresses compared to control plants grown under comparable conditions. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi, nematodes, and insects. The term “non-stress” conditions as used herein are those environmental conditions that allow optimal growth of plants. Persons skilled in the art are aware of normal soil conditions and climatic conditions for a given location.

Performance of the methods of the invention gives plants grown under non-stress conditions or under mild stress conditions having increased yield-related traits, relative to control plants grown under comparable conditions. Therefore, according to the present invention, there is provided a method for increasing yield-related traits in plants grown under non-stress conditions or under mild stress conditions, which method comprises increasing expression in a plant of a nucleic acid sequence encoding an AMT polypeptide.

Performance of the methods according to the present invention results in plants grown under abiotic stress conditions having increased yield-related traits relative to control plants grown under comparable stress conditions. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of “cross talk” between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signaling pathways and cellular responses, such as the production of stress proteins, up-regulation of anti-oxidants, accumulation of compatible solutes and growth arrest. Since diverse environmental stresses activate similar pathways, the exemplification of the present invention with drought stress should not be seen as a limitation to drought stress, but more as a screen to indicate the involvement of AMT polypeptides as defined above, in increasing yield-related traits relative to control plants grown in comparable stress conditions, in abiotic stresses in general.

The term “abiotic stress” as defined herein is taken to mean any one or more of: water stress (due to drought or excess water), anaerobic stress, salt stress, temperature stress (due to hot, cold or freezing temperatures), chemical toxicity stress and oxidative stress. According to one aspect of the invention, the abiotic stress is an osmotic stress, selected from water stress, salt stress, oxidative stress and ionic stress. Preferably, the water stress is drought stress. The term salt stress is not restricted to common salt (NaCl), but may be any stress caused by one or more of: NaCl, KCl, LiCl, $MgCl_2$, $CaCl_2$, amongst others.

Performance of the methods of the invention gives plants having increased yield-related traits, under abiotic stress conditions relative to control plants grown in comparable stress conditions. Therefore, according to the present invention, there is provided a method for increasing yield-related traits, in plants grown under abiotic stress conditions, which method comprises increasing expression in a plant of a nucleic acid sequence encoding an AMT polypeptide. According to one aspect of the invention, the abiotic stress is an osmotic stress, selected from one or more of the following: water stress, salt stress, oxidative stress and ionic stress.

Another example of abiotic environmental stress is the reduced availability of one or more nutrients that need to be assimilated by the plants for growth and development. Because of the strong influence of nutrition utilization efficiency on plant yield and product quality, a huge amount of fertilizer is poured onto fields to optimize plant growth and quality. Productivity of plants ordinarily is limited by three primary nutrients, phosphorous, potassium and nitrogen, which is usually the rate-limiting element in plant growth of these three. Therefore the major nutritional element required for plant growth is nitrogen (N). It is a constituent of numerous important compounds found in living cells, including amino acids, proteins (enzymes), nucleic acids, and chlorophyll. 1.5% to 2% of plant dry matter is nitrogen and approximately 16% of total plant protein. Thus, nitrogen availability is a major limiting factor for crop plant growth and production (Frink et al. (1999) Proc Natl Acad Sci USA 96(4): 1175-1180), and has as well a major impact on protein accumulation and amino acid composition. Therefore, of great interest are crop plants with increased yield-related traits, when grown under nitrogen-limiting conditions.

Performance of the methods of the invention gives plants grown under conditions of reduced nutrient availability, particularly under conditions of reduced nitrogen availability, having increased yield-related traits relative to control plants grown under comparable conditions. Therefore, according to the present invention, there is provided a method for increasing yield-related traits in plants grown under conditions of reduced nutrient availability, preferably reduced nitrogen availability, which method comprises increasing expression in a plant of a nucleic acid sequence encoding an AMT polypeptide. Reduced nutrient availability may result from a deficiency or excess of nutrients such as nitrogen, phosphates and other phosphorous-containing compounds, potassium, calcium, cadmium, magnesium, manganese, iron and boron, amongst others. Preferably, reduced nutrient availability is reduced nitrogen availability.

The present invention encompasses plants or parts thereof (including seeds) or cells thereof obtainable by the methods according to the present invention. The plants or parts thereof or cells thereof comprise a nucleic acid transgene encoding an AMT polypeptide as defined above.

The invention also provides genetic constructs and vectors to facilitate introduction and/or increased expression in plants of nucleic acid sequences encoding AMT polypeptides as defined herein. The gene constructs may be inserted into vectors, which may be commercially available, suitable for transforming into plants and for expression of the gene of interest in the transformed cells. The invention also provides use of a gene construct as defined herein in the methods of the invention.

More specifically, the present invention provides a construct comprising:

(a) a nucleic acid sequence encoding an AMT polypeptide as defined above;
(b) one or more control sequences capable of increasing expression of the nucleic acid sequence of (a); and optionally
(c) a transcription termination sequence.

Preferably, the nucleic acid sequence encoding an AMT polypeptide is as defined above. The term "control sequence" and "termination sequence" are as defined herein.

Preferably, one of the control sequences of a construct is a constitutive promoter isolated from a plant genome. An example of a plant constitutive promoter is a GOS2 promoter, preferably a rice GOS2 promoter, more preferably a GOS2 promoter as represented by SEQ ID NO: 34.

Plants are transformed with a vector comprising any of the nucleic acid sequences described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to increase expression of the nucleic acid sequence. A constitutive promoter is particularly useful in the methods, preferably a constitutive promoter isolated from a plant genome. The plant constitutive promoter drives expression of a coding sequence at a level that is in all instances below that obtained under the control of a 35S CaMV viral promoter.

Other organ-specific promoters, for example for preferred expression in leaves, stems, tubers, meristems, seeds (embryo and/or endosperm), are useful in performing the methods of the invention. See the "Definitions" section herein for definitions of the various promoter types.

It should be clear that the applicability of the present invention is not restricted to a nucleic acid sequence encoding the AMT polypeptide, as represented by SEQ ID NO: 1 or by SEQ ID N: 3, nor is the applicability of the invention restricted to expression of an AMT polypeptide-encoding nucleic acid sequence when driven by a constitutive promoter.

Optionally, one or more terminator sequences may be used in the construct introduced into a plant. Additional regulatory elements may include transcriptional as well as translational increasers. Those skilled in the art will be aware of terminator and increaser sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, increaser, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection of the successful transfer of the nucleic acid sequences as used in the methods of the invention and/or selection of transgenic plants comprising these nucleic acid sequences, it is advantageous to use marker genes (or reporter genes). Therefore, the genetic construct may optionally comprise a selectable marker gene. Selectable markers are described in more detail in the "definitions" section herein.

It is known that upon stable or transient integration of nucleic acid sequences into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid sequence molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid sequence can be identified for example by selection (for example, cells which have integrated the selectable marker survive whereas the other cells die). The marker genes may be removed or excised from the transgenic cell once they are no longer needed. Techniques for marker gene removal are known in the art, useful techniques are described above in the definitions section.

The invention also provides a method for the production of transgenic plants having increased yield-related traits relative to control plants, comprising introduction and expression in a plant of any nucleic acid sequence encoding an AMT polypeptide as defined hereinabove.

More specifically, the present invention provides a method for the production of transgenic plants having increased yield-related traits relative to control plants, which method comprises:

(i) introducing and expressing in a plant, plant part, or plant cell a nucleic acid sequence encoding an AMT polypeptide, under the control of plant constitutive promoter; and (ii) cultivating the plant cell, plant part or plant under conditions promoting plant growth and development.

The nucleic acid sequence of (i) may be any of the nucleic acid sequences capable of encoding an AMT polypeptide as defined herein.

The nucleic acid sequence may be introduced directly into a plant cell or into the plant itself (including introduction into a tissue, organ or any other part of a plant). According to a preferred feature of the present invention, the nucleic acid sequence is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid sequence encoding an AMT polypeptide as defined hereinabove, operably linked to a plant constitutive promoter. Preferred host cells according to the invention are plant cells. Host plants for the nucleic acid sequences or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants, which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant comprising an isolated nucleic acid sequence encoding an AMT (as defined hereinabove) operably linked to a plant constitutive promoter, such as, but not limited to seeds, leaves, fruits, flowers, stems, rhizomes, tubers and bulbs. The invention furthermore relates to products derived, preferably directly derived, from a harvestable part of such a plant, such as dry pellets or powders, oil, fat and fatty acids, starch or proteins.

Methods for increasing expression of nucleic acid sequences or genes, or gene products, are well documented in the art and examples are provided in the definitions section.

As mentioned above, a preferred method for increasing expression of a nucleic acid sequence encoding an AMT polypeptide is by introducing and expressing in a plant a nucleic acid sequence encoding an AMT polypeptide; however the effects of performing the method, i.e. increasing yield-related traits, may also be achieved using other well known techniques, including but not limited to T-DNA activation tagging, TILLING, homologous recombination. A description of these techniques is provided in the definitions section.

The present invention also encompasses use of nucleic acid sequences encoding AMT polypeptides as described herein and use of these AMT polypeptides in increasing any of the aforementioned yield-related traits in plants, under normal growth conditions, under abiotic stress growth (preferably osmotic stress growth conditions) conditions, and under growth conditions of reduced nutrient availability, preferably under conditions of reduced nitrogen availability.

Nucleic acid sequences encoding AMT polypeptides described herein, or the AMT polypeptides themselves, may find use in breeding programmes in which a DNA marker is identified that may be genetically linked to an AMT polypeptide-encoding gene. The genes/nucleic acid sequences, or the AMT polypeptides themselves may be used to define a molecular marker. This DNA or protein marker may then be used in breeding programmes to select plants having increased yield-related traits, as defined hereinabove in the methods of the invention.

Allelic variants of a gene/nucleic acid sequence encoding an AMT polypeptide may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield-related traits. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acid sequences encoding AMT polypeptides may also be used as probes for genetically and physically mapping the genes that they are a part of, and as markers for traits linked to those genes. Such information may be useful in plant breeding in order to develop lines with desired phenotypes. Such use of nucleic acid sequences encoding an AMT polypeptide requires only a nucleic acid sequence of at least 15 nucleotides in length. The nucleic acid sequences encoding an AMT polypeptide may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the nucleic acid sequences encoding an AMT polypeptide. The resulting banding patterns may then be subjected to genetic analyses using computer programs such as MapMaker (Lander et al. (1987) Genomics 1: 174-181) in order to construct a genetic map. In addition, the nucleic acid sequences may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid sequence encoding an AMT polypeptide in the genetic map previously obtained using this population (Botstein et al. (1980) Am. J. Hum. Genet. 32: 314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid sequence probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid sequence probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid sequence amplification-based methods for genetic and physical mapping may be carried out using the nucleic acid sequences. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic acid sequence Res. 18:3671), Radiation Hybrid Mapping (Walter et al. (1997) Nat. Genet. 7:22-28) and Happy Mapping (Dear and Cook (1989) Nucleic acid sequence Res. 17:6795-6807). For these methods, the sequence of a nucleic acid sequence is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield-related traits, as described hereinbefore. These traits may also be combined with other economically advantageous traits, such as further yield-increasing traits, tolerance to abiotic and biotic stresses, tolerance to herbicides, insectides, traits modifying various architectural features and/or biochemical and/or physiological features.

DESCRIPTION OF FIGURES

The present invention will now be described with reference to the following figures in which:

FIG. 5 details examples of sequences useful in performing the methods according to the present invention.

EXAMPLES

Figure 1:
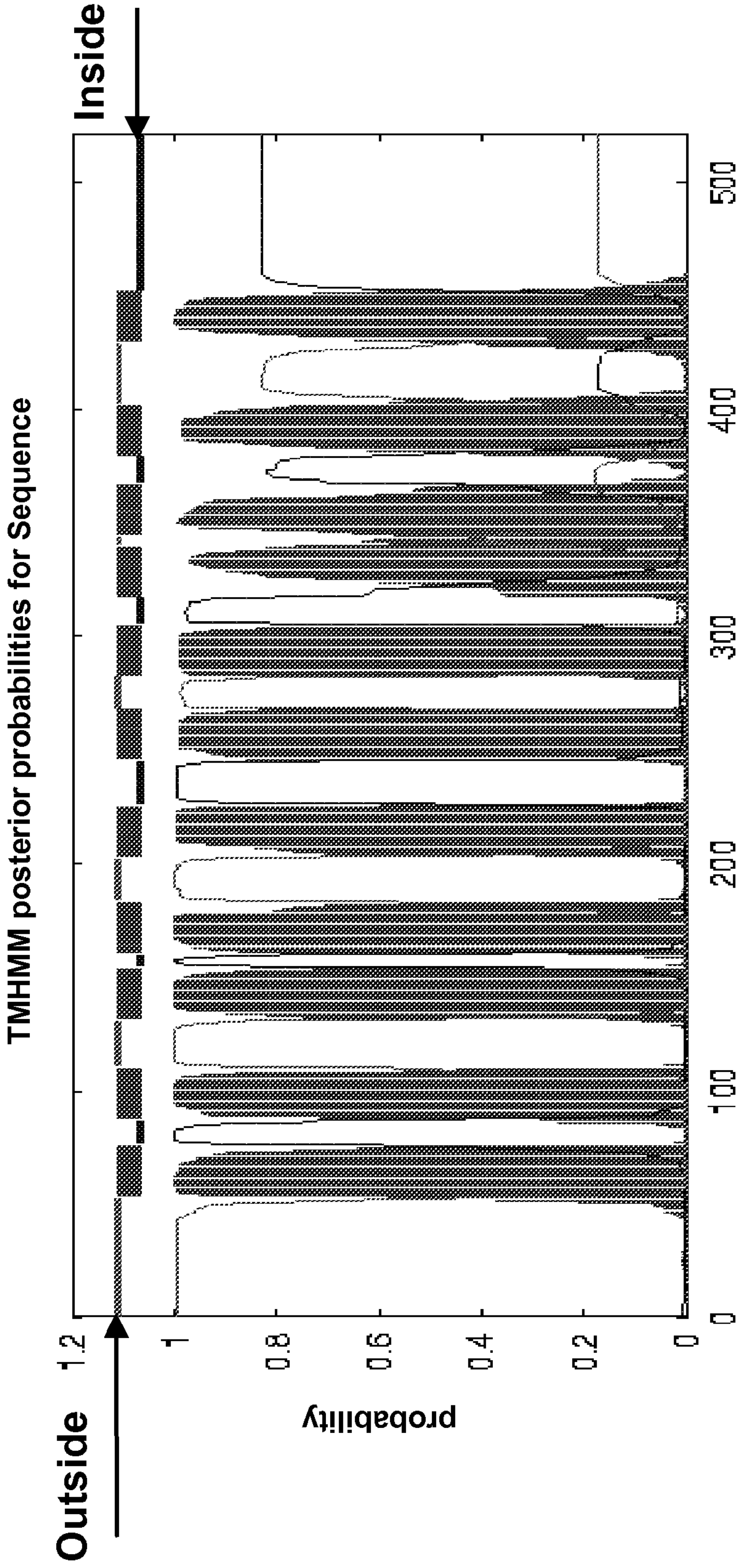
FIG. 1 represents the graphical output of the algorithm TMHMM2.0 for SEQ ID NO: 2. From the algorithm prediction, the N-terminus of the polypeptide is located on the outer side of the membrane (extracytosolic), followed by 11 transmembrane spanning helices, the C-terminus of the polypeptide of the polypeptide being located on the inner side of the membrane (cytosolic).
Figure 2:
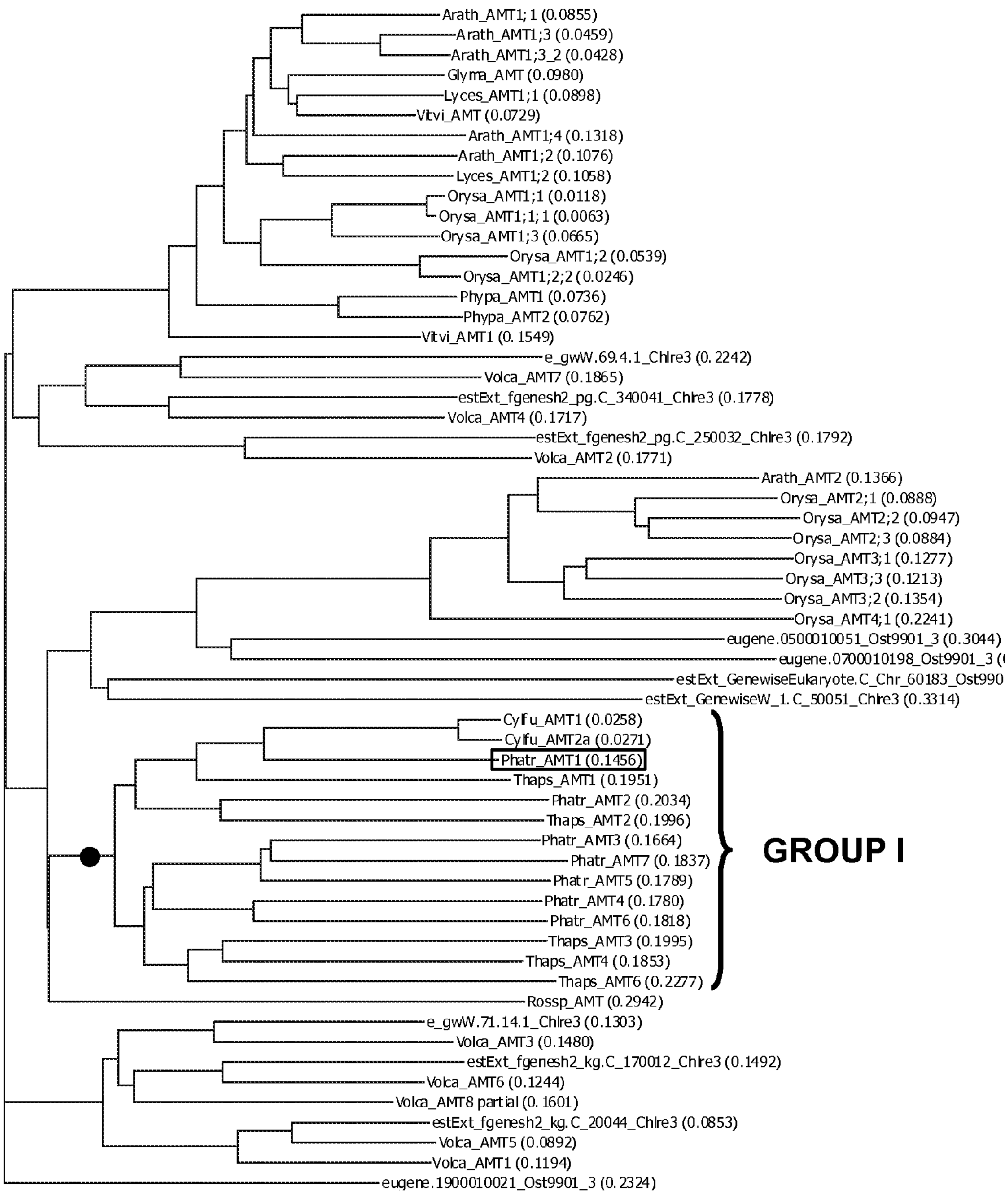
FIG. 2 shows a phylogenetic tree of AMT polypeptides from various source organisms: Group I represents the cluster of polypeptide sequences useful in performing the methods of the invention, as delimited by the bracket. The circle represents the branching point in the tree between the polypeptides useful in performing the methods of the invention, and the other AMT polypeptides.

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid sequence or polypeptide sequences to sequence databases and by calculating the statistical significance of matches. For example, the polypeptide encoded by the nucleic acid sequence of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid sequence (or polypeptide) sequences over a particular length. In some instances, the default parameters may be adjusted to modify the stringency of the search. For example the E-value may be increased to show less stringent matches. This way, short nearly exact matches may be identified.

Table A provides a list of nucleic acid sequences related to the nucleic acid sequence used in the methods of the present invention.

TABLE A:

Examples of AMT polypeptide sequences, and encoding nucleic acid sequences:

| Name | Source organism | Public database accession number | Nucleic acid sequence SEQ ID NO: | Polypeptide sequence SEQ ID NO: |
|---|---|---|---|---|
| Phatr_AMT1_FL | Phaeodactylum tricornutum | jgi_Phatr2_20754_estExt_gwp_gw1.C_chr_100028 | 1 | 2 |
| Phatr_AMT1_partial | Phaeodactylum tricornutum | jgi_Phatr2_20754_estExt_gwp_gw1.C_chr_100028 | 3 | 4 |
| Phatr_AMT2 | Phaeodactylum tricornutum | jgi_Phatr2_22927_estExt_gwp_gw1.C_chr_200095 | 5 | 6 |
| Phatr_AMT3 | Phaeodactylum tricornutum | jgi_Phatr2_20954_estExt_gwp_gw1.C_chr_110018 | 7 | 8 |
| Phatr_AMT4 | Phaeodactylum tricornutum | jgi_Phatr2_34491_fgeneshi_pg.C_chr_5000291 | 9 | 10 |
| Phatr_AMT5 | Phaeodactylum tricornutum | jgi_Phatr2_33710_fgeneshi_pg.C_chr_4000065 | 11 | 12 |
| Phatr_AMT6 | Phaeodactylum tricornutum | jgi_Phatr2_53344_phatri_ua_pm.chr_10000004 | 13 | 14 |

TABLE A:-continued

Examples of AMT polypeptide sequences, and encoding nucleic acid sequences:

| Name | Source organism | Public database accession number | Nucleic acid sequence SEQ ID NO: | Polypeptide sequence SEQ ID NO: |
|---|---|---|---|---|
| Phatr_AMT7 | Phaeodactylum tricornutum | jgi_Phatr2_43458_e stExt_fgeneshl_pg. C_chr_20211 | 15 | 16 |
| Cylfu_AMT1 | Cylindrotheca fusiformis | AF360394 | 17 | 18 |
| Cylfu_AMT1 variant | Cylindrotheca fusiformis | AY651852 | 19 | 20 |
| Cylfu_AMT2a | Cylindrotheca fusiformis | AY651853 | 21 | 22 |
| Thaps_AMT1 | Thalassiosira pseudonana | jgi_Thaps3_258067 _thapsl_ua_pm.chr _7000085 | 23 | 24 |
| Thaps_AMT2 | Thalassiosira pseudonana | jgi_Thaps3_261441 _thaps1_ua_kg.chr_ 2000265 | 25 | 26 |
| Thaps_AMT3 | Thalassiosira pseudonana | jgi_Thaps3_7968_fg 27 eneshi_pg.C_chr_9 000136 | 27 | 28 |
| Thaps_AMT4 | Thalassiosira pseudonana | jgi_Thaps3_2305_fg 29 eneshi_pg.C_chr_2 000260 | 29 | 30 |
| Thaps_AMT6 | Thalassiosira pseudonana | jgi_Thaps3_257021 _thapsl_ua_pm.chr _4000455 | 31 | 32 |

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid sequence or polypeptide sequence of interest. On other instances, special nucleic acid sequence databases have been created for particular organisms, such as by the Joint Genome Institute, for example for *Thalassiosira pseudonana* and *Phaeoactylum tricornutum.*

Example 2

Alignment of AMT Polypeptide Sequences

Figures 3, 4:
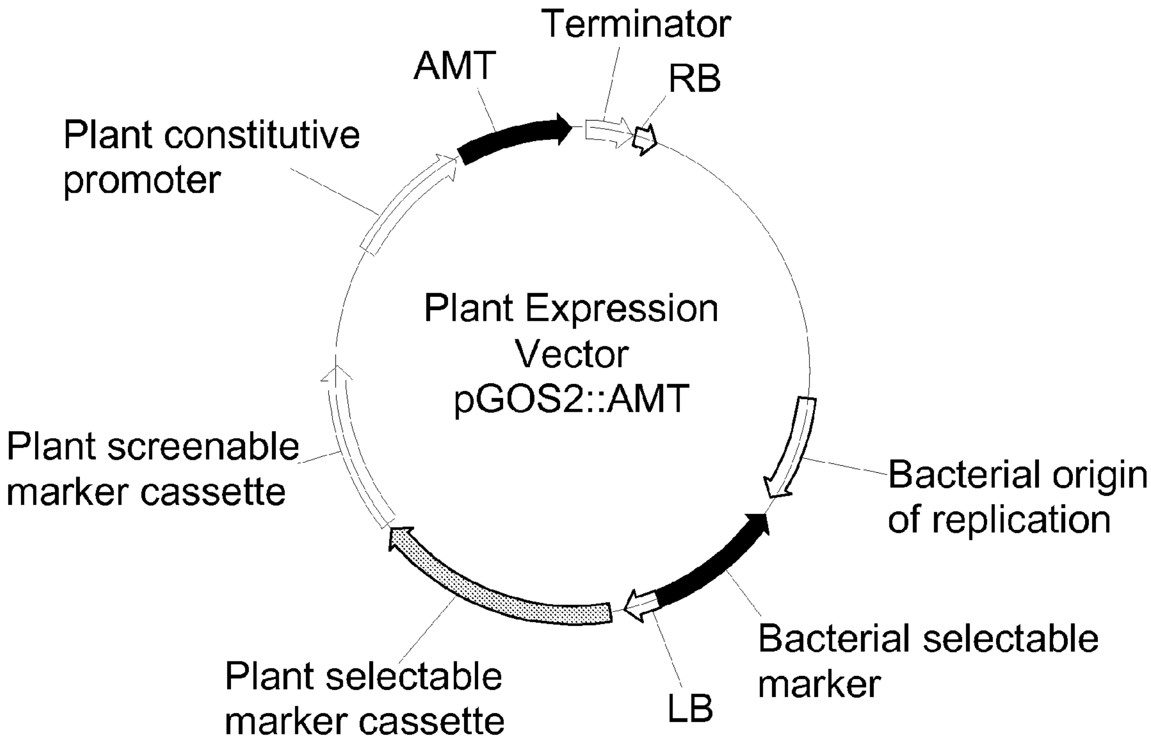
FIG. 3 shows an AlignX (from Vector NTI 10.3, Invitrogen Corporation) multiple sequence alignment of the AMT polypeptides from Table A. The beginning and the end of the Conserved Domain (CD), for example as represented by SEQ ID NO: 33, is shown using brackets, and marked by X's under the consensus sequence. A conserved G (Gly) residue involved in proper AMT function (Ludewig et al. (2003) J Biol Chem 278: 45603-10), is boxed. Phatr_AMT1: SEQ ID NO: 2; Cylfu_AMT1: SEQ ID NO: 18; Cylfu_AMT2a: SEQ ID NO: 22; Thaps_AMT1: SEQ ID NO: 24; Phatr_AMT2: SEQ ID NO: 6; Thaps_AMT2: SEQ ID NO: 26; Phatr_AMT4: SEQ ID NO: 10; Phatr_AMT6: SEQ ID NO: 14; Phatr_AMT3: SEQ ID NO: 8; Phatr_AMT7: SEQ ID NO: 16; Phatr_AMT5: SEQ ID NO: 12; Thaps_AMT3: SEQ ID NO: 28; Thaps_AMT4: SEQ ID NO: 30; Thaps_AMT6: SEQ ID NO: 32; Consensus: SEQ ID NO: 37; and PS01219: SEQ ID NO: 38.
FIG. 4 shows the binary vector for increased expression in *Oryza sativa* of a nucleic acid sequence encoding an AMT polypeptide under the control of a GOS2 promoter (pGOS2) from rice.

Multiple sequence alignment of all the AMT polypeptide sequences in Table A was performed using the AlignX algorithm (from Vector NTI 10.3, Invitrogen Corporation). Results of the alignment are shown in FIG. 3 of the present application. The beginning and the end of the Conserved Domain (CD), for example as represented by SEQ ID NO: 33, is shown using brackets, and marked by X's under the consensus sequence. A conserved G (Gly) residue involved in proper AMT function (Ludewig et al. (2003) J Biol Chem 278: 45603-10), is boxed.

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B for the global similarity and identity over the full length of the polypeptide sequences (excluding the partial polypeptide sequences).

The same analysis was done between the Conserved Domain (CD) as represented by SEQ ID NO: 33 (and comprised in SEQ ID NO: 2 and in SEQ ID NO: 4), and the Conserved Domain of the polypeptides of Table A (as highlighted in FIG. 3), and results are shown in Table B1.

TABLE B

| MatGAT results for global similarity and identity over the full length of the polypeptide sequences of Table A. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. Cylfu_AMT1 | | 94.7 | 68.9 | 50.5 | 46.9 | 49.5 | 44.6 | 47.4 | 45.9 | 61.4 | 50.6 | 46.3 | 49.5 | 44.0 |
| 2. Cylfu_AMT2a | 97.7 | | 68.8 | 50.1 | 46.7 | 50.8 | 44.8 | 46.5 | 45.4 | 60.5 | 50.3 | 46.0 | 49.0 | 44.0 |
| 3. Phatr_AMT1 SEQ ID NO: 2 | 81.8 | 82.7 | | 52.6 | 46.7 | 48.9 | 47.5 | 48.9 | 46.8 | 61.7 | 52.8 | 46.4 | 50.0 | 44.3 |
| 4. Phatr_AMT2 | 64.9 | 65.7 | 65.9 | | 46.8 | 44.0 | 45.5 | 47.8 | 45.1 | 49.7 | 59.7 | 45.3 | 46.2 | 43.7 |
| 5. Phatr_AMT3 | 62.9 | 63.1 | 61.0 | 60.6 | | 46.9 | 63.3 | 52.2 | 61.9 | 48.4 | 46.7 | 49.4 | 50.3 | 48.4 |
| 6. Phatr_AMT4 | 66.5 | 67.3 | 67.0 | 59.9 | 63.3 | | 47.0 | 57.8 | 45.7 | 47.3 | 45.5 | 46.7 | 52.0 | 44.2 |
| 7. Phatr_AMT5 | 61.0 | 60.7 | 60.5 | 61.0 | 77.8 | 62.3 | | 50.0 | 59.4 | 44.7 | 45.2 | 48.5 | 49.6 | 47.5 |
| 8. Phatr_AMT6 | 61.2 | 61.6 | 64.3 | 62.6 | 66.5 | 73.5 | 64.4 | | 49.3 | 47.8 | 50.9 | 48.4 | 49.6 | 46.2 |
| 9. Phatr_AMT7 | 64.7 | 64.4 | 63.1 | 63.3 | 75.0 | 64.6 | 74.1 | 65.7 | | 46.2 | 44.6 | 46.4 | 50.4 | 45.4 |
| 10. Thaps_AMT1 | 73.1 | 72.9 | 73.3 | 62.7 | 62.2 | 64.4 | 60.3 | 64.3 | 63.6 | | 50.5 | 46.0 | 48.2 | 44.0 |
| 11. Thaps_AMT2 | 66.5 | 66.2 | 67.1 | 72.0 | 60.8 | 62.6 | 58.9 | 67.0 | 63.8 | 65.2 | | 45.5 | 46.4 | 42.8 |
| 12. Thaps_AMT3 | 63.0 | 61.5 | 59.9 | 58.7 | 64.4 | 62.6 | 65.3 | 63.5 | 63.7 | 60.6 | 59.9 | | 56.8 | 50.4 |
| 13. Thaps_AMT4 | 66.1 | 65.6 | 64.7 | 59.9 | 64.7 | 66.7 | 64.2 | 62.8 | 65.9 | 63.7 | 60.6 | 71.5 | | 51.5 |
| 14. Thaps_AMT6 | 57.9 | 57.6 | 57.0 | 57.2 | 62.2 | 58.7 | 61.9 | 61.1 | 59.9 | 57.6 | 56.0 | 63.4 | 60.6 | |

TABLE B.1

| MatGAT results for global similarity and identity over the Conserved Domain of the polypeptide sequences of Table A. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 1. CD_Cylfu_AMT1 | | 95.6 | 74.7 | 56.4 | 56.7 | 57.5 | 55.1 | 56.9 | 53.0 | 68.0 | 56.9 | 57.1 | 56.3 | 55.2 |
| 2. CD_Cylfu_AMT2a | 98.3 | | 74.7 | 56.0 | 56.2 | 58.7 | 54.9 | 56.2 | 52.5 | 67.2 | 57.1 | 56.6 | 56.3 | 55.2 |
| 3. CD_Phatr_AMT1 SEQ ID NO: 2 | 86.2 | 87.2 | | 60.3 | 57.5 | 58.4 | 56.6 | 58.7 | 55.1 | 69.0 | 59.3 | 56.7 | 58.1 | 57.4 |
| 4. CD_Phatr_AMT2 | 72.5 | 72.8 | 74.5 | | 55.5 | 54.4 | 52.7 | 56.6 | 53.0 | 57.8 | 68.0 | 54.5 | 55.3 | 54.5 |
| 5. CD_Phatr_AMT3 | 74.3 | 73.8 | 73.1 | 72.4 | | 59.5 | 73.6 | 61.0 | 74.8 | 58.7 | 55.5 | 61.1 | 62.8 | 59.6 |
| 6. CD_Phatr_AMT4 | 74.6 | 75.1 | 73.8 | 70.7 | 76.3 | | 58.9 | 72.6 | 56.3 | 56.9 | 55.3 | 58.5 | 60.9 | 57.6 |
| 7. CD_Phatr_AMT5 | 72.9 | 72.2 | 70.5 | 70.5 | 85.9 | 74.3 | | 59.1 | 70.0 | 53.6 | 53.3 | 60.2 | 60.7 | 58.8 |
| 8. CD_Phatr_AMT6 | 73.1 | 73.1 | 74.5 | 71.8 | 77.4 | 86.4 | 75.3 | | 57.9 | 58.7 | 58.3 | 58.2 | 60.0 | 58.2 |
| 9. CD_Phatr_AMT7 | 73.8 | 73.3 | 72.9 | 69.9 | 87.8 | 74.6 | 84.2 | 75.5 | | 53.9 | 50.1 | 57.7 | 60.6 | 58.1 |
| 10. CD_Thaps_AMT1 | 78.8 | 79.3 | 78.8 | 71.7 | 74.4 | 72.9 | 71.0 | 75.0 | 73.9 | | 56.9 | 57.1 | 56.4 | 55.8 |
| 11. CD_Thaps_AMT2 | 73.3 | 73.8 | 74.3 | 79.2 | 71.4 | 72.4 | 68.3 | 74.8 | 69.4 | 72.4 | | 54.3 | 55.6 | 52.5 |
| 12. CD_Thaps_AMT3 | 74.3 | 73.1 | 72.0 | 68.1 | 76.5 | 74.1 | 76.0 | 74.3 | 75.8 | 72.0 | 68.4 | | 67.2 | 63.7 |
| 13. CD_Thaps_AMT4 | 72.3 | 72.5 | 72.5 | 68.4 | 76.5 | 74.6 | 76.3 | 73.3 | 76.5 | 70.2 | 69.6 | 82.1 | | 64.4 |
| 14. CD_Thaps_AMT6 | 72.4 | 71.9 | 70.5 | 70.2 | 73.8 | 73.8 | 73.1 | 74.1 | 73.8 | 71.4 | 66.8 | 77.0 | 75.3 | |

The percentage identity between the full length polypeptide sequences useful in performing the methods of the invention can be as low as 44% amino acid identity compared to SEQ ID NO: 2.

The percentage identity between the Conserved Domain (CD) as represented by SEQ ID NO: 33 (and comprised in SEQ ID NO: 2 and in SEQ ID NO: 4), and the Conserved Domain of the polypeptides of Table A (as highlighted in FIG. 3) increases to 55% amino acid identity, as shown in Table B1.

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, Panther, ProDom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table C.

TABLE C:

InterPro scan results of the polypeptide sequence as represented by SEQ ID NO: 2

| InterPro accession number and name | Integrated database name | Integrated database accession number | Integrated database accession name |
|---|---|---|---|
| IPR0001905 Ammonium transporter | Panther | PTHR11730 | Ammonium transporter |
| IPR0001905 Ammonium transporter | TIGR | TIGR00836 | Amt: ammonium transporter |
| IPR0001905 Ammonium transporter | Prosite | PS01219 | Ammonium_Transporter |
| IPR010256 Rh-like protein/ammonium transporter | PFAM | F00909 | Ammonium_transporter |
| No IPR integrated | Panther | PTHR11730:SF8 | Ammonium transporter 1 |
| No IPR integrated | tmhmm | | Transmembrane regions |

Example 5

Subcellular Localisation Prediction of the Polypeptide Sequences Useful in Performing the Methods of the Invention Experimental methods for protein localization range from immunolocalization to tagging of proteins using green fluorescent protein (GFP) or beta-glucuronidase (GUS). For example, an AMT transporters from *Arabidopsis thaliana* were localized in the plasma membrane using GFP fusion experiments (Yuan et al. (2003) Plant Cell 19: 2636-2652).

Computational prediction of protein localisation from sequence data was also performed. Among algorithms well known to a person skilled in the art are available at the ExPASy Proteomics tools hosted by the Swiss Institute for Bioinformatics, for example, PSort, TargetP, ChloroP, LocTree, Predotar, LipoP, MITOPROT, PATS, PTS1, SignalP, TMHMM and others.

A transmembrane domain usually denotes a single transmembrane alpha helix of a transmembrane protein. It is called “domain” because an alpha-helix in membrane can be folded independently on the rest of the protein. More broadly, a transmembrane domain is any three-dimensional protein structure which is thermodynamically stable in membrane. This may be a single alpha helix, a stable complex of several transmembrane alpha helices, a transmembrane beta barrel, a beta-helix of gramicidin A, or any other structure.

Transmembrane helices are usually about 20 amino acids in length, although they may be much longer or shorter. TMHMM2.0 is an algorithm that can predict transmembrane spanning helices in proteins. The algorithm is hosted on the server of Technical University of Denmark. Table D below shows the output of TMHMM2.0 using the polypeptide sequence information of SEQ ID NO: 2. From the prediction, the N-terminus of the polypeptide is located on the outer side of the membrane (extracytosolic), followed by 11 transmembrane spanning helices, the C-terminus of the polypeptide of the polypeptide being located on the inner side of the membrane (cytosolic). The same configuration applies to SEQ ID NO: 4, except that the first outside portion is smaller. FIG. 1 is a graphical representation of the output as in Table D.

TABLE D

Output of TMHMM2.0 using the polypeptide sequence information of SEQ ID NO: 2.

| Location | Amino acid coordinates |
|---|---|
| outside | 1-53 |
| TMhelix | 54-76 |
| inside | 77-87 |
| TMhelix | 88-110 |
| outside | 111-131 |
| TMhelix | 132-154 |
| inside | 155-160 |
| TMhelix | 161-183 |
| outside | 184-202 |
| TMhelix | 203-225 |
| inside | 226-245 |
| TMhelix | 246-268 |
| outside | 269-282 |
| TMhelix | 283-305 |
| inside | 306-317 |
| TMhelix | 318-340 |
| outside | 341-344 |
| TMhelix | 345-367 |
| inside | 368-379 |
| TMhelix | 380-402 |
| outside | 403-429 |

TABLE D-continued

Output of TMHMM2.0 using the polypeptide sequence information of SEQ ID NO: 2.

| Location | Amino acid coordinates |
|---|---|
| TMhelix | 430-452 |
| inside | 453-521 |

The predicted subcellular compartment of the AMT polypeptide as represented by SEQ ID NO: 4 using the TMHMM2.0 algorithm is the membrane.

Example 6

Assay Related to the Polypeptide Sequences Useful in Performing the Methods of the Invention AMT polypeptides are capable of transporting ammonium across membranes. Many assays exist to measure such uptake activity, including complementation assays of a yeast strain with defective endogenous ammonium transporters (Ninneman et al. (1994) EMBO J 13: 3464-3471), uptake assays in yeast, *Xenopus oocyctes* (Ludewig et al. (2003) J Biol Chem 278: 45603-45610), plant cells, plant roots (Yuan et al. (2007) Plant Phys 143: 732-744), and whole plants (Hogue et al. (2006) Functional Plant Biology 33: 153-163). A person skilled in the art is well aware of such experimental procedures to measure AMT activity, including AMT activity of an AMT polypeptide as represented by SEQ ID NO: 2.

Example 7

Cloning of Nucleic Acid Sequence as Represented by SEQ ID NO: 1

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Arabidopsis thaliana* cDNA encoding an AMT polypeptide sequence as represented by SEQ ID NO: 4 was amplified by PCR using as template cDNA synthesized from mRNA extracted from *Phaeoactylum tricornutum* at different stages of multiplication, and under different growth conditions. The following primers, which include the AttB sites for Gateway recombination, were used for PCR amplification:

```
1) Prm09458 (SEQ ID NO: 35, sense):
5'-ggggacaagtttgtacaaaaaagcaggcttaaacaatgatgcaggcc
ggg-3'

2) Prm09459 (SEQ ID NO: 36, reverse,
complementary):
5'-ggggaccactttgtacaagaaagctgggtacacgagcagcaattaaa
cc-3'
```

PCR was performed using Hifi Taq DNA polymerase in standard conditions. A PCR fragment of the expected length (including attB sites) was amplified and purified also using standard methods. The first step of the Gateway procedure, the BP reaction, was then performed, during which the PCR fragment recombined in vivo with the pDONR201 plasmid to produce, according to the Gateway terminology, an "entry clone". Plasmid pDONR201 was purchased from Invitrogen, as part of the Gateway® technology.

Example 8

Expression Vector Construction Using the Nucleic Acid Sequence as Represented by SEQ ID NO: 1

The entry clone comprising SEQ ID NO: 3 was subsequently used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 34) for constitutive expression was located upstream of this Gateway cassette.

After the LR recombination step, the resulting expression vector pGOS2::AMT (FIG. 4) was transformed into *Agrobacterium* strain LBA4044 according to methods well known in the art.

Example 9

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were subcultured on fresh medium 3 days before co-cultivation (to boost cell division activity).

*Agrobacterium* strain LBA4404 containing each individual expression vector was used independently for co-cultivation. *Agrobacterium* was inoculated on AB medium with the appropriate antibiotics and cultured for 3 days at 28° C. The bacteria were then collected and suspended in liquid co-cultivation medium to a density ($OD_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent TO rice transformants were generated for each construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges1996, Chan et al. 1993, Hiei et al. 1994).

Example 10

Phenotypic Evaluation Procedure 10.1 Evaluation Setup

Approximately 35 independent TO rice transformants were generated. The primary transformants were transferred from a tissue culture chamber to a greenhouse for growing and harvest of T1 seed. Six events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

10.2 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

10.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination.

Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed weight per plant was measured by weighing all filled husks harvested from one plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed weight per plant and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of the Phenotypic Evaluation of the Transgenic Rice Plants Expressing the Nucleic Acid Sequence Encoding an AMT Polypeptide as Represented by SEQ ID NO: 2

The results of the evaluation of T2 generation transgenic rice plants expressing the nucleic acid sequence encoding an AMT polypeptide as represented by SEQ ID NO: 2, under the control of the GOS2 promoter for constitutive expression, and grown under normal growth conditions, are presented below.

There was a significant increase in the early vigor, in the aboveground biomass, in root biomass, in the total seed yield per plant, in the seed filling rate, in the number of filled seeds, in the number of flowers per panicle, and in the harvest index of the transgenic plants compared to corresponding nullizygotes (controls), as shown in Table E.

TABLE E:

Results of the evaluation of T2 generation transgenic rice plants expressing the nucleic acid sequence encoding an AMT polypeptide as represented by SEQ ID NO: 2, under the control ofthe GOS2 promoter for constitutive expression.

| Trait | Overall average % increase in 4 events in the T2 generation |
|---|---|
| Early vigor | 39% |
| Aboveground biomass | 16% |
| Root biomass | 4% |
| Total seed yield per plant | 31% |
| Seed filling rate | 12% |
| Number of filled seeds | 31% |
| Number of flowers per panicle | 6% |
| Harvest index | 17% |

Example 12

Examples of Transformation of Other Crops

Corn Transformation

Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Cotton Transformation

Cotton (*Gossypium hirsutum* L.) transformation is performed using *Agrobacterium tumefaciens*, on hypocotyls explants. The commercial cultivars such as Coker 130 or Coker 312 (SeedCo, Lubbock, Tex.) are standard varieties used for transformation, but other varieties can also be used. The seeds are surface sterilized and germinated in the dark. Hypocotyl explants are cut from the germinated seedlings to lengths of about 1-1.5 centimeter. The hypotocyl explant is submersed in the *Agrobacterium tumefaciens* inoculum containing the expression vector, for 5 minutes then co-cultivated for about 48 hours on MS+1.8 mg/l KNO3+2% glucose at 24° C., in the dark. The explants are transferred the same medium containing appropriate bacterial and plant selectable markers (renewed several times), until embryogenic calli is seen. The calli are separated and subcultured until somatic embryos appear. Plantlets derived from the somatic embryos are matured on rooting medium until roots develop. The rooted shoots are transplanted to potting soil in the greenhouse. T1 seeds are produced from plants that exhibit tolerance to the selection agent and that contain a single copy of the T-DNA insert.

Example 13

Examples of Abiotic Stress Screens

Drought Screen

Plants from a selected number of events are grown in potting soil under normal conditions until they approached the heading stage. They are then transferred to a “dry” section where irrigation is withheld. Humidity probes are inserted in randomly chosen pots to monitor the soil water content (SWC). When SWC go below certain thresholds, the plants are automatically re-watered continuously until a normal level is reached again. The plants are then re-transferred to normal conditions. The rest of the cultivation (plant maturation, seed harvest) is the same as for plants not grown under abiotic stress conditions. Growth and yield parameters are recorded as detailed for growth under normal conditions.

Salt Stress Screen

Plants are grown on a substrate made of coco fibers and argex (3 to 1 ratio). A normal nutrient solution is used during the first two weeks after transplanting the plantlets in the greenhouse. After the first two weeks, 25 mM of salt (NaCl) is added to the nutrient solution, until the plants were harvested. Growth and yield parameters are recorded as detailed for growth under normal conditions.

Reduced Nutrient (Nitrogen) Availability Screen

Plants from six events (T2 seeds) are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

The invention claimed is:

1. A method for increasing yield-related traits in a plant relative to a control plant, comprising introducing and expressing in a plant a nucleic acid encoding an ammonium transporter (AMT) polypeptide and optionally selecting for a plant having increased yield-related traits relative to a control plant, wherein said AMT polypeptide comprises an amino acid sequence having at least 95% sequence identity to the amino acid sequence of SEQ ID NO:2 or 4.

2. The method according to claim 1, wherein said nucleic acid encoding an AMT polypeptide comprises:

(a) the nucleotide sequence of SEQ ID NO: 1 or 3; or (b) a nucleotide sequence encoding a polypeptide comprising the amino acid sequence of SEQ ID NO: 2 or 4.

3. The method according to claim 1, wherein said increased yield-related trait is one or more of: increased early vigour, increased aboveground biomass, increased root biomass, increased total seed yield per plant, increased seed filling rate, increased number of filled seeds, or increased harvest index.

4. The method according to claim 1, wherein said nucleic acid is operably linked to a constitutive promoter, a plant constitutive promoter, a GOS2 promoter, or a GOS2 promoter from rice comprising the nucleotide sequence of SEQ ID NO: 34.

5. The method according to claim 1, wherein said nucleic acid encoding an AMT polypeptide is from an organism of the Heterokontophyta phylum, the Bacillariophyceae (diatoms) class, the order of Pennales, or *Phaeodactylum tricornutum*.

6. A plant, part thereof (including seeds), or plant cell obtained by the method according to claim 1, or a progeny of said plant, wherein said plant, part or cell thereof, or said progeny, comprises a transgene comprising said nucleic acid encoding an AMT polypeptide operably linked to a plant constitutive promoter.

7. A construct comprising:

(a) a nucleic acid sequence encoding an AMT polypeptide;

(b) one or more heterologous control sequences capable of driving expression of the nucleic acid sequence of (a); and optionally (c) a transcription termination sequence, wherein said AMT polypeptide comprises an amino acid sequence having at least 95% amino acid sequence identity to the amino acid sequence of SEQ ID NO:2 or 4.

8. The construct according to claim 7, wherein said control sequence is a plant constitutive promoter, a GOS2 promoter, or a GOS2 promoter comprising the nucleotide sequence of SEQ ID NO: 34.

9. A method for making a plant having increased yield-related traits relative to a control plant, comprising introducing the construct according to claim 7 and optionally selecting for a plant having increased yield-related traits relative to a control plant, wherein said increased yield-related traits are one or more of: increased early vigour, increased aboveground biomass, increased root biomass, increased total seed yield per plant, increased seed filling rate, increased number of filled seeds, or increased harvest index.

10. A plant, plant part or plant cell comprising the construct according to claim 7.

11. A method for the production of a transgenic plant having increased yield-related traits relative to a control plant, comprising:

(i) introducing and expressing in a plant, plant part, or plant cell, a nucleic acid encoding an AMT polypeptide under control of a plant constitutive promoter;

(ii) cultivating the plant, plant part, or plant cell under conditions promoting plant growth and development;

(iii) selecting for a transgenic plant having increased yield-related traits relative to a control plant; and (iv) optionally producing a progeny from said transgenic plant, wherein said progeny comprises said nucleic acid and has increased yield-related traits relative to a control plant, wherein said AMT polypeptide comprises an amino acid sequence having at least 95% amino acid sequence identity to the amino acid sequence of SEQ ID NO: 2 or 4.

12. A transgenic plant obtained by the method according to claim 11, wherein said transgenic plant has increased yield-related traits relative to a control plant resulting from increased expression of the nucleic acid encoding an AMT polypeptide, or a transgenic plant cell, transgenic plant part, or transgenic progeny derived from said transgenic plant.

13. The plant according to claim 6, wherein said plant is a crop plant, a monocot or a cereal, or wherein said plant is rice, maize, wheat, barley, millet, rye, triticale, sorghum or oats, or a transgenic plant cell derived from said plant.

14. Harvestable parts of the plant according to claim 13, comprising a transgene comprising said nucleic acid encoding an AMT polypeptide, wherein said harvestable parts are preferably seeds.

15. Products derived from the plant according to claim 13 and/or from harvestable parts of said plant, wherein said products and/or said harvestable parts comprise the nucleic acid of claim 1.

16. The transgenic plant according to claim 12, wherein the increase yield-related traits is one or more of: increased early vigour, increased aboveground biomass, increased root biomass, increased total seed yield per plant, increased seed filling rate, increased number of filled seeds, or increased harvest index.

17. The method according to claim 1, wherein said AMT polypeptide further comprises a domain having at least 50% or more sequence identity to the amino acid sequence of SEQ ID NO: 33.

18. The construct according to claim 7, wherein said AMT polypeptide further comprises a domain having at least 50% or more sequence identity to the amino acid sequence of SEQ ID NO: 33.

19. The construct according to claim 7, wherein said nucleic acid sequence encoding an AMT polypeptide comprises:

(a) the nucleotide sequence of SEQ ID NO: 1 or 3; or (b) a nucleotide sequence encoding a polypeptide comprising the amino acid sequence of SEQ ID NO: 2 or 4.

20. The method according to claim 11, wherein said AMT polypeptide further comprises a domain having at least 50% or more sequence identity to the amino acid sequence of SEQ ID NO: 33.

21. The method according to claim 11, wherein said nucleic acid encoding an AMT polypeptide comprises:

(a) the nucleotide sequence of SEQ ID NO: 1 or 3; or (b) a nucleotide sequence encoding a polypeptide comprising the amino acid sequence of SEQ ID NO: 2 or 4.

* * * * *

UNITED STATES PATENT AND TRADEMARK OFFICE

CERTIFICATE OF CORRECTION

PATENT NO. : 8,704,043 B2
APPLICATION NO. : 12/743388
DATED : April 22, 2014
INVENTOR(S) : Frankard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 631 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 38

<210> SEQ ID NO 1
<211> LENGTH: 1566
<212> TYPE: DNA
<213> ORGANISM: Phaeodactylum tricornutum

<400> SEQUENCE: 1

```
atgtcttttg atttggacgc attctgcact ggcctgacag ccgcgtcgag ctcttctgag     60
caggctgtgt gcgctctgca aacgatcgtg gccggagttt ctaagactgt cggaggtatt    120
gacgcggaag ggattactgc aggtgttgat actttcttcc tcatttttgc gggtgccttg    180
gtcttcatga tgcaggccgg gttcgccatg ctttgtgctg gatccgtccg tcaaaagaat    240
gtaaagaata ttatgctcaa gaacttgttg gatgcctgtg gtggtgctat tggcttctac    300
accgttggtt tcggcttcgc ttatggcggt gacgacacca ccgacaagac cttcattggc    360
aacagctact tcgcgctccg tgattacaca aattatgcag gtttcttctt ccagtttgcg    420
tttgctgcca ctgccgccac gattgttgcc ggtacagttg ctgagcgatg caagatgtcg    480
gcataccttt gctactctct ctttcttacg ggtttcgtct atcccgtcgt tgtacgctct    540
gtctggagct ccaacgggtt cttgtcagcc ttcagtgccg accccttcca aggagttgga    600
accgttgact ttgccggatc aggtgtggtg cacatgactg gaggactcac cgccttgatt    660
gctgccattg ttcttggacc gcgtaagggt cggttctacg atgaggatgg caaccctctg    720
gagacgcccg ccagcttccc agcccactct gtagccctcc agatcctcgg aactttcatc    780
ttgtggttcg gatggtacgg attcaaccct ggttcagccc tgaagattgc taacgccgat    840
tcggccgcaa ccgccgcttt gtgtgccgtc accaccacta tggccgccgc tgccggttgt    900
gtttccgcca tgttcactga ctcgatcatt gacggcatgg cgaccggtga aactacgtac    960
gatctgacca tggccatgaa tggatgcctt gctggtctcg ttgccgtcac tgctggtaca   1020
tctgtcgtca ccccatgggc cgcaatcatt attggagtcg ttggaggttg ggtctacatt   1080
ggtatgtcca agcttttgat caagctcaag attgatgacg ctgtcgatgc catccctgtc   1140
catttcgcca atggtttctg ggtgtccta gccaccggcc ttttcgccaa cggtggattg   1200
atggcaaccg ctgggtacaa ctcggaacac gagggctggt tctacgaatg gggaagtggc   1260
tccggagatg gaagtcttct catctgccag cttgcttgcc tcgcctggat tattggatgg   1320
gtcaccacca ttatgacgcc cttttttatc cttttgaaca tggccggtat gttccgtgtg   1380
gacccgcttg aggaagaagt tggtcttgat atttcccatc accgtggatc tgcttacgat   1440
ctttcgggac ccagcaagga ccatgttgac gagctcatgg aaattcgtgc ctcgaagcac   1500
ggcaaggttg aggttccaaa ggaggttgcg caggctgctg atgacgccgc cgaagagact   1560
gcttaa                                                              1566
```

<210> SEQ ID NO 2
<211> LENGTH: 521
<212> TYPE: PRT
<213> ORGANISM: Phaeodactylum tricornutum

<400> SEQUENCE: 2

```
Met Ser Phe Asp Leu Asp Ala Phe Cys Thr Gly Leu Thr Ala Ala Ser
1               5                   10                  15

Ser Ser Ser Glu Gln Ala Val Cys Ala Leu Gln Thr Ile Val Ala Gly
            20                  25                  30
```

-continued

```
Val Ser Lys Thr Val Gly Gly Ile Asp Ala Glu Gly Ile Thr Ala Gly
        35                  40                  45

Val Asp Thr Phe Phe Leu Ile Phe Ala Gly Ala Leu Val Phe Met Met
    50                  55                  60

Gln Ala Gly Phe Ala Met Leu Cys Ala Gly Ser Val Arg Gln Lys Asn
65                  70                  75                  80

Val Lys Asn Ile Met Leu Lys Asn Leu Leu Asp Ala Cys Gly Gly Ala
                85                  90                  95

Ile Gly Phe Tyr Thr Val Gly Phe Gly Phe Ala Tyr Gly Gly Asp Asp
            100                 105                 110

Thr Thr Asp Lys Thr Phe Ile Gly Asn Ser Tyr Phe Ala Leu Arg Asp
        115                 120                 125

Tyr Thr Asn Tyr Ala Gly Phe Phe Phe Gln Phe Ala Phe Ala Ala Thr
    130                 135                 140

Ala Ala Thr Ile Val Ala Gly Thr Val Ala Glu Arg Cys Lys Met Ser
145                 150                 155                 160

Ala Tyr Leu Cys Tyr Ser Leu Phe Leu Thr Gly Phe Val Tyr Pro Val
                165                 170                 175

Val Val Arg Ser Val Trp Ser Ser Asn Gly Phe Leu Ser Ala Phe Ser
            180                 185                 190

Ala Asp Pro Phe Gln Gly Val Gly Thr Val Asp Phe Ala Gly Ser Gly
        195                 200                 205

Val Val His Met Thr Gly Gly Leu Thr Ala Leu Ile Ala Ala Ile Val
    210                 215                 220

Leu Gly Pro Arg Lys Gly Arg Phe Tyr Asp Glu Asp Gly Asn Pro Leu
225                 230                 235                 240

Glu Thr Pro Ala Ser Phe Pro Ala His Ser Val Ala Leu Gln Ile Leu
                245                 250                 255

Gly Thr Phe Ile Leu Trp Phe Gly Trp Tyr Gly Phe Asn Pro Gly Ser
            260                 265                 270

Ala Leu Lys Ile Ala Asn Ala Asp Ser Ala Ala Thr Ala Ala Leu Cys
        275                 280                 285

Ala Val Thr Thr Thr Met Ala Ala Ala Ala Gly Cys Val Ser Ala Met
    290                 295                 300

Phe Thr Asp Ser Ile Ile Asp Gly Met Ala Thr Gly Glu Thr Thr Tyr
305                 310                 315                 320

Asp Leu Thr Met Ala Met Asn Gly Cys Leu Ala Gly Leu Val Ala Val
                325                 330                 335

Thr Ala Gly Thr Ser Val Val Thr Pro Trp Ala Ala Ile Ile Ile Gly
            340                 345                 350

Val Val Gly Gly Trp Val Tyr Ile Gly Met Ser Lys Leu Leu Ile Lys
        355                 360                 365

Leu Lys Ile Asp Asp Ala Val Asp Ala Ile Pro Val His Phe Ala Asn
    370                 375                 380

Gly Phe Trp Gly Val Leu Ala Thr Gly Leu Phe Ala Asn Gly Gly Leu
385                 390                 395                 400

Met Ala Thr Ala Gly Tyr Asn Ser Glu His Glu Gly Trp Phe Tyr Glu
                405                 410                 415

Trp Gly Ser Gly Ser Gly Asp Gly Ser Leu Leu Ile Cys Gln Leu Ala
            420                 425                 430

Cys Leu Ala Trp Ile Ile Gly Trp Val Thr Thr Ile Met Thr Pro Phe
        435                 440                 445

Phe Ile Leu Leu Asn Met Ala Gly Met Phe Arg Val Asp Pro Leu Glu
    450                 455                 460
```

```
Glu Glu Val Gly Leu Asp Ile Ser His His Arg Gly Ser Ala Tyr Asp
465                 470                 475                 480

Leu Ser Gly Pro Ser Lys Asp His Val Asp Glu Leu Met Glu Ile Arg
                485                 490                 495

Ala Ser Lys His Gly Lys Val Glu Val Pro Lys Glu Val Ala Gln Ala
            500                 505                 510

Ala Asp Asp Ala Ala Glu Glu Thr Ala
        515                 520


<210> SEQ ID NO 3
<211> LENGTH: 1380
<212> TYPE: DNA
<213> ORGANISM: Phaeodactylum tricornutum

<400> SEQUENCE: 3

atgatgcagg ccgggttcgc catgctttgt gctggatccg tccgtcaaaa gaatgtaaag      60

aatattatgc tcaagaactt gttggatgcc tgtggtggtg ctattggctt ctacaccgtt     120

ggtttcggct tcgcttatgg cggtgacgac accagcgaca agaccttcat tggcaacagc     180

tacttcgcgc tccgtgatta cacaaattat gcaggtttct tcttccagtt tgcgtttgct     240

gccactgccg ccacgattgt tgccggtaca gttgctgagc gatgcaagat gtcggcatac     300

ctttgctact ctctctttct tacgggtttc gtctatcccg tcgttgtacg ctctgtctgg     360

agctccaacg ggttcttgtc agccttcagt gccgacccct tccaaggagt tggaaccgtt     420

gactttgccg gatcaggtgt ggtgcacatg actggaggac tcaccgcctt gattgctgcc     480

attgttcttg gaccgcgtaa gggtcggttc tacgatgagg atggcaaccc cctggagacg     540

cccgccagct tcccagccca ctctgtagcc ctccagatcc tcggaacttt catcttgtgg     600

ttcggatggt acggattcaa ccctggttca gccctgaaga ttgctaacgc cgattcggcc     660

acaaccgccg ctttgtgtgc cgtcaccacc actatggccg ccgctgccgg ttgtgtttcc     720

gccatgttca ctgactcgat cattgacggc atggcgaccg gtgaaactac gtacgatctg     780

accatggcca tgaatggatg ccttgctggt ctcgttgccg tcactgctgg tacatctgtc     840

gtcaccccat gggccgcaat cattattgga gtcattggag gttgggtcta cattggtatg     900

tccaagcttt tgataaagct caagattgat gacgctgtcg atgccatccc tgtccatttc     960

gccaacggtt tctggggtgt cctagccacc ggccttttcg ccaacggtgg attgatggca    1020

accgctgggt acaactcgga acacgagggc tggttctacg aatggggaag tggctccgga    1080

gatggaagtc ttctcatctg ccagcttgct tgcctcgcct ggattattgg atgggtcacc    1140

accattatga cgcccttttt tatccttttg aacatggccg gtatgttccg tgtggacccg    1200

cttgaggaag aagttggtct tgatatttcc catcaccgtg gatctgctta cgatctttcg    1260

ggacccagca aggaccatgt tgacgagctc atggaaattc gtgcctcgaa gcacggcaag    1320

gttgaggttc caaaggaggt tgcgcaggct gctgatgacg ccgccgaaga gactgcttaa    1380


<210> SEQ ID NO 4
<211> LENGTH: 459
<212> TYPE: PRT
<213> ORGANISM: Phaeodactylum tricornutum

<400> SEQUENCE: 4

Met Met Gln Ala Gly Phe Ala Met Leu Cys Ala Gly Ser Val Arg Gln
1               5                   10                  15

Lys Asn Val Lys Asn Ile Met Leu Lys Asn Leu Leu Asp Ala Cys Gly
            20                  25                  30
```

-continued

```
Gly Ala Ile Gly Phe Tyr Thr Val Gly Phe Gly Phe Ala Tyr Gly Gly
        35                  40                  45

Asp Asp Thr Ser Asp Lys Thr Phe Ile Gly Asn Ser Tyr Phe Ala Leu
    50                  55                  60

Arg Asp Tyr Thr Asn Tyr Ala Gly Phe Phe Phe Gln Phe Ala Phe Ala
65                  70                  75                  80

Ala Thr Ala Ala Thr Ile Val Ala Gly Thr Val Ala Glu Arg Cys Lys
                85                  90                  95

Met Ser Ala Tyr Leu Cys Tyr Ser Leu Phe Leu Thr Gly Phe Val Tyr
            100                 105                 110

Pro Val Val Val Arg Ser Val Trp Ser Ser Asn Gly Phe Leu Ser Ala
        115                 120                 125

Phe Ser Ala Asp Pro Phe Gln Gly Val Gly Thr Val Asp Phe Ala Gly
    130                 135                 140

Ser Gly Val Val His Met Thr Gly Gly Leu Thr Ala Leu Ile Ala Ala
145                 150                 155                 160

Ile Val Leu Gly Pro Arg Lys Gly Arg Phe Tyr Asp Glu Asp Gly Asn
                165                 170                 175

Pro Leu Glu Thr Pro Ala Ser Phe Pro Ala His Ser Val Ala Leu Gln
            180                 185                 190

Ile Leu Gly Thr Phe Ile Leu Trp Phe Gly Trp Tyr Gly Phe Asn Pro
        195                 200                 205

Gly Ser Ala Leu Lys Ile Ala Asn Ala Asp Ser Ala Thr Thr Ala Ala
    210                 215                 220

Leu Cys Ala Val Thr Thr Thr Met Ala Ala Ala Ala Gly Cys Val Ser
225                 230                 235                 240

Ala Met Phe Thr Asp Ser Ile Ile Asp Gly Met Ala Thr Gly Glu Thr
                245                 250                 255

Thr Tyr Asp Leu Thr Met Ala Met Asn Gly Cys Leu Ala Gly Leu Val
            260                 265                 270

Ala Val Thr Ala Gly Thr Ser Val Val Thr Pro Trp Ala Ala Ile Ile
        275                 280                 285

Ile Gly Val Ile Gly Gly Trp Val Tyr Ile Gly Met Ser Lys Leu Leu
    290                 295                 300

Ile Lys Leu Lys Ile Asp Asp Ala Val Asp Ala Ile Pro Val His Phe
305                 310                 315                 320

Ala Asn Gly Phe Trp Gly Val Leu Ala Thr Gly Leu Phe Ala Asn Gly
                325                 330                 335

Gly Leu Met Ala Thr Ala Gly Tyr Asn Ser Glu His Glu Gly Trp Phe
            340                 345                 350

Tyr Glu Trp Gly Ser Gly Ser Gly Asp Gly Ser Leu Leu Ile Cys Gln
        355                 360                 365

Leu Ala Cys Leu Ala Trp Ile Ile Gly Trp Val Thr Thr Ile Met Thr
    370                 375                 380

Pro Phe Phe Ile Leu Leu Asn Met Ala Gly Met Phe Arg Val Asp Pro
385                 390                 395                 400

Leu Glu Glu Glu Val Gly Leu Asp Ile Ser His His Arg Gly Ser Ala
                405                 410                 415

Tyr Asp Leu Ser Gly Pro Ser Lys Asp His Val Asp Glu Leu Met Glu
            420                 425                 430

Ile Arg Ala Ser Lys His Gly Lys Val Glu Val Pro Lys Glu Val Ala
        435                 440                 445

Gln Ala Ala Asp Asp Ala Ala Glu Glu Thr Ala
```

-continued 450 455

<210> SEQ ID NO 5
<211> LENGTH: 1620
<212> TYPE: DNA
<213> ORGANISM: Phaeodactylum tricornutum

<400> SEQUENCE: 5
atgtcgagta gtgctatcta tcaatcttgc gccggtcaat tcgatagcgg tgagcagctt 60
gatcagcttc tgcagtgcct ctctacggga catgacggcg cgctaagcga tcagaccagc 120
aacctcgcag gaggtatcga tgccttttat cttatctttg ccggggccct tgtctacttc 180
atgcagacag gatttgctat gctctgtgcc ggatccattc gagcgaagaa tgtcaagaat 240
gtgattctct ggaacttgct cgattcatgt ggaggcggtc tcgcgttctg gagtgtaggc 300
tatgcctttg cctacggtgg agacaatgct gggtccaaga catttgttgg taacgcaggc 360
tttttcctcc agggagatga cattcgactg gaaaactggt ttttccaatt tgcctttgct 420
tgtgcccttt cctcaattgt cgctggaacg atcgctgagc gcactcaaat gaaggcctat 480
ttgatgtatt ccgttttttt ggctgggttt gtctatccag ttgtcgccca cgcattttgg 540
tcgagcaacg gattcctctc caacacagcc acagatccat tgtggggatc tggcgccatt 600
gacttggcgg gctctggacc agtccacatg accggaggtg ttacggcttt ggcggcagct 660
ctggttttgg gccctcgcat tggtcgcttc tacgacaagg agggcaatcc tctcgaagag 720
ccagccgaat ttcctcccca ttcggttgcc ttgcagtttc tgggaacgtt ttgtctttgg 780
tttggctggt acggctttaa cccaggttcc gtcttcttca tttcgagtat tgaaaacggt 840
caagttgcgg ctttggtagc cgtcaatacc accctagctg cgtgtgcggg tgccgtcagc 900
gccatgttta cttcaacttt atttgactac tggtacaccg gcttgcacac atacgatttg 960
ggctacacta tgaacggatg tttgacggga ttggtcgcga taacagcggg atgcgcgact 1020
gttgaaacgt gggctgccgt cctgattggt attggcgctg gttggtttta cctgttgggt 1080
tcaaagttgc ttgtctactt ccgtattgac gatgctgtcg acgccattcc cgtgcatatg 1140
gtgggtggcg cctggggtgt gatcgcgacg ggccttttta cgaagggaga actactattg 1200
gccgcctttg gccaggagga acatgttgga tggttctacg agtggggcag tgggagcggt 1260
aactttaccc taatcggaat tcaattgctg tctgtgctgt tcattttcgc ctggactttt 1320
tccgtcatgg gaatttattt ttacgccctt agcttcatgg gttggttgcg catagatccg 1380
ttggaagagg aggttggtat ggatatttcg cgccacaagg gctcggcata cgacatgact 1440
tcagcaaata tggagcaggt acggtcgttg atggacgacc gcagtacgag caatcgaggc 1500
aagctgcgta agtcgtccat cattgagaag ccggccaaaa caggtccgat cgagggagga 1560
actgcctccg gagaatcaga aattaaggag tcggacgtgg aacatgccga gagggtctaa 1620

<210> SEQ ID NO 6
<211> LENGTH: 539
<212> TYPE: PRT
<213> ORGANISM: Phaeodactylum tricornutum

<400> SEQUENCE: 6

Met Ser Ser Ser Ala Ile Tyr Gln Ser Cys Ala Gly Gln Phe Asp Ser
1 5 10 15

Gly Glu Gln Leu Asp Gln Leu Leu Gln Cys Leu Ser Thr Gly His Asp
20 25 30

Gly Ala Leu Ser Asp Gln Thr Ser Asn Leu Ala Gly Gly Ile Asp Ala
35 40 45

```
Phe Tyr Leu Ile Phe Ala Gly Ala Leu Val Tyr Phe Met Gln Thr Gly
    50                  55                  60

Phe Ala Met Leu Cys Ala Gly Ser Ile Arg Ala Lys Asn Val Lys Asn
65                  70                  75                  80

Val Ile Leu Trp Asn Leu Leu Asp Ser Cys Gly Gly Gly Leu Ala Phe
                85                  90                  95

Trp Ser Val Gly Tyr Ala Phe Ala Tyr Gly Gly Asp Asn Ala Gly Ser
            100                 105                 110

Lys Thr Phe Val Gly Asn Ala Gly Phe Phe Leu Gln Gly Asp Asp Ile
        115                 120                 125

Arg Leu Glu Asn Trp Phe Phe Gln Phe Ala Phe Ala Cys Ala Leu Ser
    130                 135                 140

Ser Ile Val Ala Gly Thr Ile Ala Glu Arg Thr Gln Met Lys Ala Tyr
145                 150                 155                 160

Leu Met Tyr Ser Val Phe Leu Ala Gly Phe Val Tyr Pro Val Val Ala
                165                 170                 175

His Ala Phe Trp Ser Ser Asn Gly Phe Leu Ser Asn Thr Ala Thr Asp
            180                 185                 190

Pro Leu Trp Gly Ser Gly Ala Ile Asp Leu Ala Gly Ser Gly Pro Val
        195                 200                 205

His Met Thr Gly Gly Val Thr Ala Leu Ala Ala Ala Leu Val Leu Gly
    210                 215                 220

Pro Arg Ile Gly Arg Phe Tyr Asp Lys Glu Gly Asn Pro Leu Glu Glu
225                 230                 235                 240

Pro Ala Glu Phe Pro Pro His Ser Val Ala Leu Gln Phe Leu Gly Thr
                245                 250                 255

Phe Cys Leu Trp Phe Gly Trp Tyr Gly Phe Asn Pro Gly Ser Val Phe
            260                 265                 270

Phe Ile Ser Ser Ile Glu Asn Gly Gln Val Ala Ala Leu Val Ala Val
        275                 280                 285

Asn Thr Thr Leu Ala Ala Cys Ala Gly Ala Val Ser Ala Met Phe Thr
    290                 295                 300

Ser Thr Leu Phe Asp Tyr Trp Tyr Thr Gly Leu His Thr Tyr Asp Leu
305                 310                 315                 320

Gly Tyr Thr Met Asn Gly Cys Leu Thr Gly Leu Val Ala Ile Thr Ala
                325                 330                 335

Gly Cys Ala Thr Val Glu Thr Trp Ala Ala Val Leu Ile Gly Ile Gly
            340                 345                 350

Ala Gly Trp Phe Tyr Leu Leu Gly Ser Lys Leu Leu Val Tyr Phe Arg
        355                 360                 365

Ile Asp Asp Ala Val Asp Ala Ile Pro Val His Met Val Gly Gly Ala
    370                 375                 380

Trp Gly Val Ile Ala Thr Gly Leu Phe Thr Lys Gly Glu Leu Leu Leu
385                 390                 395                 400

Ala Ala Phe Gly Gln Glu Glu His Val Gly Trp Phe Tyr Glu Trp Gly
                405                 410                 415

Ser Gly Ser Gly Asn Phe Thr Leu Ile Gly Ile Gln Leu Leu Ser Val
            420                 425                 430

Leu Phe Ile Phe Ala Trp Thr Phe Ser Val Met Gly Ile Tyr Phe Tyr
        435                 440                 445

Ala Leu Ser Phe Met Gly Trp Leu Arg Ile Asp Pro Leu Glu Glu Glu
    450                 455                 460

Val Gly Met Asp Ile Ser Arg His Lys Gly Ser Ala Tyr Asp Met Thr
```

-continued

```
465                 470                 475                 480

Ser Ala Asn Met Glu Gln Val Arg Ser Leu Met Asp Asp Arg Ser Thr
                485                 490                 495

Ser Asn Arg Gly Lys Leu Arg Lys Ser Ser Ile Ile Glu Lys Pro Ala
            500                 505                 510

Lys Thr Gly Pro Ile Glu Gly Gly Thr Ala Ser Gly Glu Ser Glu Ile
        515                 520                 525

Lys Glu Ser Asp Val Glu His Ala Glu Arg Val
    530                 535


<210> SEQ ID NO 7
<211> LENGTH: 1695
<212> TYPE: DNA
<213> ORGANISM: Phaeodactylum tricornutum

<400> SEQUENCE: 7

atgaatagcc gtaccttttc ttacaacagc aacgatggga atgagttgtt ggatgcatgc     60

atggcttatc tcggcgctaa cgccacgacg tacgacttgc tcggctgcgt gtctgcgcaa    120

ctcagcaacg aagtcgggag tcgcgaattc tctcgttcgg tgctgctcgt ctacgctgct    180

gcactcgtat tctttatgca agccggcttc gccatgctct gtgccggagc cgtccggaaa    240

aagaacgtgc agaacaccat gctcaagaac ttgttggacg cctgtggagc cgccgtcgcc    300

tttttcatcg tgggctacgc tatagccttt ggaggcatgg aaccggaatc gcccaacaag    360

acatttctcg ggaacaccaa tttcttttta atgggagtgg acgatttggc cttttggttg    420

ttccagtacg ccttttccgc tgcctctgca accatcgtcg cgggaacttt ggccgagcgc    480

tgccaaatgg ttgcctactt gtgttactcc gtaatgttga cgggatgggt ctatccgatt    540

atcgcgcacg cgatttggtc acccaacggt tggctctccg ccagttccgt ggatccgcta    600

tggggtgtcg gcatggtcga tttcgccggc tcgggagtag tgcacatgac tggaggcgtt    660

accgccttgt tcgccactct catactcgga cctcgccgtg gacggtttca cgatgaaacc    720

ggacgccggc tcgacaaacc aaaatccttt cccggacact ccgtggcctt gcagatgctc    780

ggtaccttca ttctctggtt tggttggtat ggattcaatt gcggttcggc gttactcatc    840

gacaagcccg gtgctaacga tattgccgcc ttggcgggcg tcaatacgac actttctgcc    900

ggagtcgctg ggatagttgc actctttgtc aacctctggt acctcgagcg aacaaccgga    960

gaaccttttt ttgatttgac ctacgccatg aacggatccc tttcgggtct cgtggccatc   1020

acaggaggtt gcgctgttct cgagccctgg gcggcagcgg tcactggagt cggtgccggt   1080

atcttgtaca tggttggatc acgaggtttg gtcatgttgc gattggatga cgcggttgac   1140

gcgattcccg ttcattttgt gaacggggcc tggggtctca tgtcggtcgg attgttcgcg   1200

tcaccagcac gcttgctggc cgcgtacgac aacgacgctc atcctggatg gttctattcc   1260

ctacgaaacg gcaaatcgga cgggcgtttg gttggagttc agctggtagg cattgtattt   1320

atcgtgggat gggtcatggt gattatgttg cccttcttca tttggttgga ttggaaggga   1380

tggttccggt cggatccttt ggaagaaatt gtgggattgg acacgtcgta ccacggtggt   1440

ctcgctttgc tgggcgggga cgatgaagtc aaccctgagt acatttccgc gtacaagaag   1500

caaaggaacg aaggtacgct gcggcgtagg cataaaggga caaccagcag tgtcaagacg   1560

ggagaagtag aatcggacga aggcgccgaa cgggtggcgc ccgaagcgac gaagcacaaa   1620

aagattccga tcgctacaac gacagaggtt ttcaatggag gtcaagatac ggatcaaatg   1680

tcctaccacg cctga                                                    1695
```

<210> SEQ ID NO 8
<211> LENGTH: 564
<212> TYPE: PRT
<213> ORGANISM: Phaeodactylum tricornutum

<400> SEQUENCE: 8

```
Met Asn Ser Arg Thr Phe Ser Tyr Asn Ser Asn Asp Gly Asn Glu Leu
1               5                   10                  15

Leu Asp Ala Cys Met Ala Tyr Leu Gly Ala Asn Ala Thr Thr Tyr Asp
            20                  25                  30

Leu Leu Gly Cys Val Ser Ala Gln Leu Ser Asn Glu Val Gly Ser Arg
        35                  40                  45

Glu Phe Ser Arg Ser Val Leu Leu Val Tyr Ala Ala Ala Leu Val Phe
    50                  55                  60

Phe Met Gln Ala Gly Phe Ala Met Leu Cys Ala Gly Ala Val Arg Lys
65                  70                  75                  80

Lys Asn Val Gln Asn Thr Met Leu Lys Asn Leu Leu Asp Ala Cys Gly
                85                  90                  95

Ala Ala Val Ala Phe Phe Ile Val Gly Tyr Ala Ile Ala Phe Gly Gly
            100                 105                 110

Met Glu Pro Glu Ser Pro Asn Lys Thr Phe Leu Gly Asn Thr Asn Phe
        115                 120                 125

Phe Leu Met Gly Val Asp Asp Leu Ala Phe Trp Leu Phe Gln Tyr Ala
    130                 135                 140

Phe Ser Ala Ala Ser Ala Thr Ile Val Ala Gly Thr Leu Ala Glu Arg
145                 150                 155                 160

Cys Gln Met Val Ala Tyr Leu Cys Tyr Ser Val Met Leu Thr Gly Trp
                165                 170                 175

Val Tyr Pro Ile Ile Ala His Ala Ile Trp Ser Pro Asn Gly Trp Leu
            180                 185                 190

Ser Ala Ser Ser Val Asp Pro Leu Trp Gly Val Gly Met Val Asp Phe
        195                 200                 205

Ala Gly Ser Gly Val Val His Met Thr Gly Gly Val Thr Ala Leu Phe
    210                 215                 220

Ala Thr Leu Ile Leu Gly Pro Arg Arg Gly Arg Phe His Asp Glu Thr
225                 230                 235                 240

Gly Arg Arg Leu Asp Lys Pro Lys Ser Phe Pro Gly His Ser Val Ala
                245                 250                 255

Leu Gln Met Leu Gly Thr Phe Ile Leu Trp Phe Gly Trp Tyr Gly Phe
            260                 265                 270

Asn Cys Gly Ser Ala Leu Leu Ile Asp Lys Pro Gly Ala Asn Asp Ile
        275                 280                 285

Ala Ala Leu Ala Gly Val Asn Thr Thr Leu Ser Ala Gly Val Ala Gly
    290                 295                 300

Ile Val Ala Leu Phe Val Asn Leu Trp Tyr Leu Glu Arg Thr Thr Gly
305                 310                 315                 320

Glu Pro Phe Phe Asp Leu Thr Tyr Ala Met Asn Gly Ser Leu Ser Gly
                325                 330                 335

Leu Val Ala Ile Thr Gly Gly Cys Ala Val Leu Glu Pro Trp Ala Ala
            340                 345                 350

Ala Val Thr Gly Val Gly Ala Gly Ile Leu Tyr Met Val Gly Ser Arg
        355                 360                 365

Gly Leu Val Met Leu Arg Leu Asp Asp Ala Val Asp Ala Ile Pro Val
    370                 375                 380
```

```
His Phe Val Asn Gly Ala Trp Gly Leu Met Ser Val Gly Leu Phe Ala
385                 390                 395                 400

Ser Pro Ala Arg Leu Leu Ala Ala Tyr Asp Asn Asp Ala His Pro Gly
                405                 410                 415

Trp Phe Tyr Ser Leu Arg Asn Gly Lys Ser Asp Gly Arg Leu Val Gly
            420                 425                 430

Val Gln Leu Val Gly Ile Val Phe Ile Val Gly Trp Val Met Val Ile
        435                 440                 445

Met Leu Pro Phe Phe Ile Trp Leu Asp Trp Lys Gly Trp Phe Arg Ser
    450                 455                 460

Asp Pro Leu Glu Glu Ile Val Gly Leu Asp Thr Ser Tyr His Gly Gly
465                 470                 475                 480

Leu Ala Leu Leu Gly Gly Asp Asp Glu Val Asn Pro Glu Tyr Ile Ser
                485                 490                 495

Ala Tyr Lys Lys Gln Arg Asn Glu Gly Thr Leu Arg Arg Arg His Lys
            500                 505                 510

Gly Thr Thr Ser Ser Val Lys Thr Gly Glu Val Glu Ser Asp Glu Gly
        515                 520                 525

Ala Glu Arg Val Ala Pro Glu Ala Thr Lys His Lys Lys Ile Pro Ile
    530                 535                 540

Ala Thr Thr Thr Glu Val Phe Asn Gly Gly Gln Asp Thr Asp Gln Met
545                 550                 555                 560

Ser Tyr His Ala
```

<210> SEQ ID NO 9
<211> LENGTH: 1554
<212> TYPE: DNA
<213> ORGANISM: Phaeodactylum tricornutum

<400> SEQUENCE: 9

```
atggacgacg cgagctttat ccaaagcctg gtggaagggt acggtacctc gagcaaccac     60

accaccgtct atggatattg ctccaatgag gcggaaggag agaccaacct tattttgcaa    120

tgtattacgg aggtcatgga gcaaaagcag ctcgaaggag atcgtaacgt gaatcggtgg    180

ctaatgcttt tttccggtgg gctgatcttc ttcatgcaga ctggctttgc gatgctttgc    240

gctggttgcg tgcgcaaaaa gaacgttcaa aatacgatgc ttaaaaatct tttggatgcc    300

tgtggagctg ctctaggctt tttcctacta ggctacgctt ttgcgtttgg cggacaagac    360

gaccgggacg atgttacttt catcggaact tccaactttc taaacaccgg aaaagtcgat    420

atgtccttct ggtttttcca gtttgcattc tcggccactg ccgtgactat cgtcgcagga    480

actttggcag agcgttgcca aatggtagca tacctttgct attccatatt tttgacaggt    540

tttgtgtacc cggttgccgc ccacacaatt tggtctcgca acggcttcct cagcagcaca    600

gcagtagacc cttttcaagg tgtgggagcg attgatttcg ccggatccgg tgtggttcat    660

gtgacgggag gaaccacggc tctcgtcgcc acatatattc ttggagctag aaaaggtcgt    720

ttctacgaca atcgcggtcg ccagctggag acgccaaagt cctttccggg gcattcagtt    780

gctctgcagc tacttggtac attcgtattg tggtttggat ggtacggctt caatcctgga    840

tcagcattgc tgctggccca cacttcggat acgggtttcg tggcatcccg agcggctgtc    900

aatacctcgc tttcagctgc ttccggagcc gtatcggcac tgatgacaaa tatgtttatg    960

gaagagcgtt ccaccggcga atactccttt aacattatca tggccatgaa tggcgcctta   1020

gctggtctag tgtcaattac agcagcttgt ggtaccgtac aaaactgggc agccctttgc   1080

actggatgta ttggaggtct tatctacttg tggggttcca aaacgctggt tcgtttgaaa   1140
```

-continued ttggacgatg ctgttgacgc gattccagtg cacatgtttg caggtggctg gggattgctt 1200
gctgtgggtt tgttaagtga tcctgacctc atgcacattg cctatgggac tggcaatcat 1260
cctggtttat tgtattcttg ggggttaggg gagtttaacg ccatcttgct gagcaatcaa 1320
gtgttggaac tagttttcgt ggcgggatgg gcttttggta ccatgacgcc tttctttttg 1380
ttcatcaatc gtatgggatg gttccggtcg gacagtttgg aggagttggt cggtttggat 1440
gaggcctacc acggaggtaa acatggcggg gaagaagtgg tggaactatc cgctctagaa 1500
ggctttatca aaaacaagat cagacaatcg caaattcggt cgccttacaa ttag 1554

<210> SEQ ID NO 10
<211> LENGTH: 517
<212> TYPE: PRT
<213> ORGANISM: Phaeodactylum tricornutum

<400> SEQUENCE: 10

Met Asp Asp Ala Ser Phe Ile Gln Ser Leu Val Glu Gly Tyr Gly Thr
1 5 10 15

Ser Ser Asn His Thr Thr Val Tyr Gly Tyr Cys Ser Asn Glu Ala Glu
20 25 30

Gly Glu Thr Asn Leu Ile Leu Gln Cys Ile Thr Glu Val Met Glu Gln
35 40 45

Lys Gln Leu Glu Gly Asp Arg Asn Val Asn Arg Trp Leu Met Leu Phe
50 55 60

Ser Gly Gly Leu Ile Phe Phe Met Gln Thr Gly Phe Ala Met Leu Cys
65 70 75 80

Ala Gly Cys Val Arg Lys Lys Asn Val Gln Asn Thr Met Leu Lys Asn
85 90 95

Leu Leu Asp Ala Cys Gly Ala Ala Leu Gly Phe Phe Leu Leu Gly Tyr
100 105 110

Ala Phe Ala Phe Gly Gly Gln Asp Asp Arg Asp Asp Val Thr Phe Ile
115 120 125

Gly Thr Ser Asn Phe Leu Asn Thr Gly Lys Val Asp Met Ser Phe Trp
130 135 140

Phe Phe Gln Phe Ala Phe Ser Ala Thr Ala Val Thr Ile Val Ala Gly
145 150 155 160

Thr Leu Ala Glu Arg Cys Gln Met Val Ala Tyr Leu Cys Tyr Ser Ile
165 170 175

Phe Leu Thr Gly Phe Val Tyr Pro Val Ala Ala His Thr Ile Trp Ser
180 185 190

Arg Asn Gly Phe Leu Ser Ser Thr Ala Val Asp Pro Phe Gln Gly Val
195 200 205

Gly Ala Ile Asp Phe Ala Gly Ser Gly Val Val His Val Thr Gly Gly
210 215 220

Thr Thr Ala Leu Val Ala Thr Tyr Ile Leu Gly Ala Arg Lys Gly Arg
225 230 235 240

Phe Tyr Asp Asn Arg Gly Arg Gln Leu Glu Thr Pro Lys Ser Phe Pro
245 250 255

Gly His Ser Val Ala Leu Gln Leu Leu Gly Thr Phe Val Leu Trp Phe
260 265 270

Gly Trp Tyr Gly Phe Asn Pro Gly Ser Ala Leu Leu Leu Ala His Thr
275 280 285

Ser Asp Thr Gly Phe Val Ala Ser Arg Ala Ala Val Asn Thr Ser Leu
290 295 300

-continued

```
Ser Ala Ala Ser Gly Ala Val Ser Ala Leu Met Thr Asn Met Phe Met
305                 310                 315                 320

Glu Glu Arg Ser Thr Gly Glu Tyr Ser Phe Asn Ile Ile Met Ala Met
                325                 330                 335

Asn Gly Ala Leu Ala Gly Leu Val Ser Ile Thr Ala Ala Cys Gly Thr
            340                 345                 350

Val Gln Asn Trp Ala Ala Leu Cys Thr Gly Cys Ile Gly Gly Leu Ile
        355                 360                 365

Tyr Leu Trp Gly Ser Lys Thr Leu Val Arg Leu Lys Leu Asp Asp Ala
    370                 375                 380

Val Asp Ala Ile Pro Val His Met Phe Ala Gly Gly Trp Gly Leu Leu
385                 390                 395                 400

Ala Val Gly Leu Leu Ser Asp Pro Asp Leu Met His Ile Ala Tyr Gly
                405                 410                 415

Thr Gly Asn His Pro Gly Leu Leu Tyr Ser Trp Gly Leu Gly Glu Phe
            420                 425                 430

Asn Ala Ile Leu Leu Ser Asn Gln Val Leu Glu Leu Val Phe Val Ala
        435                 440                 445

Gly Trp Ala Phe Gly Thr Met Thr Pro Phe Phe Leu Phe Ile Asn Arg
    450                 455                 460

Met Gly Trp Phe Arg Ser Asp Ser Leu Glu Glu Leu Val Gly Leu Asp
465                 470                 475                 480

Glu Ala Tyr His Gly Gly Lys His Gly Gly Glu Glu Val Val Glu Leu
                485                 490                 495

Ser Ala Leu Glu Gly Phe Ile Lys Asn Lys Ile Arg Gln Ser Gln Ile
            500                 505                 510

Arg Ser Pro Tyr Asn
        515


<210> SEQ ID NO 11
<211> LENGTH: 1704
<212> TYPE: DNA
<213> ORGANISM: Phaeodactylum tricornutum

<400> SEQUENCE: 11

atgagtcact ctagtttgga tgtgttcggg acctgccttg cccaagttgg cgaagacgca      60

acgacaaagg agctactaga atgcgtttcc tttagtttgt cgcgagcagt gccagacggt     120

ctcgatgagc ctagttctaa aggcttcacg cggtctatcg ttgtcgtgtt tgcggctgcc     180

ttggtttttt tcatgcaagc cggctttgcc atgctgtgcg ctggagccgt tagggccaag     240

aatgttcaaa acaccatgct caagaatctt ttggatgctt gtggtgccgc cattgcgttc     300

tttactgtag gctacgcctt tgcctttggc ggtacggact ttcccaccga caccgacacc     360

gacaccggca acaaccaaac aacattcatt ggcacatcga actttttctt ggtgaatgtg     420

gacgattatt cctttggct gtttcaatac gcattttccg ccgcgtccgc aaccattgtt     480

gctggaacac tggctgaacg gtgtcaaatg gccgcctacc tgggatattc cgctttgtta     540

acgggatggg tgtaccccat tgtcgctcac gctgtatgga acgtccacgg cttcctatcg     600

gctcatgcgg tagaaccttt gtgggggtt ggaatggtag attttgccgg ttctggggtc     660

gttcacgtta cgggaggtgt gacagcgctc ttcgcgacaa taattctggg tccccgccgt     720

ggacgctttc acgaccaaga tggccaaaga ttgataaggc cgcgaatatt tcctggacac     780

tcctttgctc tgcaaatgct tggaaccctt atcttatggt ttggctggta cggattcaat     840

attggcgctg ctctgctgct ggacgtgcct agttcagaca atattgcagc tctggctgcg     900
```

gtgaatacga ccttgtcggg cgggacggct ggcatcgttg ctctcttttt caatttgtgg 960
tatctggaca aaagaactgg cgaagcctat tttgacttga aatttgccat gaatgggtgc 1020
ctctgcggtc tcgtggccat cactggaggc tgtggtgtgg tcgaaccctg ggctgccgtt 1080
gtgattggct ttgtcgccgg tttgttgtac aacatcggaa gtcgcggact tatatatttg 1140
cgtttggatg atgccgtgga tgccattccg gtacatttgt gcaacggctc gtggggtctc 1200
gtagcagtag ggctgtttgc ctccccctcc cggctactag ttatttacgg acatagcgat 1260
catccaggat ggttttactc attacgagat ggcgaatccg atttccggtt actggcttcc 1320
cagttggtgg gccttatttt cattgtcttc tgggtcatgt tcaacatgct gccttttttc 1380
gtttggttaa actaccgtgg ctggtttcgg tccgatccgt tggaagagtt ggtgggtctc 1440
gacctgagct atcacggcgg tttaatgctg cacgaggaag ttgatcccga atacatatcg 1500
gcctatcgca agggccaaca cgaggctcat tctcgtactc tgcgacaacg gaaacgcaca 1560
tcccacgtgc gcttggaatc agtgagcgaa cattccgttg cgccaaatgg cggagactca 1620
gcccatacta gtaacggcga ttcgctcacg gaaacggtca ctatccgtga accggactcc 1680
ggttggccaa gggggaacgt ataa 1704

<210> SEQ ID NO 12
<211> LENGTH: 567
<212> TYPE: PRT
<213> ORGANISM: Phaeodactylum tricornutum

<400> SEQUENCE: 12

Met Ser His Ser Ser Leu Asp Val Phe Gly Thr Cys Leu Ala Gln Val
1               5                   10                  15

Gly Glu Asp Ala Thr Thr Lys Glu Leu Leu Glu Cys Val Ser Phe Ser
            20                  25                  30

Leu Ser Arg Ala Val Pro Asp Gly Leu Asp Glu Pro Ser Ser Lys Gly
        35                  40                  45

Phe Thr Arg Ser Ile Val Val Val Phe Ala Ala Ala Leu Val Phe Phe
    50                  55                  60

Met Gln Ala Gly Phe Ala Met Leu Cys Ala Gly Ala Val Arg Ala Lys
65                  70                  75                  80

Asn Val Gln Asn Thr Met Leu Lys Asn Leu Leu Asp Ala Cys Gly Ala
                85                  90                  95

Ala Ile Ala Phe Phe Thr Val Gly Tyr Ala Phe Ala Phe Gly Gly Thr
            100                 105                 110

Asp Phe Pro Thr Asp Thr Asp Thr Asp Thr Gly Asn Asn Gln Thr Thr
        115                 120                 125

Phe Ile Gly Thr Ser Asn Phe Phe Leu Val Asn Val Asp Asp Tyr Ser
    130                 135                 140

Phe Trp Leu Phe Gln Tyr Ala Phe Ser Ala Ala Ser Ala Thr Ile Val
145                 150                 155                 160

Ala Gly Thr Leu Ala Glu Arg Cys Gln Met Ala Ala Tyr Leu Gly Tyr
                165                 170                 175

Ser Ala Leu Leu Thr Gly Trp Val Tyr Pro Ile Val Ala His Ala Val
            180                 185                 190

Trp Asn Val His Gly Phe Leu Ser Ala His Ala Val Glu Pro Leu Trp
        195                 200                 205

Gly Val Gly Met Val Asp Phe Ala Gly Ser Gly Val Val His Val Thr
    210                 215                 220

Gly Gly Val Thr Ala Leu Phe Ala Thr Ile Ile Leu Gly Pro Arg Arg
225                 230                 235                 240

-continued

```
Gly Arg Phe His Asp Gln Asp Gly Gln Arg Leu Ile Arg Pro Arg Ile
                245                 250                 255

Phe Pro Gly His Ser Phe Ala Leu Gln Met Leu Gly Thr Leu Ile Leu
            260                 265                 270

Trp Phe Gly Trp Tyr Gly Phe Asn Ile Gly Ala Ala Leu Leu Leu Asp
        275                 280                 285

Val Pro Ser Ser Asp Asn Ile Ala Ala Leu Ala Ala Val Asn Thr Thr
    290                 295                 300

Leu Ser Gly Gly Thr Ala Gly Ile Val Ala Leu Phe Phe Asn Leu Trp
305                 310                 315                 320

Tyr Leu Asp Lys Arg Thr Gly Glu Ala Tyr Phe Asp Leu Lys Phe Ala
                325                 330                 335

Met Asn Gly Cys Leu Cys Gly Leu Val Ala Ile Thr Gly Gly Cys Gly
            340                 345                 350

Val Val Glu Pro Trp Ala Ala Val Val Ile Gly Phe Val Ala Gly Leu
        355                 360                 365

Leu Tyr Asn Ile Gly Ser Arg Gly Leu Ile Tyr Leu Arg Leu Asp Asp
    370                 375                 380

Ala Val Asp Ala Ile Pro Val His Leu Cys Asn Gly Ser Trp Gly Leu
385                 390                 395                 400

Val Ala Val Gly Leu Phe Ala Ser Pro Ser Arg Leu Leu Val Ile Tyr
                405                 410                 415

Gly His Ser Asp His Pro Gly Trp Phe Tyr Ser Leu Arg Asp Gly Glu
            420                 425                 430

Ser Asp Phe Arg Leu Leu Ala Ser Gln Leu Val Gly Leu Ile Phe Ile
        435                 440                 445

Val Phe Trp Val Met Phe Asn Met Leu Pro Phe Phe Val Trp Leu Asn
    450                 455                 460

Tyr Arg Gly Trp Phe Arg Ser Asp Pro Leu Glu Glu Leu Val Gly Leu
465                 470                 475                 480

Asp Leu Ser Tyr His Gly Gly Leu Met Leu His Glu Glu Val Asp Pro
                485                 490                 495

Glu Tyr Ile Ser Ala Tyr Arg Lys Gly Gln His Glu Ala His Ser Arg
            500                 505                 510

Thr Leu Arg Gln Arg Lys Arg Thr Ser His Val Arg Leu Glu Ser Val
        515                 520                 525

Ser Glu His Ser Val Ala Pro Asn Gly Gly Asp Ser Ala His Thr Ser
    530                 535                 540

Asn Gly Asp Ser Leu Thr Glu Thr Val Thr Ile Arg Glu Pro Asp Ser
545                 550                 555                 560

Gly Trp Pro Arg Gly Asn Val
                565
```

<210> SEQ ID NO 13
<211> LENGTH: 1665
<212> TYPE: DNA
<213> ORGANISM: Phaeodactylum tricornutum

<400> SEQUENCE: 13

```
atgagcacat ccgatggcag tctgtttcaa cagtgttctg ccgtcgctgg ggacagtgac      60

ccttcccgga ttctgcagtg tgtgtccgat gctctcgaaa ccaaccaaaa cgatcgagct     120

gccgatctca ataactggtt tctcatcatc gctggggcac tcgtcttttt catgcagtcc     180

ggcttcgcca tgctgtgtgc ggggtgtgtg cggaaaaaga acgtccaaaa caccatgctc     240
```

```
aagaatcttc tcgatgcctg cggtgccgct ctcgggtttt acgtaatcgg ttacgccttg    300

gcctttggtg gacaaaacga gcgatccgat gttacctttg tgggtaccac ggactttttc    360

aactggaaca gcgccgtccc ggtaaatcaa gccttttggt ttttcgaatt tgccttttcg    420

gccacgtccg tgacgattgt ggccgggacg ctggcggaac ggtgtcaaat ggtcgcctac    480

ctgtgctact cggtattctt aacaggcttt gtgtatcccg ttgtggccca ctccatctgg    540

agcaacaacg gctttctaag tgcatttgca gccgagccct tccagggcat tggcgtcctg    600

gactttgccg ggtcgggtgt ggtacacgtg acgggcggga ccactgcctt ggtcgccacg    660

tatatgctag ggcccgtaa ggggcgcttc tacgacgcac gtgggagaga attggaaaag    720

cccaaagcat ttcccggcca ttccatggcc ttgcagatga tgggcaccat gattctgtgg    780

ttcggatggt acggcttcaa ccctggttcg gccttgttgc tgacggcgac gtccaataca    840

ggtggcgtag cggctctcgc ggccgtgaac acgtccctct ctgccgcttc gggtgccgtt    900

tccgctctct ttacctcttt gtatctcgaa gaacgcaaga ctggagaata ctccttcaac    960

atcaccatgg ctatgaacgg tgctttggct ggcttagtgg gtattacggc cggctgtggc   1020

accgtcgaaa attgggccgc ttgttgcaca gggctcgtgt ctggatgggt ctatatattt   1080

ggcagtgcct tcttgttgcg tataaagatt gacgatgcag tcgacgcaat tccggtgcat   1140

atgttttgtg gcgcctgggg tcttattgca accggcctat tcagctcgcc acgccatacg   1200

ttagaagcat ttggtacgga cgcacacgta ggttggttct acagtcttgg ccaagattct   1260

ttggacgcta ttctcttgat gaaccagctt ttgggtcttt tatttattct cgggtggagc   1320

gccatcttga tgtcaccatt tttctggtgg ctgaactaca tgggatggtt gagggccgac   1380

tccttggagg agttggtagg tctggatcaa gcctaccacg gtggaaggga ggctggagag   1440

ggctttgatg atgaagtgcc ttttgccaca tccaaagaca aaccagacac tttacgtcga   1500

cggaaaggtg gcaacagcgc ggagggcacc cgcgatgatg gaagttggac cgatttgact   1560

gcctcggctc ctcgggaaac tgcgcctctg ccagaacttt attgtgagaa cgatgcgtct   1620

tccaaagaat ccgacgacga tccgtccgga atgcaccacg cataa                   1665


<210> SEQ ID NO 14
<211> LENGTH: 554
<212> TYPE: PRT
<213> ORGANISM: Phaeodactylum tricornutum

<400> SEQUENCE: 14

Met Ser Thr Ser Asp Gly Ser Leu Phe Gln Gln Cys Ser Ala Val Ala
1               5                   10                  15

Gly Asp Ser Asp Pro Ser Arg Ile Leu Gln Cys Val Ser Asp Ala Leu
            20                  25                  30

Glu Thr Asn Gln Asn Asp Arg Ala Ala Asp Leu Asn Asn Trp Phe Leu
        35                  40                  45

Ile Ile Ala Gly Ala Leu Val Phe Phe Met Gln Ser Gly Phe Ala Met
    50                  55                  60

Leu Cys Ala Gly Cys Val Arg Lys Lys Asn Val Gln Asn Thr Met Leu
65                  70                  75                  80

Lys Asn Leu Leu Asp Ala Cys Gly Ala Ala Leu Gly Phe Tyr Val Ile
                85                  90                  95

Gly Tyr Ala Leu Ala Phe Gly Gly Gln Asn Glu Arg Ser Asp Val Thr
            100                 105                 110

Phe Val Gly Thr Thr Asp Phe Phe Asn Trp Asn Ser Ala Val Pro Val
        115                 120                 125
```

-continued

```
Asn Gln Ala Phe Trp Phe Phe Glu Phe Ala Phe Ser Ala Thr Ser Val
    130                 135                 140

Thr Ile Val Ala Gly Thr Leu Ala Glu Arg Cys Gln Met Val Ala Tyr
145                 150                 155                 160

Leu Cys Tyr Ser Val Phe Leu Thr Gly Phe Val Tyr Pro Val Val Ala
                165                 170                 175

His Ser Ile Trp Ser Asn Asn Gly Phe Leu Ser Ala Phe Ala Ala Glu
            180                 185                 190

Pro Phe Gln Gly Ile Gly Val Leu Asp Phe Ala Gly Ser Gly Val Val
        195                 200                 205

His Val Thr Gly Gly Thr Thr Ala Leu Val Ala Thr Tyr Met Leu Gly
    210                 215                 220

Ala Arg Lys Gly Arg Phe Tyr Asp Ala Arg Gly Arg Glu Leu Glu Lys
225                 230                 235                 240

Pro Lys Ala Phe Pro Gly His Ser Met Ala Leu Gln Met Met Gly Thr
                245                 250                 255

Met Ile Leu Trp Phe Gly Trp Tyr Gly Phe Asn Pro Gly Ser Ala Leu
            260                 265                 270

Leu Leu Thr Ala Thr Ser Asn Thr Gly Gly Val Ala Ala Leu Ala Ala
        275                 280                 285

Val Asn Thr Ser Leu Ser Ala Ala Ser Gly Ala Val Ser Ala Leu Phe
    290                 295                 300

Thr Ser Leu Tyr Leu Glu Glu Arg Lys Thr Gly Glu Tyr Ser Phe Asn
305                 310                 315                 320

Ile Thr Met Ala Met Asn Gly Ala Leu Ala Gly Leu Val Gly Ile Thr
                325                 330                 335

Ala Gly Cys Gly Thr Val Glu Asn Trp Ala Ala Cys Cys Thr Gly Leu
            340                 345                 350

Val Ser Gly Trp Val Tyr Ile Phe Gly Ser Ala Phe Leu Leu Arg Ile
        355                 360                 365

Lys Ile Asp Asp Ala Val Asp Ala Ile Pro Val His Met Phe Cys Gly
    370                 375                 380

Ala Trp Gly Leu Ile Ala Thr Gly Leu Phe Ser Ser Pro Arg His Thr
385                 390                 395                 400

Leu Glu Ala Phe Gly Thr Asp Ala His Val Gly Trp Phe Tyr Ser Leu
                405                 410                 415

Gly Gln Asp Ser Leu Asp Ala Ile Leu Leu Met Asn Gln Leu Leu Gly
            420                 425                 430

Leu Leu Phe Ile Leu Gly Trp Ser Ala Ile Leu Met Ser Pro Phe Phe
        435                 440                 445

Trp Trp Leu Asn Tyr Met Gly Trp Leu Arg Ala Asp Ser Leu Glu Glu
    450                 455                 460

Leu Val Gly Leu Asp Gln Ala Tyr His Gly Gly Arg Glu Ala Gly Glu
465                 470                 475                 480

Gly Phe Asp Asp Glu Val Pro Phe Ala Thr Ser Lys Asp Lys Pro Asp
                485                 490                 495

Thr Leu Arg Arg Arg Lys Gly Gly Asn Ser Ala Glu Gly Thr Arg Asp
            500                 505                 510

Asp Gly Ser Trp Thr Asp Leu Thr Ala Ser Ala Pro Arg Glu Thr Ala
        515                 520                 525

Pro Leu Pro Glu Leu Tyr Cys Glu Asn Asp Ala Ser Ser Lys Glu Ser
    530                 535                 540

Asp Asp Asp Pro Ser Gly Met His His Ala
545                 550
```

<210> SEQ ID NO 15
<211> LENGTH: 1620
<212> TYPE: DNA
<213> ORGANISM: Phaeodactylum tricornutum

<400> SEQUENCE: 15
atgatctcta ctggctcttc cacgtccacg aatgcctacg gcacttgctc ggttcagctg 60
ggcgaaaact cttccgcgaa agagctcttg gaatgtgttt cagattatct acagaatcag 120
gaggcgcctt tctcgtctac tctggtactc acttttgcgg gcgcgattgt ctttctaatg 180
caagccggct ttgccatggt ctgtgctggt gctgtccgca caaaaaatgt ccaaaacgcc 240
atgctcaaga atctgttgga tgcttgcggt gcgtccttgg cgttcttttc cattggctac 300
gctctggggt ttgggggtat ggagcccgaa agttccaaaa agacctttgt cggacatagt 360
caattctttc tgatggacgt tgacgactac gctttttggt tattccaata cgccttttcc 420
gctgcatctg ccacaattgt cgcaggaacg ctcgcggaac gatgtcaaat gacggcctat 480
ctttgctact cccttatgct aaccgggtgg gtataccccg ttattctaca ctccatatgg 540
aatcccaacg gctggctatc tgcgtactcg gttgatccgc tttggggcag cgggctggtg 600
gattttgctg gctctggcgt cgttcatgtg accggaggaa tcaccgctct gtttgctaca 660
atggttttgg gcccccgacg aggacgcttt cacgatgatc ttgggcatga tctggcacgg 720
ccacgggaat ttcaggctca ttcgccggct ctgcaaatgc ttggtacttt tattttgtgg 780
tttggctttt acggatttaa cattggctcc gcgctgataa gcacaaagca aggctcagac 840
gaagcagccg ccttggccgg tgtcaacaca acgctctccg ctagcgcggc aggtattgtg 900
gcgctgtttt caaatctatg gtacctggag aagacgaccg gtgagcctct ctttgatcta 960
aagtatgcta tgaatggcgc catctgcggt cttgtagcta tttctggcgg ctgcggggtc 1020
ttcgagccct gggccgcggt ggtcaccggg gccgtggccg gtgtgatata tctattaggt 1080
agtcgcggac ttgtatccat gcgactggat gacgctgtgg atgccatccc tgtacacctc 1140
tgtggtgggg cctggggcat cctggcggtg ggactgttcg cagcgcccga acgtctcctt 1200
tccgtgtatg gacggaataa tcacccagga ttggtttata gcattcgtga aggagatatc 1260
gatggcgttc ttttcggaat tcaactaatt ggtctcatgt tcatcatggg atgggttatg 1320
atcatcatgc tacctttctt tgtatggctc aactggaaag gctggttccg atcagacccg 1380
ctggaggaga ttctcgggct cgatttaagc tatcacgtcg gattggcgtt acataccaac 1440
aatgttcatc cggaatacgt tggcagcgaa aaagatgtgg tcgacgaaat tatttctacg 1500
cgccaacgaa aggtcaacgg gagcaccact accaaggcga cctcaggtac ggaagaattg 1560
gagtatatcc cggaagttag cgacgaagac ttgagcgaga tgaaagagga atgcttgtga 1620

<210> SEQ ID NO 16
<211> LENGTH: 539
<212> TYPE: PRT
<213> ORGANISM: Phaeodactylum tricornutum

<400> SEQUENCE: 16

Met Ile Ser Thr Gly Ser Ser Thr Ser Thr Asn Ala Tyr Gly Thr Cys
1 5 10 15

Ser Val Gln Leu Gly Glu Asn Ser Ser Ala Lys Glu Leu Leu Glu Cys
20 25 30

Val Ser Asp Tyr Leu Gln Asn Gln Glu Ala Pro Phe Ser Ser Thr Leu
35 40 45

```
Val Leu Thr Phe Ala Gly Ala Ile Val Phe Leu Met Gln Ala Gly Phe
    50                  55                  60

Ala Met Val Cys Ala Gly Ala Val Arg Thr Lys Asn Val Gln Asn Ala
65                  70                  75                  80

Met Leu Lys Asn Leu Leu Asp Ala Cys Gly Ala Ser Leu Ala Phe Phe
                85                  90                  95

Ser Ile Gly Tyr Ala Leu Gly Phe Gly Gly Met Glu Pro Glu Ser Ser
            100                 105                 110

Lys Lys Thr Phe Val Gly His Ser Gln Phe Phe Leu Met Asp Val Asp
        115                 120                 125

Asp Tyr Ala Phe Trp Leu Phe Gln Tyr Ala Phe Ser Ala Ala Ser Ala
    130                 135                 140

Thr Ile Val Ala Gly Thr Leu Ala Glu Arg Cys Gln Met Thr Ala Tyr
145                 150                 155                 160

Leu Cys Tyr Ser Leu Met Leu Thr Gly Trp Val Tyr Pro Val Ile Leu
                165                 170                 175

His Ser Ile Trp Asn Pro Asn Gly Trp Leu Ser Ala Tyr Ser Val Asp
            180                 185                 190

Pro Leu Trp Gly Ser Gly Leu Val Asp Phe Ala Gly Ser Gly Val Val
        195                 200                 205

His Val Thr Gly Gly Ile Thr Ala Leu Phe Ala Thr Met Val Leu Gly
    210                 215                 220

Pro Arg Arg Gly Arg Phe His Asp Asp Leu Gly His Asp Leu Ala Arg
225                 230                 235                 240

Pro Arg Glu Phe Gln Ala His Ser Pro Ala Leu Gln Met Leu Gly Thr
                245                 250                 255

Phe Ile Leu Trp Phe Gly Phe Tyr Gly Phe Asn Ile Gly Ser Ala Leu
            260                 265                 270

Ile Ser Thr Lys Gln Gly Ser Asp Glu Ala Ala Ala Leu Ala Gly Val
        275                 280                 285

Asn Thr Thr Leu Ser Ala Ser Ala Ala Gly Ile Val Ala Leu Phe Ser
    290                 295                 300

Asn Leu Trp Tyr Leu Glu Lys Thr Thr Gly Glu Pro Leu Phe Asp Leu
305                 310                 315                 320

Lys Tyr Ala Met Asn Gly Ala Ile Cys Gly Leu Val Ala Ile Ser Gly
                325                 330                 335

Gly Cys Gly Val Phe Glu Pro Trp Ala Ala Val Val Thr Gly Ala Val
            340                 345                 350

Ala Gly Val Ile Tyr Leu Leu Gly Ser Arg Gly Leu Val Ser Met Arg
        355                 360                 365

Leu Asp Asp Ala Val Asp Ala Ile Pro Val His Leu Cys Gly Gly Ala
    370                 375                 380

Trp Gly Ile Leu Ala Val Gly Leu Phe Ala Ala Pro Glu Arg Leu Leu
385                 390                 395                 400

Ser Val Tyr Gly Arg Asn Asn His Pro Gly Leu Val Tyr Ser Ile Arg
                405                 410                 415

Glu Gly Asp Ile Asp Gly Val Leu Phe Gly Ile Gln Leu Ile Gly Leu
            420                 425                 430

Met Phe Ile Met Gly Trp Val Met Ile Ile Met Leu Pro Phe Phe Val
        435                 440                 445

Trp Leu Asn Trp Lys Gly Trp Phe Arg Ser Asp Pro Leu Glu Glu Ile
    450                 455                 460

Leu Gly Leu Asp Leu Ser Tyr His Val Gly Leu Ala Leu His Thr Asn
465                 470                 475                 480
```

```
Asn Val His Pro Glu Tyr Val Gly Ser Glu Lys Asp Val Val Asp Glu
                485                 490                 495

Ile Ile Ser Thr Arg Gln Arg Lys Val Asn Gly Ser Thr Thr Thr Lys
            500                 505                 510

Ala Thr Ser Gly Thr Glu Glu Leu Glu Tyr Ile Pro Glu Val Ser Asp
        515                 520                 525

Glu Asp Leu Ser Glu Met Lys Glu Glu Cys Leu
    530                 535
```

<210> SEQ ID NO 17
<211> LENGTH: 1557
<212> TYPE: DNA
<213> ORGANISM: Cylindrotheca fusiformis

<400> SEQUENCE: 17

```
atggctgagt ttgataacac gtttatcttg gatttttgca gtggtggaaa tgaatcgtcg     60

tctgacgttc aggccttgtg tcaagttgct ggtcttgcaa atggcacaag tgcctctgcc    120

gctggacttg ttgagggtat caacaccttc ttcctacttt tcgcaggagc tctggtcttt    180

ctcatgcaag ctggcttcgc catgctgtgc gctggatccg tccgtcaaaa gaacgtcaag    240

aatatcatgt tgaagaacat gttggacgct tgtggtggtg ctattggttt ctggactatc    300

gggtatgcgt tcgcctacgc tgataactcg tcgggagaca aaaccttcat tggaggcaag    360

aacttctttg tgaaccaatt ggatgagtct ggtggcgcat ggattggttt ctttttccaa    420

ttcgcctttg ctgccactgc cgccactatt gtcgccggaa ccgttgctga gcgctgtaag    480

atgagtgcat acctttgcta ctcagtcttc ctcactggtt ttgtctatcc tgtcgttgtt    540

cactccatct ggagtgctga tggatggttg actgccttcc gtgatgatcc ttggaagggt    600

gtcggtgtca ttgatttcgc cggatctggt gttgtgcaca tgaccggtgg agccactgct    660

cttgttgctg ctattgttct tggaccccgt aagggacgtt tctatgatga ggatggaaat    720

gctcttgaaa cccctgcaag tttcccagct cacagtgtgg cccttcaagt ccttggtacc    780

ttccttcttt ggttcggatg gtatggattc aacccaggat ctgctcttgt cattgacaat    840

gctgcgtccg cttctacctc agcactttgt gctgtcacta ccactcttgc cgctgccagt    900

ggttgtgtct gtgcgatgtt cactgatacc atcattgaaa tgatggcaac aggagaagca    960

tcttacgatt tgaccatggc catgaacggt gctcttggag gacttgttgc catcactgct   1020

ggatgctccg ttgtcacccc ttgggcttcg atcatcattg gtatcattgc tgggtgggtc   1080

tacattgcat tttccaaact cctagtcaaa ttgaagatcg atgatgctgt tgatgccgtt   1140

cctgttcact tcgccaatgg tatgtggggt gtcttggctg tgggtttctt cgccgaaccc   1200

gacgccatgg ttactgccgg gtacaacgat gtcccaggag tcttctacaa gggagatggt   1260

aaacttctcc tgtgccaatt tgtcgctatc atctggattt gcgcttggat cttcttcttg   1320

atgactcctt tcttcgtcgt cttgaacatc ttgggtatgt tccgtgtcga tcctcttgag   1380

gaagaagttg gtcttgatat ttcccaccat cgtggagctg cctacgacat gaccagtgcc   1440

aagaaggaag atgtcgagga gctcatggaa caccgttctt ctaagcatgg aaaggttgag   1500

gtccccaagg aagttcaaaa ggaggacacc gcctaaggaa tttgacatcc cttctag      1557
```

<210> SEQ ID NO 18
<211> LENGTH: 511
<212> TYPE: PRT
<213> ORGANISM: Cylindrotheca fusiformis

<400> SEQUENCE: 18

-continued

```
Met Ala Glu Phe Asp Asn Thr Phe Ile Leu Asp Phe Cys Ser Gly Gly
1               5                   10                  15

Asn Glu Ser Ser Ser Asp Val Gln Ala Leu Cys Gln Val Ala Gly Leu
            20                  25                  30

Ala Asn Gly Thr Ser Ala Ser Ala Ala Gly Leu Val Glu Gly Ile Asn
        35                  40                  45

Thr Phe Phe Leu Leu Phe Ala Gly Ala Leu Val Phe Leu Met Gln Ala
    50                  55                  60

Gly Phe Ala Met Leu Cys Ala Gly Ser Val Arg Gln Lys Asn Val Lys
65                  70                  75                  80

Asn Ile Met Leu Lys Asn Met Leu Asp Ala Cys Gly Gly Ala Ile Gly
                85                  90                  95

Phe Trp Thr Ile Gly Tyr Ala Phe Ala Tyr Ala Asp Asn Ser Ser Gly
            100                 105                 110

Asp Lys Thr Phe Ile Gly Gly Lys Asn Phe Phe Val Asn Gln Leu Asp
        115                 120                 125

Glu Ser Gly Gly Ala Trp Ile Gly Phe Phe Phe Gln Phe Ala Phe Ala
    130                 135                 140

Ala Thr Ala Ala Thr Ile Val Ala Gly Thr Val Ala Glu Arg Cys Lys
145                 150                 155                 160

Met Ser Ala Tyr Leu Cys Tyr Ser Val Phe Leu Thr Gly Phe Val Tyr
                165                 170                 175

Pro Val Val Val His Ser Ile Trp Ser Ala Asp Gly Trp Leu Thr Ala
            180                 185                 190

Phe Arg Asp Asp Pro Trp Lys Gly Val Gly Val Ile Asp Phe Ala Gly
        195                 200                 205

Ser Gly Val Val His Met Thr Gly Gly Ala Thr Ala Leu Val Ala Ala
    210                 215                 220

Ile Val Leu Gly Pro Arg Lys Gly Arg Phe Tyr Asp Glu Asp Gly Asn
225                 230                 235                 240

Ala Leu Glu Thr Pro Ala Ser Phe Pro Ala His Ser Val Ala Leu Gln
                245                 250                 255

Val Leu Gly Thr Phe Leu Leu Trp Phe Gly Trp Tyr Gly Phe Asn Pro
            260                 265                 270

Gly Ser Ala Leu Val Ile Asp Asn Ala Ala Ser Ala Ser Thr Ser Ala
        275                 280                 285

Leu Cys Ala Val Thr Thr Thr Leu Ala Ala Ala Ser Gly Cys Val Cys
    290                 295                 300

Ala Met Phe Thr Asp Thr Ile Ile Glu Met Met Ala Thr Gly Glu Ala
305                 310                 315                 320

Ser Tyr Asp Leu Thr Met Ala Met Asn Gly Ala Leu Gly Gly Leu Val
                325                 330                 335

Ala Ile Thr Ala Gly Cys Ser Val Val Thr Pro Trp Ala Ser Ile Ile
            340                 345                 350

Ile Gly Ile Ile Ala Gly Trp Val Tyr Ile Ala Phe Ser Lys Leu Leu
        355                 360                 365

Val Lys Leu Lys Ile Asp Asp Ala Val Asp Ala Val Pro Val His Phe
    370                 375                 380

Ala Asn Gly Met Trp Gly Val Leu Ala Val Gly Phe Phe Ala Glu Pro
385                 390                 395                 400

Asp Ala Met Val Thr Ala Gly Tyr Asn Asp Val Pro Gly Val Phe Tyr
                405                 410                 415

Lys Gly Asp Gly Lys Leu Leu Leu Cys Gln Phe Val Ala Ile Ile Trp
```

-continued

```
            420                 425                 430

Ile Cys Ala Trp Ile Phe Phe Leu Met Thr Pro Phe Phe Val Val Leu
        435                 440                 445

Asn Ile Leu Gly Met Phe Arg Val Asp Pro Leu Glu Glu Glu Val Gly
    450                 455                 460

Leu Asp Ile Ser His His Arg Gly Ala Ala Tyr Asp Met Thr Ser Ala
465                 470                 475                 480

Lys Lys Glu Asp Val Glu Glu Leu Met Glu His Arg Ser Ser Lys His
                485                 490                 495

Gly Lys Val Glu Val Pro Lys Glu Val Gln Lys Glu Asp Thr Ala
            500                 505                 510


<210> SEQ ID NO 19
<211> LENGTH: 1622
<212> TYPE: DNA
<213> ORGANISM: Cylindrotheca fusiformis

<400> SEQUENCE: 19

atggctgagt ttgataacac gtttatcttg gatttttgca gtggtggaaa tgaatcgtcg     60

tctgacgttc aggccttgtg tcaagttgct ggtgtaagtt gtttgccgat gttattctga    120

ccacagtata tcattttgcc ttgacttaca ccgtcgcgtc ttgatgttgt gcacttcagc    180

ttgcaaatgg cacaagtgcc tctgccgctg gacttgttga gggtatcaac accttcttcc    240

tacttttcgc aggagctctg gtctttctca tgcaagctgg cttcgccatg ctgtgcgctg    300

gatccgtccg tcaaaagaac gtcaagaata tcatgttgaa gaacatgttg gacgcttgtg    360

gtggtgctat tggtttctgg actatcgggt atgcgttcgc ctacgctgat aactcgtcgg    420

gagacaaaac cttcattgga ggcaagaact tctttgtgaa ccaattggat gagtctggtg    480

gcgcatggat tggtttcttt ttccaattcg cctttgctgc cactgccgcc actattgtcg    540

ccggaaccgt tgctgagcgc tgtaagatga gtgcatacct ttgctactca gtcttcctca    600

ctggttttgt ctatcctgtc gttgttcact ccatctggag tgctgatgga tggttgactg    660

ccttccgtga tgatccttgg aagggtgtcg gtgtcattga tttcgccgga tctggtgttg    720

tgcacatgac cggtggagcc actgctcttg ttgctgctat tgttcttgga ccccgtaagg    780

gacgtttcta tgatgaggat ggaaatgctc ttgaaacccc tgcaagtttc ccagctcaca    840

gtgtggccct tcaagtcctt ggtaccttcc ttctttggtt cggatggtat ggattcaacc    900

caggatctgc tcttgtcatt gacaatgctg cgtccgcttc tacctcagca ctttgtgctg    960

tcactaccac tcttgccgct gccagtggtt gtgtctgtgc gatgttcact gataccatca   1020

ttgaaatgat ggcaacagga gaagcatctt acgatttgac catggccatg aacggtgctc   1080

ttggaggact tgttgccatc actgctggat gctccgttgt caccccttgg gcttcgatca   1140

tcattggtat cattgctggg tgggtctaca ttgcattttc caaactccta gtcaaattga   1200

agatcgatga tgctgttgat gccgttcctg ttcacttcgc caatggtatg tggggtgtct   1260

tggctgtggg tttcttcgcc gaacccgacg ccatggttac tgccgggtac aacgatgtcc   1320

caggagtctt ctacaaggga gatggtaaac ttctcctgtg ccaatttgtc gctatcatct   1380

ggatttgcgc ttggatcttc ttcttgatga ctcctttctt cgtcgtcttg aacatcttgg   1440

gtatgttccg tgtcgatcct cttgaggaag aagttggtct tgatatttcc caccatcgtg   1500

gagctgccta cgacatgacc agtgccaaga aggaagatgt cgaggagctc atggaacacc   1560

gttcttctaa gcatggaaag gttgaggtcc ccaaggaagt tcaaaaggag gacaccgcct   1620

aa                                                                   1622
```

<210> SEQ ID NO 20
<211> LENGTH: 450
<212> TYPE: PRT
<213> ORGANISM: Cylindrotheca fusiformis

<400> SEQUENCE: 20

```
Met Gln Ala Gly Phe Ala Met Leu Cys Ala Gly Ser Val Arg Gln Lys
1               5                   10                  15

Asn Val Lys Asn Ile Met Leu Lys Asn Met Leu Asp Ala Cys Gly Gly
            20                  25                  30

Ala Ile Gly Phe Trp Thr Ile Gly Tyr Ala Phe Ala Tyr Ala Asp Asn
        35                  40                  45

Ser Ser Gly Asp Lys Thr Phe Ile Gly Gly Lys Asn Phe Phe Val Asn
    50                  55                  60

Gln Leu Asp Glu Ser Gly Gly Ala Trp Ile Gly Phe Phe Phe Gln Phe
65                  70                  75                  80

Ala Phe Ala Ala Thr Ala Ala Thr Ile Val Ala Gly Thr Val Ala Glu
                85                  90                  95

Arg Cys Lys Met Ser Ala Tyr Leu Cys Tyr Ser Val Phe Leu Thr Gly
            100                 105                 110

Phe Val Tyr Pro Val Val Val His Ser Ile Trp Ser Ala Asp Gly Trp
        115                 120                 125

Leu Thr Ala Phe Arg Asp Asp Pro Trp Lys Gly Val Gly Val Ile Asp
    130                 135                 140

Phe Ala Gly Ser Gly Val Val His Met Thr Gly Gly Ala Thr Ala Leu
145                 150                 155                 160

Val Ala Ala Ile Val Leu Gly Pro Arg Lys Gly Arg Phe Tyr Asp Glu
                165                 170                 175

Asp Gly Asn Ala Leu Glu Thr Pro Ala Ser Phe Pro Ala His Ser Val
            180                 185                 190

Ala Leu Gln Val Leu Gly Thr Phe Leu Leu Trp Phe Gly Trp Tyr Gly
        195                 200                 205

Phe Asn Pro Gly Ser Ala Leu Val Ile Asp Asn Ala Ala Ser Ala Ser
    210                 215                 220

Thr Ser Ala Leu Cys Ala Val Thr Thr Thr Leu Ala Ala Ala Ser Gly
225                 230                 235                 240

Cys Val Cys Ala Met Phe Thr Asp Thr Ile Ile Glu Met Met Ala Thr
                245                 250                 255

Gly Glu Ala Ser Tyr Asp Leu Thr Met Ala Met Asn Gly Ala Leu Gly
            260                 265                 270

Gly Leu Val Ala Ile Thr Ala Gly Cys Ser Val Val Thr Pro Trp Ala
        275                 280                 285

Ser Ile Ile Ile Gly Ile Ile Ala Gly Trp Val Tyr Ile Ala Phe Ser
    290                 295                 300

Lys Leu Leu Val Lys Leu Lys Ile Asp Asp Ala Val Asp Ala Val Pro
305                 310                 315                 320

Val His Phe Ala Asn Gly Met Trp Gly Val Leu Ala Val Gly Phe Phe
                325                 330                 335

Ala Glu Pro Asp Ala Met Val Thr Ala Gly Tyr Asn Asp Val Pro Gly
            340                 345                 350

Val Phe Tyr Lys Gly Asp Gly Lys Leu Leu Leu Cys Gln Phe Val Ala
        355                 360                 365

Ile Ile Trp Ile Cys Ala Trp Ile Phe Phe Leu Met Thr Pro Phe Phe
    370                 375                 380
```

-continued

```
Val Val Leu Asn Ile Leu Gly Met Phe Arg Val Asp Pro Leu Glu Glu
385                 390                 395                 400

Glu Val Gly Leu Asp Ile Ser His His Arg Gly Ala Ala Tyr Asp Met
                405                 410                 415

Thr Ser Ala Lys Lys Glu Asp Val Glu Glu Leu Met Glu His Arg Ser
            420                 425                 430

Ser Lys His Gly Lys Val Glu Val Pro Lys Glu Val Gln Lys Glu Asp
        435                 440                 445

Thr Ala
    450


<210> SEQ ID NO 21
<211> LENGTH: 1536
<212> TYPE: DNA
<213> ORGANISM: Cylindrotheca fusiformis

<400> SEQUENCE: 21

atggctgagt tcgataacac ttttatcttg gaattttgca gtggtggaaa tgaatcgtcg      60

tctgacgttc aggtcttgtg ccaagttgcc agtctcgcaa acggcaccag tgcctctgcc     120

ggtggactta ctgagggtat caataccttc tttctacttt ttgctggagc tctagtcttt     180

atcatgcaag ctggattcgc catgctgtgt gctggatccg tccgtcaaaa gaacgtcaag     240

aatatcatgt tgaaaaacat gttggacgct tgtggtggtg ctattggttt ctggactatc     300

gggtatgcct tcgcctacgc tgataactcg tctggaaata aaacattcat tggaggcaag     360

aacttctttg tgaaccaact ggatgagtct ggaggtgcat ggattggttt cttcttccaa     420

tttgcctttg ctgccactgc cgccactatt gtcgcgggaa ccgttgccga gcgctgcaag     480

atgagtgcgt acctatgcta ctcaatcttc ctcactggtt ttgtctatcc tgtcgttgtt     540

cactccatct ggagtgctga tggatggttg actgcctttc gtgatgatcc ttggcagggt     600

gtcggtgtca tcgatttcgc cggatctggt gttgtgcata tgtgcggtgg agccactgct     660

cttgttgctg ctattgttct tggaccccgt aagggacgtt tctatgatga ggatggaaat     720

gctcttgaaa cccctgcaag tttcccagct cacagtgtgg cccttcaagt cctcggtacc     780

ttccttcttt ggttcggatg gtatggattc aacccaggat ctgctcttgt cattgacaat     840

gctgcgtccg cttctacctc agcactttgt gctgtcacta ccactcttgc cgctgccagt     900

ggttgtgtca ccgcgatgtt caccgatacc ctcattgaaa tgatggctac cggagaagca     960

tcttatgatt tgaccatggc catgaacggt gcacttgcgg ggcttgttgc catcactgcc    1020

ggatgctccg ttgtcactcc ttgggcttct ctcatcattg gtattattgg cgggtgggtc    1080

taccttggac tttctaaact tctaatcaaa ttgaagatcg atgatgctgt tgatgccgtc    1140

cctgttcact tcggtaatgg tatgtggggt gtcttggctg ttggcttctt tgccgaaccc    1200

gacgccatgg ttactgccgg gtacaacgat gtcccaggag tgttctacaa aggagatggt    1260

tctcttctcc tgtgccaatt cgtcgctatc gtttgggttt gcgcttgggt cttcttcttg    1320

atgactcctt tcttcgtcgt cttgaacatt ttgggaatgt tccgtgtcga tcctcttgag    1380

gaagaagttg gtcttgatat ttcccaccac cgtggatctg cctacgacat gactactgcc    1440

aagaaggaag atgtcgaaga gctcatggaa caccgttctt cgaagcacgg gaaggttgag    1500

atccccaagg aagttcagaa ggaggacacc gcctaa                              1536


<210> SEQ ID NO 22
<211> LENGTH: 511
<212> TYPE: PRT
```

<213> ORGANISM: Cylindrotheca fusiformis

<400> SEQUENCE: 22

```
Met Ala Glu Phe Asp Asn Thr Phe Ile Leu Glu Phe Cys Ser Gly Gly
1               5                   10                  15

Asn Glu Ser Ser Ser Asp Val Gln Val Leu Cys Gln Val Ala Ser Leu
            20                  25                  30

Ala Asn Gly Thr Ser Ala Ser Ala Gly Gly Leu Thr Glu Gly Ile Asn
        35                  40                  45

Thr Phe Phe Leu Leu Phe Ala Gly Ala Leu Val Phe Ile Met Gln Ala
    50                  55                  60

Gly Phe Ala Met Leu Cys Ala Gly Ser Val Arg Gln Lys Asn Val Lys
65                  70                  75                  80

Asn Ile Met Leu Lys Asn Met Leu Asp Ala Cys Gly Gly Ala Ile Gly
                85                  90                  95

Phe Trp Thr Ile Gly Tyr Ala Phe Ala Tyr Ala Asp Asn Ser Ser Gly
            100                 105                 110

Asn Lys Thr Phe Ile Gly Gly Lys Asn Phe Phe Val Asn Gln Leu Asp
        115                 120                 125

Glu Ser Gly Gly Ala Trp Ile Gly Phe Phe Phe Gln Phe Ala Phe Ala
    130                 135                 140

Ala Thr Ala Ala Thr Ile Val Ala Gly Thr Val Ala Glu Arg Cys Lys
145                 150                 155                 160

Met Ser Ala Tyr Leu Cys Tyr Ser Ile Phe Leu Thr Gly Phe Val Tyr
                165                 170                 175

Pro Val Val Val His Ser Ile Trp Ser Ala Asp Gly Trp Leu Thr Ala
            180                 185                 190

Phe Arg Asp Asp Pro Trp Gln Gly Val Gly Val Ile Asp Phe Ala Gly
        195                 200                 205

Ser Gly Val Val His Met Cys Gly Gly Ala Thr Ala Leu Val Ala Ala
    210                 215                 220

Ile Val Leu Gly Pro Arg Lys Gly Arg Phe Tyr Asp Glu Asp Gly Asn
225                 230                 235                 240

Ala Leu Glu Thr Pro Ala Ser Phe Pro Ala His Ser Val Ala Leu Gln
                245                 250                 255

Val Leu Gly Thr Phe Leu Leu Trp Phe Gly Trp Tyr Gly Phe Asn Pro
            260                 265                 270

Gly Ser Ala Leu Val Ile Asp Asn Ala Ala Ser Ala Ser Thr Ser Ala
        275                 280                 285

Leu Cys Ala Val Thr Thr Thr Leu Ala Ala Ala Ser Gly Cys Val Thr
    290                 295                 300

Ala Met Phe Thr Asp Thr Leu Ile Glu Met Met Ala Thr Gly Glu Ala
305                 310                 315                 320

Ser Tyr Asp Leu Thr Met Ala Met Asn Gly Ala Leu Ala Gly Leu Val
                325                 330                 335

Ala Ile Thr Ala Gly Cys Ser Val Val Thr Pro Trp Ala Ser Leu Ile
            340                 345                 350

Ile Gly Ile Ile Gly Gly Trp Val Tyr Leu Gly Leu Ser Lys Leu Leu
        355                 360                 365

Ile Lys Leu Lys Ile Asp Asp Ala Val Asp Ala Val Pro Val His Phe
    370                 375                 380

Gly Asn Gly Met Trp Gly Val Leu Ala Val Gly Phe Phe Ala Glu Pro
385                 390                 395                 400

Asp Ala Met Val Thr Ala Gly Tyr Asn Asp Val Pro Gly Val Phe Tyr
```

-continued

```
                405                 410                 415

Lys Gly Asp Gly Ser Leu Leu Leu Cys Gln Phe Val Ala Ile Val Trp
            420                 425                 430

Val Cys Ala Trp Val Phe Phe Leu Met Thr Pro Phe Phe Val Val Leu
        435                 440                 445

Asn Ile Leu Gly Met Phe Arg Val Asp Pro Leu Glu Glu Glu Val Gly
    450                 455                 460

Leu Asp Ile Ser His His Arg Gly Ser Ala Tyr Asp Met Thr Thr Ala
465                 470                 475                 480

Lys Lys Glu Asp Val Glu Glu Leu Met Glu His Arg Ser Ser Lys His
                485                 490                 495

Gly Lys Val Glu Ile Pro Lys Glu Val Gln Lys Glu Asp Thr Ala
            500                 505                 510


<210> SEQ ID NO 23
<211> LENGTH: 1563
<212> TYPE: DNA
<213> ORGANISM: Thalassiosira pseudonana

<400> SEQUENCE: 23

atggccgaac caacaacaac cataggcgac ttcaacgtca ctgcctggtg cggcgacgac      60

gctgtagcaa cctacgaagg acaatccgtc gagaacggta tctgtgcagc ctacgcctac     120

accgacgaaa ccaacaccgg tcttgatgtg ttctacctcc tcttcgccgc tgccatggtc     180

ttcttcatgc aggctggatt cgccatgctc tgtgctggat ctgtgaggca gaagaatgtg     240

aagaatatca tgcttaagaa cattttggat gcttgtggtg gagctcttgg attttggtct     300

gtgggatttg cgtttgccta cggaggatct ggaccggaga agaagggatt catcggtaac     360

gagggattct tccttggtga ctttacaact ggaggcgatt tgatcggatg gttcttccag     420

ttcgcctttg ctgccaccgc cgccacaatt gtggctggaa ccgtagccga gcgttgcaag     480

ttcgaggcct acctctgcta ttctctcatg ctcaccgggt tcgtctaccc cgtgattgtg     540

tactccatct ggtcttcctc tgggttcctc accgccttca acgacgaccc tgcctttgga     600

tgtggtatgc atgatttcgc cggatcggga gttgttcaca tgacgggagg catcactgcc     660

ctttgggccg ccaagattct cggacctcgt atcggacgct tctacgatgc tgatggcaat     720

gagcttcccg agccagtgag cttccctccc cactccgtgg cccttcaagt tcttggtact     780

ttcatccttt gggtgggctg gtacggattc aaccccggtt ccactcttct catcagtaac     840

acggccgcag ctgatgtgtc tgccctttgt gccgtcacca ccaccattgc cgccgcttcg     900

ggctctgtct ctgccatgtt cactgatatg ttcttggagc gcagaaagac cggagagact     960

atgtacgaca ttaccatgtg tatgaacggt gctctttctg gattggtggg catcaccgct    1020

ggatgctcaa tcgttgagcc ttgggctgcc tttgtcattg gaattgtcgc cggatggact    1080

tacatcttct ggtccagtct ccttgtgaag cttaagattg atgatgccgt cgatgccatt    1140

cctgttcact ttggaaacgg aatgtggggc tgcattgccg ttggactctt tgccgagcct    1200

acccgtgtag ccaacgccta cagtgaccat ggacactatg gatggttcta ctcatggggt    1260

gctggaaacg ccgatgccca ccttttggct gctcaagtct gtggtgttct ctggatcatt    1320

ggatgggttt ccgtcattat gatcccatac ttcatcctgc tcaacgtcct gggtttgttc    1380

cgtgtggatg ccctcgaaga agaagttggt ttggatatct cccaccacaa gggagctgcc    1440

tacgatatgt ccggaccttc tgaagctgcc gccgagaagt ttgagatctc taggagtcag    1500

cgtaagcttg agatccctgt ggatgtcgcg cctgctactg ctcctgccga ggatgccgcg    1560
```

taa 1563

<210> SEQ ID NO 24
<211> LENGTH: 520
<212> TYPE: PRT
<213> ORGANISM: Thalassiosira pseudonana

<400> SEQUENCE: 24

Met Ala Glu Pro Thr Thr Thr Ile Gly Asp Phe Asn Val Thr Ala Trp
1 5 10 15

Cys Gly Asp Asp Ala Val Ala Thr Tyr Glu Gly Gln Ser Val Glu Asn
20 25 30

Gly Ile Cys Ala Ala Tyr Ala Tyr Thr Asp Glu Thr Asn Thr Gly Leu
35 40 45

Asp Val Phe Tyr Leu Leu Phe Ala Ala Ala Met Val Phe Phe Met Gln
50 55 60

Ala Gly Phe Ala Met Leu Cys Ala Gly Ser Val Arg Gln Lys Asn Val
65 70 75 80

Lys Asn Ile Met Leu Lys Asn Ile Leu Asp Ala Cys Gly Gly Ala Leu
85 90 95

Gly Phe Trp Ser Val Gly Phe Ala Phe Ala Tyr Gly Gly Ser Gly Pro
100 105 110

Glu Lys Lys Gly Phe Ile Gly Asn Glu Gly Phe Phe Leu Gly Asp Phe
115 120 125

Thr Thr Gly Gly Asp Leu Ile Gly Trp Phe Phe Gln Phe Ala Phe Ala
130 135 140

Ala Thr Ala Ala Thr Ile Val Ala Gly Thr Val Ala Glu Arg Cys Lys
145 150 155 160

Phe Glu Ala Tyr Leu Cys Tyr Ser Leu Met Leu Thr Gly Phe Val Tyr
165 170 175

Pro Val Ile Val Tyr Ser Ile Trp Ser Ser Ser Gly Phe Leu Thr Ala
180 185 190

Phe Asn Asp Asp Pro Ala Phe Gly Cys Gly Met His Asp Phe Ala Gly
195 200 205

Ser Gly Val Val His Met Thr Gly Gly Ile Thr Ala Leu Trp Ala Ala
210 215 220

Lys Ile Leu Gly Pro Arg Ile Gly Arg Phe Tyr Asp Ala Asp Gly Asn
225 230 235 240

Glu Leu Pro Glu Pro Val Ser Phe Pro Pro His Ser Val Ala Leu Gln
245 250 255

Val Leu Gly Thr Phe Ile Leu Trp Val Gly Trp Tyr Gly Phe Asn Pro
260 265 270

Gly Ser Thr Leu Leu Ile Ser Asn Thr Ala Ala Ala Asp Val Ser Ala
275 280 285

Leu Cys Ala Val Thr Thr Thr Ile Ala Ala Ala Ser Gly Ser Val Ser
290 295 300

Ala Met Phe Thr Asp Met Phe Leu Glu Arg Arg Lys Thr Gly Glu Thr
305 310 315 320

Met Tyr Asp Ile Thr Met Cys Met Asn Gly Ala Leu Ser Gly Leu Val
325 330 335

Gly Ile Thr Ala Gly Cys Ser Ile Val Glu Pro Trp Ala Ala Phe Val
340 345 350

Ile Gly Ile Val Ala Gly Trp Thr Tyr Ile Phe Trp Ser Ser Leu Leu
355 360 365

Val Lys Leu Lys Ile Asp Asp Ala Val Asp Ala Ile Pro Val His Phe

```
    370                 375                 380

Gly Asn Gly Met Trp Gly Cys Ile Ala Val Gly Leu Phe Ala Glu Pro
385                 390                 395                 400

Thr Arg Val Ala Asn Ala Tyr Ser Asp His Gly His Tyr Gly Trp Phe
                405                 410                 415

Tyr Ser Trp Gly Ala Gly Asn Ala Asp Ala His Leu Leu Ala Ala Gln
            420                 425                 430

Val Cys Gly Val Leu Trp Ile Ile Gly Trp Val Ser Val Ile Met Ile
        435                 440                 445

Pro Tyr Phe Ile Leu Leu Asn Val Leu Gly Leu Phe Arg Val Asp Ala
    450                 455                 460

Leu Glu Glu Glu Val Gly Leu Asp Ile Ser His His Lys Gly Ala Ala
465                 470                 475                 480

Tyr Asp Met Ser Gly Pro Ser Glu Ala Ala Ala Glu Lys Phe Glu Ile
                485                 490                 495

Ser Arg Ser Gln Arg Lys Leu Glu Ile Pro Val Asp Val Ala Pro Ala
            500                 505                 510

Thr Ala Pro Ala Glu Asp Ala Ala
        515                 520


<210> SEQ ID NO 25
<211> LENGTH: 1608
<212> TYPE: DNA
<213> ORGANISM: Thalassiosira pseudonana

<400> SEQUENCE: 25

atgtctgaag atccatcaat ctttgaagtg tgtactggcc agctcggaac agatcttacc      60

gtcgagcttt tacaatgtgt ctctgatgga gctgaaagcg caaaggatga tgtcatcagt     120

ggcgtcaact ccttctacct catctttgca ggagccctcg ttttcttcat gcaagtcggt     180

ttcgccatgc tctgtgctgg atccatccgt gagaagaacg tcaagaatgt attgctttgg     240

aatctcctcg attctgccgg tggtgccttt ggtttctgga gtattggtta tgcatttgct     300

tatggtggtg atgatattac caagggaaag accttcatcg gaaacgctga cttcttcttg     360

agtggagaaa ctgatatgga gttttggttc ttccaatacg cctttgcgtg tgctctctcc     420

tccattgttg ctggaaccat tgctgagcgc accaagatga tggcctactt gtgctactca     480

atcttccttt gtggattcgt ctacccagtc tgtgctcatg ccttttggtc tcagaatgga     540

ttcctctctg ccttcgctgc tgaacctttg tggggttcgg gcgttattga ctttgcagga     600

tcgggaccag ttcacatgtg tggaggagtt gctgctcttg tcatggctat tattcttgga     660

cctcgtaggg gacgtttcta tgacgacgat ggtgtcgtat tggatgagcc aaagtccatg     720

ggacctcact ccgtcacttt gcaattcctc ggaacctttg ctctttggtt cggatggtat     780

ggattcaacc ctggtagctc catcttgatt gcgtcagctg cctctggcga cgttgcatcg     840

cttgctgccg tcaacactac gctcggatct gctgctggag cactttctgg tatgttcacc     900

tccacgatcg tcgacgaaag aaagactgga gtgtatactt gggatactac tgctgcaatg     960

aacggatgcc tcaccggttt ggttgctatt actgctggtt gcgctaccgt cgagccttgg    1020

gctgccttcg tcattgggct cactgctggt tgggtgtacc ttgctgcatc tgctcttatg    1080

cttcgcttca agattgatga tgctgtcgat gccatccccg ttcacatgtt cggaggatca    1140

tggggagttt tttgcactgg tcttttcacc agtcctcgcc gtcttattac tgcatacgga    1200

aatgacaata atgttggttg gttctacgaa tggggacgtg gaagtggaaa cttcactctc    1260

cttggctgcc agctcgtctc gattctcttt gtcttgggat ggtctgcttg catctttgct    1320
```

```
ccattctgct tggcactcaa aaccctcaac tggctccgca ttgaccctct cgaggaggag   1380

gttggtatgg atatcagtcg ccataaggga cctgcctacg agtcggaggg atctgctcat   1440

tctgatgcta tcgagaagtt gagtgcctcc cgtcgtgata ttatgaatgc ctctggaagt   1500

ggaaggggaa aaagtttcag caggtcgact cccacgaaag ctaacgagga gcccaaaatc   1560

gaagcaactg aggatgcagg ggcacccgct ggagaagcaa ctgcttag                1608


<210> SEQ ID NO 26
<211> LENGTH: 535
<212> TYPE: PRT
<213> ORGANISM: Thalassiosira pseudonana

<400> SEQUENCE: 26

Met Ser Glu Asp Pro Ser Ile Phe Glu Val Cys Thr Gly Gln Leu Gly
1               5                   10                  15

Thr Asp Leu Thr Val Glu Leu Leu Gln Cys Val Ser Asp Gly Ala Glu
            20                  25                  30

Ser Ala Lys Asp Asp Val Ile Ser Gly Val Asn Ser Phe Tyr Leu Ile
        35                  40                  45

Phe Ala Gly Ala Leu Val Phe Phe Met Gln Val Gly Phe Ala Met Leu
    50                  55                  60

Cys Ala Gly Ser Ile Arg Glu Lys Asn Val Lys Asn Val Leu Leu Trp
65                  70                  75                  80

Asn Leu Leu Asp Ser Ala Gly Gly Ala Phe Gly Phe Trp Ser Ile Gly
                85                  90                  95

Tyr Ala Phe Ala Tyr Gly Gly Asp Asp Ile Thr Lys Gly Lys Thr Phe
            100                 105                 110

Ile Gly Asn Ala Asp Phe Phe Leu Ser Gly Glu Thr Asp Met Glu Phe
        115                 120                 125

Trp Phe Phe Gln Tyr Ala Phe Ala Cys Ala Leu Ser Ser Ile Val Ala
    130                 135                 140

Gly Thr Ile Ala Glu Arg Thr Lys Met Met Ala Tyr Leu Cys Tyr Ser
145                 150                 155                 160

Ile Phe Leu Cys Gly Phe Val Tyr Pro Val Cys Ala His Ala Phe Trp
                165                 170                 175

Ser Gln Asn Gly Phe Leu Ser Ala Phe Ala Ala Glu Pro Leu Trp Gly
            180                 185                 190

Ser Gly Val Ile Asp Phe Ala Gly Ser Gly Pro Val His Met Cys Gly
        195                 200                 205

Gly Val Ala Ala Leu Val Met Ala Ile Ile Leu Gly Pro Arg Arg Gly
    210                 215                 220

Arg Phe Tyr Asp Asp Asp Gly Val Val Leu Asp Glu Pro Lys Ser Met
225                 230                 235                 240

Gly Pro His Ser Val Thr Leu Gln Phe Leu Gly Thr Phe Ala Leu Trp
                245                 250                 255

Phe Gly Trp Tyr Gly Phe Asn Pro Gly Ser Ser Ile Leu Ile Ala Ser
            260                 265                 270

Ala Ala Ser Gly Asp Val Ala Ser Leu Ala Ala Val Asn Thr Thr Leu
        275                 280                 285

Gly Ser Ala Ala Gly Ala Leu Ser Gly Met Phe Thr Ser Thr Ile Val
    290                 295                 300

Asp Glu Arg Lys Thr Gly Val Tyr Thr Trp Asp Thr Thr Ala Ala Met
305                 310                 315                 320

Asn Gly Cys Leu Thr Gly Leu Val Ala Ile Thr Ala Gly Cys Ala Thr
```

-continued

```
                325                 330                 335

Val Glu Pro Trp Ala Ala Phe Val Ile Gly Leu Thr Ala Gly Trp Val
            340                 345                 350

Tyr Leu Ala Ala Ser Ala Leu Met Leu Arg Phe Lys Ile Asp Asp Ala
        355                 360                 365

Val Asp Ala Ile Pro Val His Met Phe Gly Gly Ser Trp Gly Val Phe
    370                 375                 380

Cys Thr Gly Leu Phe Thr Ser Pro Arg Arg Leu Ile Thr Ala Tyr Gly
385                 390                 395                 400

Asn Asp Asn Asn Val Gly Trp Phe Tyr Glu Trp Gly Arg Gly Ser Gly
                405                 410                 415

Asn Phe Thr Leu Leu Gly Cys Gln Leu Val Ser Ile Leu Phe Val Leu
            420                 425                 430

Gly Trp Ser Ala Cys Ile Phe Ala Pro Phe Cys Leu Ala Leu Lys Thr
        435                 440                 445

Leu Asn Trp Leu Arg Ile Asp Pro Leu Glu Glu Glu Val Gly Met Asp
    450                 455                 460

Ile Ser Arg His Lys Gly Pro Ala Tyr Glu Ser Glu Gly Ser Ala His
465                 470                 475                 480

Ser Asp Ala Ile Glu Lys Leu Ser Ala Ser Arg Arg Asp Ile Met Asn
                485                 490                 495

Ala Ser Gly Ser Gly Arg Gly Lys Ser Phe Ser Arg Ser Thr Pro Thr
            500                 505                 510

Lys Ala Asn Glu Glu Pro Lys Ile Glu Ala Thr Glu Asp Ala Gly Ala
        515                 520                 525

Pro Ala Gly Glu Ala Thr Ala
    530                 535
```

<210> SEQ ID NO 27
<211> LENGTH: 1632
<212> TYPE: DNA
<213> ORGANISM: Thalassiosira pseudonana

<400> SEQUENCE: 27

```
atgtttcagg tatcaagagc tggacacgtg tcagtgtatg aggtctgcaa atccttcgtc     60

aacccagaag attctcaagc agatcagttt gatgcaatgc tccaatgtgt tggggaatcc    120

aacggcaaga gtatagacgc tttcttcctt atatacgcat catccctcgt cttcttcatg    180

caagccggct tcgccatgct ttgtgctgga tgcgttcaac acaagaatgt tcagaacagt    240

atgttgaaga acctcctaga tgcatgcggt gcagcccttg gcttctattc cgtcgggtat    300

gcatttgctt acggtggcat ggactattca gatccaaaca agacatttat cggcacagag    360

aactttttct tgatgggagt ggacgatttc atgttttggc tattccaatt tgcattcgct    420

gcaagtgctg ctaccattgt ggcaggaacg ttggctgaac ggtgtcaaat gacggcatac    480

ttgtgctact cagtggcagt gactggattt gtatatccag tagttgtaca ttcggtttgg    540

tctccgcagg gtttcttgtg cggacaggct gtgagcccgt tatttggagt tggtgtagta    600

gactttgcag gatcatcggt tgtgcatttg actggagggt gcattgcact cattgccacg    660

tatattctag gcccaaggcg agggagattc tatgatcaca gaggagaacc tcttgagaca    720

ccagtcgagt ttccgggtca ttcagctgca cttcaaatgc tcggtgcctt catattatgg    780

tttggatggt atggcttcaa tactggatca actctttcga tcaccggccc tggccaacat    840

caagtcgtca gccttgtagc tgtaaacaca accctcgcgg cggcctctgc ttgtgtggct    900

tcccttcttg ccagttatta tgtcatcgaa cgaaagactg gcgaaggtac attctcgctt    960
```

```
tcttcagcaa tgaatgggtg cttaggagga ttagtcagta tcactggtgg atgtgcagtg   1020

gtggagcctt gggcagccgt cgtaatcgga ttcatagcag ggttgttgta tctcttcacg   1080

tcaaagctat tgattcgttt gcgaatagac gatgcagtcg atgctattcc ggtccacttg   1140

tctaacggaa tatggggtac ggttgcggtg gggttgttcg catcgtcgaa tcgtttgcag   1200

ttggcttttg gaaaagtcgc tgatactggt gtgttcatgg gtggaaccgg taaactgttg   1260

ggatgtcaaa taattggtgt cttctttgtg cttggatgga tttccttcat tatgattccg   1320

ttcttctgct tccttcacta catgggatgg cttcgatctg agtcaattga tgaagtagaa   1380

gggcttgatt ccaagtatca tggattgcga aacaaagatg agcatagaca tgacgaagaa   1440

gaagacaata ctccatcaca ctacggcgaa ggcaattgca ggctgaggcg tagcattttg   1500

cgccatgagg aaagaatgag acaagaggac tcggcaatac ccgcaacttt ggtatcaagt   1560

gatgataggt tcacgtgtga ctcaggagga aatagcactt caatgctatc tactgctaag   1620

caatacacct ag                                                       1632


<210> SEQ ID NO 28
<211> LENGTH: 543
<212> TYPE: PRT
<213> ORGANISM: Thalassiosira pseudonana

<400> SEQUENCE: 28

Met Phe Gln Val Ser Arg Ala Gly His Val Ser Val Tyr Glu Val Cys
1               5                   10                  15

Lys Ser Phe Val Asn Pro Glu Asp Ser Gln Ala Asp Gln Phe Asp Ala
            20                  25                  30

Met Leu Gln Cys Val Gly Glu Ser Asn Gly Lys Ser Ile Asp Ala Phe
        35                  40                  45

Phe Leu Ile Tyr Ala Ser Ser Leu Val Phe Phe Met Gln Ala Gly Phe
    50                  55                  60

Ala Met Leu Cys Ala Gly Cys Val Gln His Lys Asn Val Gln Asn Ser
65                  70                  75                  80

Met Leu Lys Asn Leu Leu Asp Ala Cys Gly Ala Ala Leu Gly Phe Tyr
                85                  90                  95

Ser Val Gly Tyr Ala Phe Ala Tyr Gly Gly Met Asp Tyr Ser Asp Pro
            100                 105                 110

Asn Lys Thr Phe Ile Gly Thr Glu Asn Phe Phe Leu Met Gly Val Asp
        115                 120                 125

Asp Phe Met Phe Trp Leu Phe Gln Phe Ala Phe Ala Ala Ser Ala Ala
    130                 135                 140

Thr Ile Val Ala Gly Thr Leu Ala Glu Arg Cys Gln Met Thr Ala Tyr
145                 150                 155                 160

Leu Cys Tyr Ser Val Ala Val Thr Gly Phe Val Tyr Pro Val Val Val
                165                 170                 175

His Ser Val Trp Ser Pro Gln Gly Phe Leu Cys Gly Gln Ala Val Ser
            180                 185                 190

Pro Leu Phe Gly Val Gly Val Val Asp Phe Ala Gly Ser Ser Val Val
        195                 200                 205

His Leu Thr Gly Gly Cys Ile Ala Leu Ile Ala Thr Tyr Ile Leu Gly
    210                 215                 220

Pro Arg Arg Gly Arg Phe Tyr Asp His Arg Gly Glu Pro Leu Glu Thr
225                 230                 235                 240

Pro Val Glu Phe Pro Gly His Ser Ala Ala Leu Gln Met Leu Gly Ala
                245                 250                 255
```

```
Phe Ile Leu Trp Phe Gly Trp Tyr Gly Phe Asn Thr Gly Ser Thr Leu
            260                 265                 270

Ser Ile Thr Gly Pro Gly Gln His Gln Val Val Ser Leu Val Ala Val
        275                 280                 285

Asn Thr Thr Leu Ala Ala Ala Ser Ala Cys Val Ala Ser Leu Leu Ala
    290                 295                 300

Ser Tyr Tyr Val Ile Glu Arg Lys Thr Gly Glu Gly Thr Phe Ser Leu
305                 310                 315                 320

Ser Ser Ala Met Asn Gly Cys Leu Gly Gly Leu Val Ser Ile Thr Gly
                325                 330                 335

Gly Cys Ala Val Val Glu Pro Trp Ala Ala Val Val Ile Gly Phe Ile
            340                 345                 350

Ala Gly Leu Leu Tyr Leu Phe Thr Ser Lys Leu Leu Ile Arg Leu Arg
        355                 360                 365

Ile Asp Asp Ala Val Asp Ala Ile Pro Val His Leu Ser Asn Gly Ile
    370                 375                 380

Trp Gly Thr Val Ala Val Gly Leu Phe Ala Ser Ser Asn Arg Leu Gln
385                 390                 395                 400

Leu Ala Phe Gly Lys Val Ala Asp Thr Gly Val Phe Met Gly Gly Thr
                405                 410                 415

Gly Lys Leu Leu Gly Cys Gln Ile Ile Gly Val Phe Phe Val Leu Gly
            420                 425                 430

Trp Ile Ser Phe Ile Met Ile Pro Phe Phe Cys Phe Leu His Tyr Met
        435                 440                 445

Gly Trp Leu Arg Ser Glu Ser Ile Asp Glu Val Glu Gly Leu Asp Ser
    450                 455                 460

Lys Tyr His Gly Leu Arg Asn Lys Asp Glu His Arg His Asp Glu Glu
465                 470                 475                 480

Glu Asp Asn Thr Pro Ser His Tyr Gly Glu Gly Asn Cys Arg Leu Arg
                485                 490                 495

Arg Ser Ile Leu Arg His Glu Glu Arg Met Arg Gln Glu Asp Ser Ala
            500                 505                 510

Ile Pro Ala Thr Leu Val Ser Ser Asp Asp Arg Phe Thr Cys Asp Ser
        515                 520                 525

Gly Gly Asn Ser Thr Ser Met Leu Ser Thr Ala Lys Gln Tyr Thr
    530                 535                 540
```

<210> SEQ ID NO 29
<211> LENGTH: 1572
<212> TYPE: DNA
<213> ORGANISM: Thalassiosira pseudonana

<400> SEQUENCE: 29

```
atgtcctcgt cggtacggac gagcctgtac gaggcttgca aatctactca atccaactct      60

acgttttcca actctacgct cgatgatgca ctctctcgcc aggaacagat cttccgttgc     120

atttcggaat cgaacgccaa tagtattgat acgttctttc tgctctatgc ctcatcgctg     180

gtattcttta tgcaagccgg attcgcgatg ctctgtgcag gatcagtgag aaagaagaat     240

gtgactaata ccatgttgaa gaaccttctc gatgcttgcg gtgccgcact tgggttctat     300

tctgtgggat acgcctttgc atacggagga tcagtagacg ccgggaagaa gacgtttata     360

ggtatgagca acttctttct acaggacgtt gacaactata tgttttggct ctttcagttt     420

gcattcgctg caacatcagc tacaatcgta gcaggaacat tggctgaaag atgtcaaatg     480

acagcttacc tttgctactc aattgcattg acgggatttg tctacccagt tgtcgctcat     540
```

```
tcaatatgga gtcagcaggg gttcttatca gctactgctc aagatccatt atggggtaca    600
ggtttcattg actttgcggg atcaacagta gtacatctga cgggtggatt tacagctttg    660
attgcgacat atcttctagg gccacgcaga ggacggttct acgatgcgaa aggcaagcag    720
ttggaagtgc caaatccaat gcctggccat tcagctgcac ttcagatgct tggtatcttc    780
attttatggt ttggttggta tggtttcatt gttggatcag cgataactat catcggtccg    840
aatcaagaca agatcatctc tacctctgca gtgaatacga cactctctgc agcgtcatca    900
tgcttctctg ccttactcgt caactacgtc attgtcgaga ggcaatcggg agaaggagaa    960
ttcagtcttc tcgctgcaat gaacggatgc ttgagtggat tggtagcgat aacaggtgga   1020
tgcgcagtga tagcaccatg ggcagcaatt atcgtcggac ttttcgctgg cctcttgtac   1080
ttatttacgt caaaggtatt ggtacgagtt cgaatcgacg atgcagtaga agccattcct   1140
gttcacatga ctaacgggat atggggtagt ttcgcagttg gactatttgc cgctccatcg   1200
gagctgcaat tggtatacgg aaaagcaaat cacgttggac tattctattc ttggcatcaa   1260
gggagtggag atgggacgtt actcggtgtc caatgcttgg gcattctgtt tgtagtgggc   1320
tgggtgttct gtctcatgtc tcccttcttc ctgtttctga actacaaagg ctggttcaga   1380
gccgacgtcc tcaacgagat tgctggctta gatttgagtt atcatgatgg agtggatatg   1440
gaattggtga ctcagatacg caatcaaagg aagaacttgc acgtcaacag caggaatcgc   1500
tttagttcga atagtgcatg tcctcatcat acggcaacac atgtcgatac ctcaactgat   1560
gcatcacttt ga                                                       1572
```

<210> SEQ ID NO 30
<211> LENGTH: 511
<212> TYPE: PRT
<213> ORGANISM: Thalassiosira pseudonana

<400> SEQUENCE: 30

```
Met Ser Ser Ser Val Arg Thr Ser Leu Tyr Glu Ala Cys Lys Ser Thr
1               5                   10                  15

Gln Ser Asn Ser Thr Phe Ser Asn Ser Thr Leu Asp Asp Ala Leu Ser
            20                  25                  30

Arg Gln Glu Gln Ile Phe Arg Cys Ile Ser Glu Ser Asn Ala Asn Ser
        35                  40                  45

Ile Asp Thr Phe Phe Leu Leu Tyr Ala Ser Ser Leu Val Phe Phe Met
    50                  55                  60

Gln Ala Gly Phe Ala Met Leu Cys Ala Gly Ser Val Arg Lys Lys Asn
65                  70                  75                  80

Val Thr Asn Thr Met Leu Lys Asn Leu Leu Asp Ala Cys Gly Ala Ala
                85                  90                  95

Leu Gly Phe Tyr Ser Val Gly Tyr Ala Phe Ala Tyr Gly Gly Ser Val
            100                 105                 110

Asp Ala Gly Lys Lys Thr Phe Ile Gly Met Ser Asn Phe Phe Leu Gln
        115                 120                 125

Asp Val Asp Asn Tyr Met Phe Trp Leu Phe Gln Phe Ala Phe Ala Ala
    130                 135                 140

Thr Ser Ala Thr Ile Val Ala Gly Thr Leu Ala Glu Arg Cys Gln Met
145                 150                 155                 160

Thr Ala Tyr Leu Cys Tyr Ser Ile Ala Leu Thr Gly Phe Val Tyr Pro
                165                 170                 175

Val Val Ala His Ser Ile Trp Ser Gln Gln Gly Phe Leu Ser Ala Thr
            180                 185                 190
```

```
Ala Gln Asp Pro Leu Trp Gly Thr Gly Phe Ile Asp Phe Ala Gly Ser
        195                 200                 205

Thr Val Val His Leu Thr Gly Gly Phe Thr Ala Leu Ile Ala Thr Tyr
    210                 215                 220

Leu Leu Gly Pro Arg Arg Gly Arg Phe Tyr Asp Ala Lys Gly Lys Gln
225                 230                 235                 240

Leu Glu Val Pro Asn Pro Met Pro Gly His Ser Ala Ala Leu Gln Met
                245                 250                 255

Leu Gly Ile Phe Ile Leu Trp Phe Gly Trp Tyr Gly Phe Ile Val Gly
            260                 265                 270

Ser Ala Ile Thr Ile Ile Gly Pro Asn Gln Asp Lys Ile Ile Ser Thr
        275                 280                 285

Ser Ala Val Asn Thr Thr Leu Ser Ala Ala Ser Ser Cys Phe Ser Ala
    290                 295                 300

Leu Leu Val Asn Tyr Val Ile Val Glu Arg Gln Ser Gly Glu Gly Glu
305                 310                 315                 320

Phe Ser Leu Leu Ala Ala Met Asn Gly Cys Leu Ser Gly Leu Val Ala
                325                 330                 335

Ile Thr Gly Gly Cys Ala Val Ile Ala Pro Trp Ala Ala Ile Ile Val
            340                 345                 350

Gly Leu Phe Ala Gly Leu Leu Tyr Leu Phe Thr Ser Lys Val Leu Val
        355                 360                 365

Arg Val Arg Ile Asp Asp Ala Val Glu Ala Ile Pro Val His Met Thr
    370                 375                 380

Asn Gly Ile Trp Gly Ser Phe Ala Val Gly Leu Phe Ala Ala Pro Ser
385                 390                 395                 400

Glu Leu Gln Leu Val Tyr Gly Lys Ala Asn His Val Gly Leu Phe Tyr
                405                 410                 415

Ser Trp His Gln Gly Ser Gly Asp Gly Thr Leu Leu Gly Val Gln Cys
            420                 425                 430

Leu Gly Ile Leu Phe Val Val Gly Trp Val Phe Cys Leu Met Ser Pro
        435                 440                 445

Phe Phe Leu Phe Leu Asn Tyr Lys Gly Trp Phe Arg Ala Asp Val Leu
    450                 455                 460

Asn Glu Ile Ala Gly Leu Asp Leu Ser Tyr His Asp Gly Val Asp Met
465                 470                 475                 480

Glu Leu Val Thr Gln Ile Arg Asn Gln Arg Lys Asn Leu His Val Asn
                485                 490                 495

Ser Arg Asn Arg Phe Ser Ser Asn Ser Ala Cys Pro His His Thr
            500                 505                 510


<210> SEQ ID NO 31
<211> LENGTH: 1791
<212> TYPE: DNA
<213> ORGANISM: Thalassiosira pseudonana

<400> SEQUENCE: 31

atggcatcat caaccaccac agacacctat caaacatgcc tcagcgatct ctcggcgacg      60

tcgtctaatg gatcctcgcc caccaccgac gccctccttc agtgcatctc ctcctccttc     120

gacgctcaaa cggcctctac acatgcttca atcaacacct ttttcctcct ctatgcagcc     180

accctcgtct tcttcatgca agccggcttt gccatggtta gcgctggatg tgttaggacg     240

aataatgttc agaatacgct gctgaagaat ctgttggacg cctgcggtgc cgctcttgga     300

ttctacactg ttggatacgc cttcgcatgg ggaggatcgt tggatacggc taccaccgag     360
```

```
aggacgttca tcggtacaca gaacttcttt ttgatggatg tggatagctc tcaggattca    420
ttttggttgt ttcaattggc tttctgctcg gcatctgcaa cgattgtggc tggaacgttg    480
gctgaacgtt gtcaaatggt tgcctatctt gcatactcca tgacattggc aggatttgtc    540
tacccagtcg tcgtacacag tatctggagt ccgagtggat tcttgagtgc tactcgtgag    600
accgatctct tcttggatgt gggaatgatt gacttcgcag gatcaaccgt cgtgcatttg    660
acgggaggga tgactgcgtt gattgctacg attgtgctgg gaccgaggac gggaaggttc    720
tatgatttga gaggaaatcc gttgaaagta ccaaaggagt ttgcaggaca ttcattggct    780
ttgcaaatgt tgggggtgtt catcttgtgg tttggatggt atggcttcaa cgctggatcg    840
atcctcaaca tcaccaacga tctcaatcat acaatcgtca gtcatactgc catcaacaca    900
actcttgcag cttctgctgg atccatcatg actctcttcc tcagtaccgt cgtagccgaa    960
agatttacgg gggagatagt gtttagtcta tcttatgcca tgaatgggtg tttgagtgga   1020
ttggtggcaa tcacagctgg ctgctcagtg gtagaacact gggctgcaat cataatcggg   1080
cttgtaggag ggcattgta tttggcatgc tccaagttct tggtgaagaa acgtatcgat    1140
gatgcagttg atggtatccc tgtccacttg attaatggaa tctggggaac gttgagtgtc   1200
ggtctcttcg ctgtgcctga gttgttggag caagtgtatg gaaggggtga tcacgctggt   1260
tggttttaca gttggggaca aggatcagca gacgccaagt tgttgggagc tcaagtagtt   1320
ggaatcttgt ttgtcagtgg ctgggttatg atcacgatgt ttcctttctt ttgtttcttg   1380
cattatgttg gatggcttcg tgccgactct ctcgaggaag tagtcggtct cgacgctgct   1440
tactcccaag gtgttcttca gacgcgtgcc cgtgcccaaa gtgaggaaga gaacatggag   1500
cattacatca gtgaatatgt taagcagcgt gaggaaaaag cattcatcaa gaagatcaac   1560
agcaatagta ctcacggacg tactatcctt ggtgcaagca tgcattcaat gaacatcatt   1620
aattccagca tgcattccag aaaggacagt ctaccacgtg caattgaaag tctcaacaat   1680
tcaagacact ctggttcaag aggatcaaga tcaattaatg atattgcgat tgacaatttg   1740
catggtcaat ctgaggatgg ttttgctgca cctgatgagg gcagtgctta g            1791
```

<210> SEQ ID NO 32
<211> LENGTH: 596
<212> TYPE: PRT
<213> ORGANISM: Thalassiosira pseudonana

<400> SEQUENCE: 32

```
Met Ala Ser Ser Thr Thr Thr Asp Thr Tyr Gln Thr Cys Leu Ser Asp
1               5                   10                  15

Leu Ser Ala Thr Ser Ser Asn Gly Ser Ser Pro Thr Thr Asp Ala Leu
            20                  25                  30

Leu Gln Cys Ile Ser Ser Ser Phe Asp Ala Gln Thr Ala Ser Thr His
        35                  40                  45

Ala Ser Ile Asn Thr Phe Phe Leu Leu Tyr Ala Ala Thr Leu Val Phe
    50                  55                  60

Phe Met Gln Ala Gly Phe Ala Met Val Ser Ala Gly Cys Val Arg Thr
65                  70                  75                  80

Asn Asn Val Gln Asn Thr Leu Leu Lys Asn Leu Leu Asp Ala Cys Gly
                85                  90                  95

Ala Ala Leu Gly Phe Tyr Thr Val Gly Tyr Ala Phe Ala Trp Gly Gly
            100                 105                 110

Ser Leu Asp Thr Ala Thr Thr Glu Arg Thr Phe Ile Gly Thr Gln Asn
        115                 120                 125
```

```
Phe Phe Leu Met Asp Val Asp Ser Ser Gln Asp Ser Phe Trp Leu Phe
    130                 135                 140

Gln Leu Ala Phe Cys Ser Ala Ser Ala Thr Ile Val Ala Gly Thr Leu
145                 150                 155                 160

Ala Glu Arg Cys Gln Met Val Ala Tyr Leu Ala Tyr Ser Met Thr Leu
                165                 170                 175

Ala Gly Phe Val Tyr Pro Val Val Val His Ser Ile Trp Ser Pro Ser
            180                 185                 190

Gly Phe Leu Ser Ala Thr Arg Glu Thr Asp Leu Phe Leu Asp Val Gly
        195                 200                 205

Met Ile Asp Phe Ala Gly Ser Thr Val Val His Leu Thr Gly Gly Met
    210                 215                 220

Thr Ala Leu Ile Ala Thr Ile Val Leu Gly Pro Arg Thr Gly Arg Phe
225                 230                 235                 240

Tyr Asp Leu Arg Gly Asn Pro Leu Lys Val Pro Lys Glu Phe Ala Gly
                245                 250                 255

His Ser Leu Ala Leu Gln Met Leu Gly Val Phe Ile Leu Trp Phe Gly
            260                 265                 270

Trp Tyr Gly Phe Asn Ala Gly Ser Ile Leu Asn Ile Thr Asn Asp Leu
        275                 280                 285

Asn His Thr Ile Val Ser His Thr Ala Ile Asn Thr Thr Leu Ala Ala
    290                 295                 300

Ser Ala Gly Ser Ile Met Thr Leu Phe Leu Ser Thr Val Val Ala Glu
305                 310                 315                 320

Arg Phe Thr Gly Glu Ile Val Phe Ser Leu Ser Tyr Ala Met Asn Gly
                325                 330                 335

Cys Leu Ser Gly Leu Val Ala Ile Thr Ala Gly Cys Ser Val Val Glu
            340                 345                 350

His Trp Ala Ala Ile Ile Ile Gly Leu Val Gly Gly Ala Leu Tyr Leu
        355                 360                 365

Ala Cys Ser Lys Phe Leu Val Lys Lys Arg Ile Asp Asp Ala Val Asp
    370                 375                 380

Gly Ile Pro Val His Leu Ile Asn Gly Ile Trp Gly Thr Leu Ser Val
385                 390                 395                 400

Gly Leu Phe Ala Val Pro Glu Leu Leu Glu Gln Val Tyr Gly Arg Gly
                405                 410                 415

Asp His Ala Gly Trp Phe Tyr Ser Trp Gly Gln Gly Ser Ala Asp Ala
            420                 425                 430

Lys Leu Leu Gly Ala Gln Val Val Gly Ile Leu Phe Val Ser Gly Trp
        435                 440                 445

Val Met Ile Thr Met Phe Pro Phe Phe Cys Phe Leu His Tyr Val Gly
    450                 455                 460

Trp Leu Arg Ala Asp Ser Leu Glu Glu Val Val Gly Leu Asp Ala Ala
465                 470                 475                 480

Tyr Ser Gln Gly Val Leu Gln Thr Arg Ala Arg Ala Gln Ser Glu Glu
                485                 490                 495

Glu Asn Met Glu His Tyr Ile Ser Glu Tyr Val Lys Gln Arg Glu Glu
            500                 505                 510

Lys Ala Phe Ile Lys Lys Ile Asn Ser Asn Ser Thr His Gly Arg Thr
        515                 520                 525

Ile Leu Gly Ala Ser Met His Ser Met Asn Ile Ile Asn Ser Ser Met
    530                 535                 540

His Ser Arg Lys Asp Ser Leu Pro Arg Ala Ile Glu Ser Leu Asn Asn
```

-continued

```
545                 550                 555                 560

Ser Arg His Ser Gly Ser Arg Gly Ser Arg Ser Ile Asn Asp Ile Ala
                565                 570                 575

Ile Asp Asn Leu His Gly Gln Ser Glu Asp Gly Phe Ala Ala Pro Asp
            580                 585                 590

Glu Gly Ser Ala
        595


<210> SEQ ID NO 33
<211> LENGTH: 407
<212> TYPE: PRT
<213> ORGANISM: Artificial sequence
<220> FEATURE:
<223> OTHER INFORMATION: Conserved domain comprised within SEQ ID NO :
      02 and within SEQ ID NO : 04

<400> SEQUENCE: 33

Met Gln Ala Gly Phe Ala Met Leu Cys Ala Gly Ser Val Arg Gln Lys
1               5                   10                  15

Asn Val Lys Asn Ile Met Leu Lys Asn Leu Leu Asp Ala Cys Gly Gly
            20                  25                  30

Ala Ile Gly Phe Tyr Thr Val Gly Phe Gly Phe Ala Tyr Gly Gly Asp
        35                  40                  45

Asp Thr Thr Asp Lys Thr Phe Ile Gly Asn Ser Tyr Phe Ala Leu Arg
    50                  55                  60

Asp Tyr Thr Asn Tyr Ala Gly Phe Phe Phe Gln Phe Ala Phe Ala Ala
65                  70                  75                  80

Thr Ala Ala Thr Ile Val Ala Gly Thr Val Ala Glu Arg Cys Lys Met
                85                  90                  95

Ser Ala Tyr Leu Cys Tyr Ser Leu Phe Leu Thr Gly Phe Val Tyr Pro
            100                 105                 110

Val Val Val Arg Ser Val Trp Ser Ser Asn Gly Phe Leu Ser Ala Phe
        115                 120                 125

Ser Ala Asp Pro Phe Gln Gly Val Gly Thr Val Asp Phe Ala Gly Ser
    130                 135                 140

Gly Val Val His Met Thr Gly Gly Leu Thr Ala Leu Ile Ala Ala Ile
145                 150                 155                 160

Val Leu Gly Pro Arg Lys Gly Arg Phe Tyr Asp Glu Asp Gly Asn Pro
                165                 170                 175

Leu Glu Thr Pro Ala Ser Phe Pro Ala His Ser Val Ala Leu Gln Ile
            180                 185                 190

Leu Gly Thr Phe Ile Leu Trp Phe Gly Trp Tyr Gly Phe Asn Pro Gly
        195                 200                 205

Ser Ala Leu Lys Ile Ala Asn Ala Asp Ser Ala Ala Thr Ala Ala Leu
    210                 215                 220

Cys Ala Val Thr Thr Thr Met Ala Ala Ala Ala Gly Cys Val Ser Ala
225                 230                 235                 240

Met Phe Thr Asp Ser Ile Ile Asp Gly Met Ala Thr Gly Glu Thr Thr
                245                 250                 255

Tyr Asp Leu Thr Met Ala Met Asn Gly Cys Leu Ala Gly Leu Val Ala
            260                 265                 270

Val Thr Ala Gly Thr Ser Val Val Thr Pro Trp Ala Ala Ile Ile Ile
        275                 280                 285

Gly Val Val Gly Gly Trp Val Tyr Ile Gly Met Ser Lys Leu Leu Ile
    290                 295                 300

Lys Leu Lys Ile Asp Asp Ala Val Asp Ala Ile Pro Val His Phe Ala
```

-continued

```
305                 310                 315                 320

Asn Gly Phe Trp Gly Val Leu Ala Thr Gly Leu Phe Ala Asn Gly Gly
                325                 330                 335

Leu Met Ala Thr Ala Gly Tyr Asn Ser Glu His Glu Gly Trp Phe Tyr
            340                 345                 350

Glu Trp Gly Ser Gly Ser Gly Asp Gly Ser Leu Leu Ile Cys Gln Leu
        355                 360                 365

Ala Cys Leu Ala Trp Ile Ile Gly Trp Val Thr Thr Ile Met Thr Pro
    370                 375                 380

Phe Phe Ile Leu Leu Asn Met Ala Gly Met Phe Arg Val Asp Pro Leu
385                 390                 395                 400

Glu Glu Glu Val Gly Leu Asp
                405


<210> SEQ ID NO 34
<211> LENGTH: 2194
<212> TYPE: DNA
<213> ORGANISM: Oryza sativa

<400> SEQUENCE: 34

aatccgaaaa gtttctgcac cgttttcacc ccctaactaa caatataggg aacgtgtgct      60

aaatataaaa tgagacctta tatatgtagc gctgataact agaactatgc aagaaaaact     120

catccaccta ctttagtggc aatcgggcta aataaaaaag agtcgctaca ctagtttcgt     180

tttccttagt aattaagtgg gaaaatgaaa tcattattgc ttagaatata cgttcacatc     240

tctgtcatga agttaaatta ttcgaggtag ccataattgt catcaaactc ttcttgaata     300

aaaaaatctt tctagctgaa ctcaatgggt aaagagagag atttttttta aaaaaataga     360

atgaagatat tctgaacgta ttggcaaaga tttaaacata taattatata attttatagt     420

ttgtgcattc gtcatatcgc acatcattaa ggacatgtct tactccatcc caatttttat     480

ttagtaatta aagacaattg acttattttt attatttatc ttttttcgat tagatgcaag     540

gtacttacgc acacactttg tgctcatgtg catgtgtgag tgcacctcct caatacacgt     600

tcaactagca acacatctct aatatcactc gcctatttaa tacatttagg tagcaatatc     660

tgaattcaag cactccacca tcaccagacc acttttaata atatctaaaa tacaaaaaat     720

aattttacag aatagcatga aaagtatgaa acgaactatt taggtttttc acatacaaaa     780

aaaaaaagaa ttttgctcgt gcgcgagcgc caatctccca tattgggcac acaggcaaca     840

acagagtggc tgcccacaga acaacccaca aaaaacgatg atctaacgga ggacagcaag     900

tccgcaacaa ccttttaaca gcaggctttg cggccaggag agaggaggag aggcaaagaa     960

aaccaagcat cctccttctc ccatctataa attcctcccc ccttttcccc tctctatata    1020

ggaggcatcc aagccaagaa gagggagagc accaaggaca cgcgactagc agaagccgag    1080

cgaccgcctt ctcgatccat atcttccggt cgagttcttg gtcgatctct tccctcctcc    1140

acctcctcct cacagggtat gtgcctccct tcggttgttc ttggatttat tgttctaggt    1200

tgtgtagtac gggcgttgat gttaggaaag gggatctgta tctgtgatga ttcctgttct    1260

tggatttggg atagaggggt tcttgatgtt gcatgttatc ggttcggttt gattagtagt    1320

atggttttca atcgtctgga gagctctatg gaaatgaaat ggtttaggga tcggaatctt    1380

gcgattttgt gagtaccttt tgtttgaggt aaaatcagag caccggtgat tttgcttggt    1440

gtaataaagt acggttgttt ggtcctcgat tctggtagtg atgcttctcg atttgacgaa    1500

gctatccttt gtttattccc tattgaacaa aaataatcca actttgaaga cggtcccgtt    1560
```

```
gatgagattg aatgattgat tcttaagcct gtccaaaatt tcgcagctgg cttgtttaga   1620

tacagtagtc cccatcacga aattcatgga aacagttata atcctcagga acaggggatt   1680

ccctgttctt ccgatttgct ttagtcccag aatttttttt cccaaatatc ttaaaaagtc   1740

actttctggt tcagttcaat gaattgattg ctacaaataa tgcttttata gcgttatcct   1800

agctgtagtt cagttaatag gtaatacccc tatagtttag tcaggagaag aacttatccg   1860

atttctgatc tccattttta attatatgaa atgaactgta gcataagcag tattcatttg   1920

gattattttt tttattagct ctcacccctt cattattctg agctgaaagt ctggcatgaa   1980

ctgtcctcaa ttttgttttc aaattcacat cgattatcta tgcattatcc tcttgtatct   2040

acctgtagaa gtttcttttt ggttattcct tgactgcttg attacagaaa gaaatttatg   2100

aagctgtaat cgggatagtt atactgcttg ttcttatgat tcatttcctt tgtgcagttc   2160

ttggtgtagc ttgccacttt caccagcaaa gttc                                2194


<210> SEQ ID NO 35
<211> LENGTH: 50
<212> TYPE: DNA
<213> ORGANISM: Artificial sequence
<220> FEATURE:
<223> OTHER INFORMATION: primer: prm09458

<400> SEQUENCE: 35

ggggacaagt ttgtacaaaa aagcaggctt aaacaatgat gcaggccggg                 50


<210> SEQ ID NO 36
<211> LENGTH: 49
<212> TYPE: DNA
<213> ORGANISM: Artificial sequence
<220> FEATURE:
<223> OTHER INFORMATION: primer: prm09459

<400> SEQUENCE: 36

ggggaccact ttgtacaaga aagctgggta cacgagcagc aattaaacc                  49


<210> SEQ ID NO 37
<211> LENGTH: 632
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (1)..(15)
<223> OTHER INFORMATION: Xaa can be any naturally occurring amino acid
<220> FEATURE:
<221> NAME/KEY: misc_feature
<222> LOCATION: (17)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (32)..(44)
```

<223> OTHER INFORMATION: Xaa can be any naturally occurring amino acid
<220> FEATURE:
<221> NAME/KEY: misc_feature
<222> LOCATION: (46)..(49)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (56)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (141)..(153)
<223> OTHER INFORMATION: Xaa can be any naturally occurring amino acid
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (165)..(168)
<223> OTHER INFORMATION: Xaa can be any naturally occurring amino acid
<220> FEATURE:
<221> NAME/KEY: misc_feature
<222> LOCATION: (170)..(173)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (226)..(226)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:
<221> NAME/KEY: misc_feature
<222> LOCATION: (241)..(241)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (285)..(285)
<223> OTHER INFORMATION: Xaa can be any naturally occurring amino acid
<220> FEATURE:
<221> NAME/KEY: misc_feature
<222> LOCATION: (320)..(322)
<223> OTHER INFORMATION: Xaa can be any naturally occurring amino acid
<220> FEATURE:
<221> NAME/KEY: misc_feature
<222> LOCATION: (324)..(324)
<223> OTHER INFORMATION: Xaa can be any naturally occurring amino acid
<220> FEATURE:
<221> NAME/KEY: misc_feature
<222> LOCATION: (327)..(327)

<223> OTHER INFORMATION: Xaa can be any naturally occurring amino acid
<220> FEATURE:
<221> NAME/KEY: misc_feature
<222> LOCATION: (351)..(352)
<223> OTHER INFORMATION: Xaa can be any naturally occurring amino acid
<220> FEATURE:
<221> NAME/KEY: misc_feature
<222> LOCATION: (358)..(358)
<223> OTHER INFORMATION: Xaa can be any naturally occurring amino acid
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid
<220> FEATURE:
<221> NAME/KEY: misc_feature
<222> LOCATION: (427)..(427)
<223> OTHER INFORMATION: Xaa can be any naturally occurring amino acid
<220> FEATURE:
<221> NAME/KEY: misc_feature
<222> LOCATION: (430)..(430)
<223> OTHER INFORMATION: Xaa can be any naturally occurring amino acid
<220> FEATURE:
<221> NAME/KEY: misc_feature
<222> LOCATION: (443)..(444)
<223> OTHER INFORMATION: Xaa can be any naturally occurring amino acid
<220> FEATURE:
<221> NAME/KEY: misc_feature
<222> LOCATION: (447)..(447)
<223> OTHER INFORMATION: Xaa can be any naturally occurring amino acid
<220> FEATURE:
<221> NAME/KEY: misc_feature
<222> LOCATION: (451)..(453)
<223> OTHER INFORMATION: Xaa can be any naturally occurring amino acid
<220> FEATURE:
<221> NAME/KEY: misc_feature
<222> LOCATION: (455)..(455)
<223> OTHER INFORMATION: Xaa can be any naturally occurring amino acid
<220> FEATURE:
<221> NAME/KEY: misc_feature
<222> LOCATION: (463)..(463)
<223> OTHER INFORMATION: Xaa can be any naturally occurring amino acid
<220> FEATURE:
<221> NAME/KEY: misc_feature
<222> LOCATION: (465)..(465)
<223> OTHER INFORMATION: Xaa can be any naturally occurring amino acid
<220> FEATURE:
<221> NAME/KEY: misc_feature
<222> LOCATION: (469)..(469)
<223> OTHER INFORMATION: Xaa can be any naturally occurring amino acid
<220> FEATURE:
<221> NAME/KEY: misc_feature
<222> LOCATION: (473)..(473)
<223> OTHER INFORMATION: Xaa can be any naturally occurring amino acid
<220> FEATURE:
<221> NAME/KEY: misc_feature
<222> LOCATION: (486)..(487)
<223> OTHER INFORMATION: Xaa can be any naturally occurring amino acid
<220> FEATURE:
<221> NAME/KEY: misc_feature
<222> LOCATION: (490)..(490)
<223> OTHER INFORMATION: Xaa can be any naturally occurring amino acid
<220> FEATURE:
<221> NAME/KEY: misc_feature
<222> LOCATION: (519)..(519)
<223> OTHER INFORMATION: Xaa can be any naturally occurring amino acid
<220> FEATURE:
<221> NAME/KEY: misc_feature
<222> LOCATION: (521)..(521)
<223> OTHER INFORMATION: Xaa can be any naturally occurring amino acid
<220> FEATURE:
<221> NAME/KEY: misc_feature
<222> LOCATION: (523)..(523)

```
<223> OTHER INFORMATION: Xaa can be any naturally occurring amino acid
<220> FEATURE:
<221> NAME/KEY: misc_feature
<222> LOCATION: (525)..(536)
<223> OTHER INFORMATION: Xaa can be any naturally occurring amino acid
<220> FEATURE:
<221> NAME/KEY: misc_feature
<222> LOCATION: (540)..(545)
<223> OTHER INFORMATION: Xaa can be any naturally occurring amino acid
<220> FEATURE:
<221> NAME/KEY: misc_feature
<222> LOCATION: (547)..(562)
<223> OTHER INFORMATION: Xaa can be any naturally occurring amino acid
<220> FEATURE:
<221> NAME/KEY: misc_feature
<222> LOCATION: (564)..(632)
<223> OTHER INFORMATION: Xaa can be any naturally occurring amino acid

<400> SEQUENCE: 37

Xaa Xaa Xaa Xaa Xaa Xaa Xaa Xaa Xaa Xaa Xaa Xaa Xaa Xaa Xaa Ser
1               5                   10                  15

Xaa Xaa Xaa Thr Xaa Ile Tyr Glu Xaa Cys Xaa Gly Xaa Xaa Gly Xaa
            20                  25                  30

Xaa Xaa Xaa Xaa Xaa Xaa Xaa Xaa Xaa Xaa Xaa Xaa Ser Xaa Xaa Xaa
        35                  40                  45

Xaa Leu Leu Xaa Cys Val Ser Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Ile Xaa Thr Phe
65                  70                  75                  80

Phe Leu Leu Phe Ala Gly Ala Leu Val Phe Phe Met Gln Ala Gly Phe
                85                  90                  95

Ala Met Leu Cys Ala Gly Ser Val Arg Xaa Lys Asn Val Gln Asn Thr
            100                 105                 110

Met Leu Lys Asn Leu Leu Asp Ala Cys Gly Ala Ala Leu Gly Phe Trp
        115                 120                 125

Ser Val Gly Tyr Ala Phe Ala Tyr Gly Gly Xaa Asp Xaa Xaa Xaa Xaa
    130                 135                 140

Xaa Xaa Xaa Xaa Xaa Xaa Xaa Xaa Xaa Lys Thr Phe Ile Gly Xaa Ser
145                 150                 155                 160

Asn Phe Phe Leu Xaa Xaa Xaa Xaa Asp Xaa Xaa Xaa Xaa Tyr Ala Phe
                165                 170                 175

Trp Phe Phe Gln Phe Ala Phe Ala Ala Thr Ala Ala Thr Ile Val Ala
            180                 185                 190

Gly Thr Leu Ala Glu Arg Cys Gln Met Xaa Ala Tyr Leu Cys Tyr Ser
        195                 200                 205

Val Phe Leu Thr Gly Phe Val Tyr Pro Val Val Ala His Ser Ile Trp
    210                 215                 220

Ser Xaa Asn Gly Phe Leu Ser Ala Phe Ala Xaa Asp Pro Leu Trp Gly
225                 230                 235                 240

Xaa Val Gly Val Ile Asp Phe Ala Gly Ser Gly Val Val His Met Thr
                245                 250                 255

Gly Gly Val Thr Ala Leu Val Ala Thr Ile Ile Leu Gly Pro Arg Arg
            260                 265                 270

Gly Arg Phe Tyr Asp Xaa Asp Gly Asn Xaa Leu Glu Xaa Pro Lys Ser
        275                 280                 285

Phe Pro Gly His Ser Val Ala Leu Gln Met Leu Gly Thr Phe Ile Leu
    290                 295                 300

Trp Phe Gly Trp Tyr Gly Phe Asn Pro Gly Ser Ala Leu Leu Ile Xaa
305                 310                 315                 320
```

-continued

```
Xaa Xaa Ala Xaa Ser Ala Xaa Val Ala Ala Leu Ala Ala Val Asn Thr
                325                 330                 335

Thr Leu Ala Ala Ala Ser Gly Ala Val Ser Ala Leu Phe Thr Xaa Xaa
            340                 345                 350

Trp Ile Glu Glu Arg Xaa Thr Gly Glu Xaa Ser Phe Asp Leu Thr Xaa
        355                 360                 365

Ala Met Asn Gly Cys Leu Ala Gly Leu Val Ala Ile Thr Ala Gly Cys
    370                 375                 380

Ala Val Val Glu Pro Trp Ala Ala Ile Val Ile Gly Ile Val Ala Gly
385                 390                 395                 400

Trp Leu Tyr Leu Xaa Gly Ser Lys Leu Leu Val Lys Leu Lys Ile Asp
                405                 410                 415

Asp Ala Val Asp Ala Ile Pro Val His Met Xaa Asn Gly Xaa Trp Gly
            420                 425                 430

Val Leu Ala Val Gly Leu Phe Ala Ser Pro Xaa Xaa Leu Leu Xaa Ala
        435                 440                 445

Tyr Gly Xaa Xaa Xaa His Xaa Gly Trp Phe Tyr Ser Trp Gly Xaa Gly
    450                 455                 460

Xaa Gly Asp Gly Xaa Leu Leu Gly Xaa Gln Leu Val Gly Ile Leu Phe
465                 470                 475                 480

Ile Leu Gly Trp Val Xaa Xaa Ile Met Xaa Pro Phe Phe Val Phe Leu
                485                 490                 495

Asn Tyr Leu Gly Trp Phe Arg Ser Asp Pro Leu Glu Glu Ile Val Gly
            500                 505                 510

Leu Asp Ile Ser Tyr His Xaa Gly Xaa Ala Xaa Asp Xaa Xaa Xaa Xaa
        515                 520                 525

Xaa Xaa Xaa Xaa Xaa Xaa Xaa Xaa Glu Tyr Val Xaa Xaa Xaa Xaa Xaa
    530                 535                 540

Xaa Arg Xaa Xaa Xaa Xaa Xaa Xaa Xaa Xaa Xaa Xaa Xaa Xaa Xaa Xaa
545                 550                 555                 560

Xaa Xaa Arg Xaa Xaa Xaa Xaa Xaa Xaa Xaa Xaa Xaa Xaa Xaa Xaa Xaa
                565                 570                 575

Xaa Xaa Xaa Xaa Xaa Xaa Xaa Xaa Xaa Xaa Xaa Xaa Xaa Xaa Xaa Xaa
            580                 585                 590

Xaa Xaa Xaa Xaa Xaa Xaa Xaa Xaa Xaa Xaa Xaa Xaa Xaa Xaa Xaa Xaa
        595                 600                 605

Xaa Xaa Xaa Xaa Xaa Xaa Xaa Xaa Xaa Xaa Xaa Xaa Xaa Xaa Xaa Xaa
    610                 615                 620

Xaa Xaa Xaa Xaa Xaa Xaa Xaa Xaa
625                 630


<210> SEQ ID NO 38
<211> LENGTH: 26
<212> TYPE: PRT
<213> ORGANISM: Artificial sequence
<220> FEATURE:
<223> OTHER INFORMATION: PS01219

<400> SEQUENCE: 38

Asp Phe Ala Gly Ser Gly Val Val His Met Thr Gly Gly Val Thr Ala
1               5                   10                  15

Leu Val Ala Thr Ile Ile Leu Gly Pro Arg
            20                  25
```